United States Patent
Rogers et al.

(10) Patent No.: US 12,128,028 B2
(45) Date of Patent: Oct. 29, 2024

(54) HETEROCYCLIC SULFONAMIDE DERIVATIVES AND PHARMACEUTICAL USES THEREOF

(71) Applicant: METRION BIOSCIENCES LIMITED, Great Abingdon (GB)

(72) Inventors: Marc Rogers, Great Abingdon (GB); Robert Kirby, Great Abingdon (GB); Gakujun Shomi, Great Abingdon (GB); Takuya Matsuo, Great Abingdon (GB); Satoru Kobayashi, Great Abingdon (GB); Junichiro Kanazawa, Great Abingdon (GB); Nobutaka Yamaoka, Great Abingdon (GB); Makoto Torizuka, Great Abingdon (GB); Koichi Suzawa, Great Abingdon (GB)

(73) Assignee: METRION BIOSCIENCES LIMITED, Great Abingdon (GB)

( * ) Notice: Subject to any disclaimer, the term of this patent is extended or adjusted under 35 U.S.C. 154(b) by 888 days.

(21) Appl. No.: 17/258,273

(22) PCT Filed: Jul. 5, 2019

(86) PCT No.: PCT/GB2019/051903
§ 371 (c)(1),
(2) Date: Jan. 6, 2021

(87) PCT Pub. No.: WO2020/008206
PCT Pub. Date: Jan. 9, 2020

(65) Prior Publication Data
US 2021/0275499 A1    Sep. 9, 2021

(30) Foreign Application Priority Data
Jul. 6, 2018 (GB) .................................. 1811165

(51) Int. Cl.
| | | |
|---|---|---|
| *A61K 31/4164* | (2006.01) |
| *A61K 31/4178* | (2006.01) |
| *A61K 31/439* | (2006.01) |
| *A61K 31/4439* | (2006.01) |
| *A61K 31/454* | (2006.01) |
| *A61K 31/46* | (2006.01) |
| *A61K 31/5377* | (2006.01) |
| *A61K 31/55* | (2006.01) |
| *C07D 233/28* | (2006.01) |
| *C07D 235/02* | (2006.01) |
| *C07D 401/06* | (2006.01) |
| *C07D 401/12* | (2006.01) |
| *C07D 403/06* | (2006.01) |
| *C07D 403/12* | (2006.01) |
| *C07D 405/12* | (2006.01) |
| *C07D 409/12* | (2006.01) |
| *C07D 471/08* | (2006.01) |
| *C07D 491/107* | (2006.01) |

(52) U.S. Cl.
CPC ...... *A61K 31/4164* (2013.01); *A61K 31/4178* (2013.01); *A61K 31/439* (2013.01); *A61K 31/4439* (2013.01); *A61K 31/454* (2013.01); *A61K 31/46* (2013.01); *A61K 31/5377* (2013.01); *A61K 31/55* (2013.01); *C07D 233/28* (2013.01); *C07D 235/02* (2013.01); *C07D 401/06* (2013.01); *C07D 401/12* (2013.01); *C07D 403/06* (2013.01); *C07D 403/12* (2013.01); *C07D 405/12* (2013.01); *C07D 409/12* (2013.01); *C07D 471/08* (2013.01); *C07D 491/107* (2013.01)

(58) Field of Classification Search
CPC ............ A61K 31/4164; A61K 31/4178; A61K 31/439
USPC ..................................................... 514/210.16
See application file for complete search history.

(56) References Cited

FOREIGN PATENT DOCUMENTS

| | | |
|---|---|---|
| WO | 02/08183 A2 | 1/2002 |
| WO | 02/060874 A1 | 8/2002 |
| WO | 2018/107072 A1 | 6/2018 |

OTHER PUBLICATIONS

Coghlan et al., "Recent Developments in the Biology and Medicinal Chemistry of Potassium Channel Modulators: Update from a Decade of Progress," Journal of Medicinal Chemistry, vol. 44, No. 11, 2001, pp. 1627-1653.
International Search Report and Written Opinion of the International Searching Authority for International Application No. PCT/GB2019/051903 mailed Oct. 4, 2019.

*Primary Examiner* — Jeffrey S Lundgren
*Assistant Examiner* — Heather Dahlin
(74) *Attorney, Agent, or Firm* — Heslin Rothenberg Farley & Mesiti P.C.

(57) ABSTRACT

The invention relates to heterocyclic sulfonamide derivatives and their use in the treatment and prophylaxis of autoimmune, inflammatory, cardiovascular, neuronal, auditory, renal and metabolic mediated diseases, and to compositions containing said derivatives and processes for their preparation.

23 Claims, No Drawings

HETEROCYCLIC SULFONAMIDE DERIVATIVES AND PHARMACEUTICAL USES THEREOF

CROSS REFERENCE TO RELATED APPLICATIONS

This application is a national stage filing under section 371 of International Application No. PCT/GB2019/051903, filed on Jul. 5, 2019, and published on Jan. 9, 2020 as WO 2020/008206 A1, which claims priority to Great Britain Application No. 1811165.8, filed on Jul. 6, 2018. The entire contents of WO 2020/008206 A1 are hereby incorporated herein by reference.

FIELD OF THE INVENTION

The invention relates to heterocyclic sulfonamide derivatives and their use in the treatment and prophylaxis of autoimmune, inflammatory, cardiovascular, neuronal, auditory, renal and metabolic mediated diseases, and to compositions containing said derivatives and processes for their preparation.

BACKGROUND OF THE INVENTION

Ion channels are proteins that span the lipid bilayer of the cell membrane and provide an aqueous pathway through which specific ions such as $Na^+$, $K^+$, $Ca^{2+}$ and $Cl^-$ can pass (Herbert (1998) Am. J. Med 104, 87-98). Potassium channels represent the largest and most diverse subgroup of ion channels and they play a central role in regulating the membrane potential and controlling cellular excitability (Armstrong & Hille (1998) Neuron 20, 371-380). Potassium channels have been categorized into gene families based on their amino acid sequence and their biophysical properties (for nomenclature see Gutman et al. (2003) Pharmacol Rev. December 55(4), 583-586).

Compounds which modulate potassium channels have multiple therapeutic applications in several disease areas including autoimmune, inflammatory, cardiovascular, neuronal, auditory, renal and metabolic mediated diseases (Shieh et al (2000) Pharmacol Rev 52(4), 557-594; Ford et al (2002) Prog Drug Res 58, 133-168, Xie et al (2004) Current Drug Discovery, 31-33; Cahalan et al (1997) Current Opinion in Biotechnology 8, 749-756). The potassium channel Kv1.3 is found in a number of tissues including neurons, blood cells, osteoclasts, macrophages, epithelia, and T- and B-lymphocytes. Furthermore, Kv1.3 inhibition has been shown to modulate T-cell function which has implications in many autoimmune diseases including psoriasis, rheumatoid arthritis, multiple sclerosis, obesity, diabetes and inflammatory bowel disease (Beeton et al (2006) PNAS 46, 103, 17414-17419).

There is therefore a need to provide effective Kv1.3 inhibitors for the treatment of autoimmune, inflammatory, cardiovascular, neuronal, auditory, renal and metabolic mediated diseases.

SUMMARY OF THE INVENTION

According to a first aspect of the invention, there is provided a compound of formula (I):

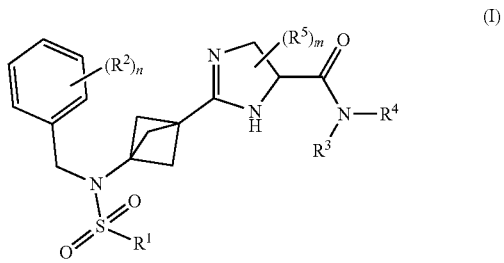

or a tautomeric or a stereochemically isomeric form, a pharmaceutically acceptable salt or a solvate thereof, wherein:

$R^1$ represents $C_{1-6}$ alkyl, $C_{1-6}$ alkoxy, $C_{1-6}$ alkanol, —X—$C_{3-8}$ cycloalkyl, halo$C_{1-6}$ alkyl, aryl, heterocyclyl or heteroaryl, wherein said cycloalkyl, aryl, heterocyclyl or heteroaryl groups may be optionally substituted by one or more (e.g. 1, 2, 3 or 4) $R^a$ groups;

$R^a$ represents $C_{1-6}$ alkyl, halogen, halo$C_{1-6}$ alkyl, hydroxy, cyano, nitro, oxo, $CONR^xR^y$ or $C_{3-8}$ cycloalkyl;

$R^x$ and $R^y$ independently represent hydrogen or $C_{1-6}$ alkyl;

X represents a bond, —$CH_2$— or —$(CH_2)_2$—;

$R^2$ represents halogen, halo$C_{1-6}$ alkyl or cyano;

n represents an integer selected from 0 to 4;

$R^3$ represents hydrogen, $C_{1-6}$ alkyl, —X—$C_{3-8}$ cycloalkyl, halo$C_{1-6}$ alkyl or —X-aryl, wherein said alkyl may be optionally substituted by one or more cycloalkyl groups, wherein said cycloalkyl may be optionally substituted by one or more $C_{1-6}$ alkyl, $C_{1-6}$ alkoxy, halo$C_{1-6}$ alkyl, halogen, hydroxy or cyano groups, wherein said haloalkyl may be optionally substituted by one or more hydroxy groups, wherein said aryl may be optionally substituted by one or more halogen groups, wherein $R^3$ and $R^4$ together with the nitrogen atom to which they are attached may join to form a heterocyclyl ring optionally substituted by one or more $C_{1-6}$ alkyl, halo$C_{1-6}$ alkyl, or halogen;

$R^4$ represents hydrogen, $C_{1-6}$ alkyl or $C_{3-8}$ cycloalkyl;

$R^5$ represents $C_{1-6}$ alkyl or —X-aryl; and m represents an integer selected from 0 to 4, such that when m represents 2, said $R^5$ groups may join to form a $C_{3-8}$ cycloalkyl group.

DETAILED DESCRIPTION OF THE INVENTION

Definitions

The term 'halo' or 'halogen' as used herein refers to fluorine, chlorine, bromine or iodine.

The term 'cyano' as used herein refers to a group where a carbon atom is triple bonded to a nitrogen atom.

The term '$C_{1-6}$ alkyl' as used herein as a group or part of a group refers to a linear or branched saturated hydrocarbon group containing from 1 to 6 carbon atoms. Examples of such groups include methyl, ethyl, n-propyl, iso-propyl, butyl, iso-butyl, tert-butyl, pentyl, hexyl and the like.

The term '$C_{1-6}$ alkoxy' as used herein as a group or part of a group refers to a $C_{1-6}$ alkyl group which contains one or more oxygen atoms wherein $C_{1-6}$ alkyl is as defined herein. Examples of such groups include methoxy, ethoxy or propoxy.

The term 'haloC$_{1-6}$ alkyl' as used herein as a group or part of a group refers to a C$_{1-6}$ alkyl group as defined herein wherein one or more than one hydrogen atom is replaced with a halogen. The term 'haloC$_{1-6}$ alkyl' therefore includes monohaloC$_{1-6}$ alkyl and also polyhaloC$_{1-6}$ alkyl. There may be one, two, three or more hydrogen atoms replaced with a halogen, so the haloC$_{1-6}$ alkyl may have one, two, three or more halogens. Examples of such groups include fluoroethyl, fluoromethyl, trifluoromethyl or trifluoroethyl and the like.

The term 'oxo' as used herein refers to the group =O.

The term 'nitro' as used herein refers to the group —N(=O)$_2$.

The term 'hydroxy' or 'hydroxyl' as used herein refers to the group OH.

The term "C$_{1-6}$ alkanol" as used herein as a group or part of a group refers to a C$_{1-6}$ alkyl group which contains a hydroxyl group wherein C$_{1-6}$ alkyl is as defined herein. An example of a C$_{1-6}$ alkanol group includes —CH$_2$OH.

The term "C$_{3-8}$ cycloalkyl" as used herein refers to a saturated monocyclic hydrocarbon ring of 3 to 8 carbon atoms. Examples of such groups include cyclopropyl, cyclobutyl, cyclopentyl, cyclohexyl, cycloheptyl, cyclooctyl and the like.

The term 'aryl' as used herein refers to a carbocyclic monocyclic or bicyclic aromatic, unsaturated ring system containing for example 3 to 12 ring members. Examples of aryl rings include phenyl and naphthyl.

The term 'heteroaryl' as used herein refers to a monocyclic or bicyclic aromatic, unsaturated ring system containing for example 3 to 12 ring members. Each ring may contain up to five heteroatoms typically selected from nitrogen, sulfur and oxygen. Typically the heteroaryl ring will contain up to 4 heteroatoms, more typically up to 3 heteroatoms, more usually up to 2, for example a single heteroatom.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiophene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

The term 'heterocyclyl' as used herein refers to a monocyclic or bicyclic non-aromatic, partially saturated or fully saturated ring system containing for example 3 to 12 ring members. Each ring may contain up to five heteroatoms typically selected from nitrogen, sulfur and oxygen.

Particular examples of 'heterocyclyl' include morpholine, piperidine (e.g. piperidin-1-yl, piperidin-2-yl, piperidin-3-yl and piperidin-4-yl), piperidinone, pyrrolidine (e.g. pyrrolidin-1-yl, pyrrolidin-2-yl and pyrrolidin-3-yl), pyrrolidone, azetidine, pyran (2H-pyran or 4H-pyran), dihydrothiophene, oxetanyl, dihydropyran, dihydrofuran, dihydrothiazole, tetrahydrofuran, tetrahydrothiophene, dioxane, tetrahydropyran (e.g. tetrahydropyran-4-yl), imidazoline, imidazolidinone, oxazoline, thiazoline, pyrazolin-2-yl, pyrazolidine, piperazinone and piperazine.

It will be appreciated that the term 'heterocyclyl' includes reference to spiro and bridged heterocyclic derivatives. Examples of such spiro and bridged heterocyclic derivatives include: 1-azaspiro[3.3]heptyl, 5-azaspiro[2.4]heptyl, 5-azaspiro[3.4]octyl, 8-azabicyclo[3.2.1]octyl, 3-azabicyclo[3.1.0]hexyl, octahydrocyclopenta[c]pyrrolyl, 2-azaspiro[3.3]heptyl, 3-azabicyclo[3.2.1]octyl, 6-azaspiro[3.4]octyl, 5-azaspiro[2.5]octyl or 2-oxa-6-azaspiro[3.4]octyl, hexahydropyrrolo[2,3-c]pyrrolidinyl, oxaspiro[3.3]heptanyl, diazaspiro[3.4]octanyl, diazaspiro[4.4]nonyl, oxa-azaspiro[3.4]octanyl, oxa-azaspiro[4.4]nonyl, tetrahydrofuro[3,4-c]pyrrolidinyl, oxa-azaspiro[3.3]heptyl, diazaspiro[4.5]decanyl, diazaspiro[3.4]octanyl, octahydro-naphthyridinyl, tetrahydropyrazino-oxazinyl, oxadiazospiro[5.5]undecanyl and oxabicyclo[2.2.1]heptanyl.

The term 'optionally substituted' as used herein refers to a group which may be substituted or unsubstituted by a substituent as herein defined.

Embodiments

In one embodiment, $R^1$ represents:
- $C_{1-6}$ alkyl (such as methyl, ethyl, n-propyl, i-propyl, n-butyl, i-butyl, t-butyl, n-pentyl or i-pentyl);
- $C_{1-6}$ alkoxy (such as propoxy);
- —X—$C_{3-8}$ cycloalkyl (such as —(CH$_2$)-cyclopropyl, —(CH$_2$)$_2$-cyclopropyl, -cyclobutyl, —(CH$_2$)-cyclobutyl, -cyclopentyl or -cyclohexyl);
- halo$C_{1-6}$ alkyl (such as trifluoromethyl, fluoropropyl, difluoropropyl, trifluoropropyl, fluorobutyl, difluorobutyl or trifluorobutyl);
- aryl (such as phenyl);
- heterocyclyl (such as pyrrolidinyl or tetrahydropyranyl); or
- heteroaryl (such as furanyl, thiophenyl, pyrazolyl, pyridinyl or imidazolyl);

wherein said cycloalkyl, aryl, heterocyclyl or heteroaryl groups may be optionally substituted by one or more (e.g. 1, 2, 3 or 4) $R^a$ groups.

In a further embodiment, $R^1$ represents:
- halo$C_{1-6}$ alkyl (such as trifluoromethyl, fluoropropyl, difluoropropyl, trifluoropropyl, fluorobutyl, difluorobutyl or trifluorobutyl);
- aryl (such as phenyl); or
- heteroaryl (such as furanyl, thiophenyl, pyrazolyl, pyridinyl or imidazolyl);

wherein said aryl or heteroaryl groups may be optionally substituted by one or more (e.g. 1, 2, 3 or 4) $R^a$ groups.

In a further embodiment, $R^1$ represents:
- heteroaryl (such as pyridinyl);

wherein said heteroaryl groups may be optionally substituted by one or more (e.g. 1, 2, 3 or 4) $R^a$ groups.

In a yet further embodiment, $R^1$ represents:
- halo$C_{1-6}$ alkyl (such as fluoropropyl);
- aryl (such as phenyl, in particular unsubstituted phenyl); or
- heteroaryl (such as pyridinyl, in particular unsubstituted pyridyl).

In one embodiment, $R^a$ represents $C_{1-6}$ alkyl (such as methyl), halogen (such as fluorine or chlorine), halo$C_{1-6}$ alkyl (such as trifluoromethyl), hydroxy, cyano, nitro, oxo, CONR$^x$R$^y$ (such as CONH$_2$) or $C_{3-8}$ cycloalkyl (such as cyclopropyl).

In one embodiment, $R^2$ represents halogen (such as fluorine or chlorine), halo$C_{1-6}$ alkyl (such as difluoromethyl or trifluoromethyl) or cyano. In a further embodiment, $R^2$ represents halogen (such as fluorine or chlorine).

In one embodiment, n represents an integer selected from 0 to 3.

In a further embodiment, n represents 0.

In a yet further embodiment, n represents 1 or 2.

In an alternative embodiment, n represents 1 and $R^2$ represents halogen (such as fluorine or chlorine), halo$C_{1-6}$ alkyl (such as difluoromethyl or trifluoromethyl) or cyano. In a further embodiment, n represents 1 and $R^2$ represents 3-fluorine, 4-fluorine, 3-chlorine, 4-chlorine, 4-difluoromethyl, 4-trifluoromethyl or 4-cyano. In a yet further embodiment, n represents 1 and $R^2$ represents 4-chlorine.

In an alternative embodiment, n represents 2 and $R^2$ represents halogen (such as fluorine or chlorine), halo$C_{1-6}$ alkyl (such as trifluoromethyl) or cyano. In a further embodiment, n represents 2 and $R^2$ represents: 2-fluoro, 4-chloro; 3-fluoro, 4-chloro; 3-chloro, 4-fluoro; 3-fluoro, 4-trifluoromethyl; 3-chloro, 4-trifluoromethyl; 3-cyano, 4-chloro; 3,4-difluoro; or 3,4-dichloro. In a yet further embodiment, n represents 2 and $R^2$ represents 3-fluoro, 4-chloro.

In an alternative embodiment, n represents 3 and $R^2$ represents halogen (such as fluorine or chlorine). In a further embodiment, n represents 3 and $R^2$ represents 3,5-difluoro, 4-chloro.

In one embodiment, $R^3$ represents:
- hydrogen;
- $C_{1-6}$ alkyl (such as methyl, n-propyl, i-propyl, dimethylpropyl, n-butyl or t-butyl) optionally substituted by one or more cycloalkyl groups (such as cyclopropyl);
- —X—$C_{3-8}$ cycloalkyl (such as cyclopropyl, —CH$_2$-cyclopropyl, —(CH$_2$)$_2$-cyclopropyl, -cyclobutyl, —CH$_2$-cyclobutyl, —(CH$_2$)$_2$-cyclobutyl, —C(H)(CH$_3$)-cyclobutyl, cyclohexyl, —CH$_2$— cyclohexyl or bicyclo[1.1.1]pentanyl optionally substituted by one or more $C_{1-6}$ alkyl (such as methyl), $C_{1-6}$ alkoxy (such as methoxy), halo$C_{1-6}$ alkyl (such as difluoromethyl, trifluoromethyl or trifluoroethyl), halogen (such as fluorine), hydroxy or cyano groups;
- halo$C_{1-6}$ alkyl (such as trifluoroethyl, difluoropropyl, trifluoropropyl, pentafluoropropyl, fluorobutyl, trifluorobutyl or trifluoropentyl) optionally substituted by one or more hydroxy groups;
- —X-aryl (such as -phenyl or —CH$_2$-phenyl) optionally substituted by one or more halogen (such as fluorine) groups;
- or $R^3$ and $R^4$ together with the nitrogen atom to which they are attached join to form a heterocyclyl ring (such as azetidinyl, pyrrolidinyl, piperidinyl, morpholinyl, azepinyl, 1-azaspiro[3.3]heptyl, 5-azaspiro[2.4]heptyl, 5-azaspiro[3.4]octyl, 8-azabicyclo[3.2.1]octyl, 3-azabicyclo[3.1.0]hexyl, octahydrocyclopenta[c]pyrrolyl, 2-azaspiro[3.3]heptyl, 3-azabicyclo[3.2.1]octyl, 6-azaspiro[3.4]octyl, 5-azaspiro[2.5]octyl or 2-oxa-6-azaspiro[3.4]octyl) optionally substituted by one or more $C_{1-6}$ alkyl (such as methyl), halo$C_{1-6}$ alkyl (such as difluoromethyl or trifluoromethyl) or halogen (such as fluorine).

In a further embodiment, $R^3$ represents:
- —X—$C_{3-8}$ cycloalkyl (such as cyclopropyl, —CH$_2$-cyclopropyl, —(CH$_2$)$_2$-cyclopropyl, -cyclobutyl, —CH$_2$-cyclobutyl, —(CH$_2$)$_2$-cyclobutyl, —C(H)(CH$_3$)-cyclobutyl, cyclohexyl, —CH$_2$— cyclohexyl or bicyclo[1.1.1]pentanyl) optionally substituted by one or more $C_{1-6}$ alkyl (such as methyl), $C_{1-6}$ alkoxy (such as methoxy), halo$C_{1-6}$ alkyl (such as difluoromethyl, trifluoromethyl or trifluoroethyl), halogen (such as fluorine), hydroxy or cyano groups; or
- halo$C_{1-6}$ alkyl (such as trifluoroethyl, difluoropropyl, trifluoropropyl, pentafluoropropyl, fluorobutyl, trifluorobutyl or trifluoropentyl) optionally substituted by one or more hydroxy groups.

In a yet further embodiment, $R^3$ represents:
- —X—$C_{3-8}$ cycloalkyl (such as bicyclo[1.1.1]pentanyl, in particular unsubstituted bicyclo[1.1.1]pentanyl; or
- halo$C_{1-6}$ alkyl (such as trifluoropropyl, in particular unsubstituted trifluoropropyl).

In one embodiment, $R^4$ represents hydrogen, $C_{1-6}$ alkyl (such as methyl or ethyl) or $C_{3-8}$ cycloalkyl (such as cyclopropyl). In a further embodiment, $R^4$ represents hydrogen.

In one embodiment, m represents an integer selected from 0 to 3.

In one embodiment, $R^5$ represents $C_{1-6}$ alkyl (such as methyl, ethyl, n-propyl, i-propyl or i-butyl) or —X-aryl (such as —CH$_2$-phenyl) or m represents 2 and said two R$^5$ groups join to form a C$_{3-8}$ cycloalkyl group (such as cyclopropyl or cyclobutyl). In a further embodiment, R$^5$ represents C$_{1-6}$ alkyl (such as methyl, ethyl, n-propyl, i-propyl or i-butyl). In a yet further embodiment, R$^5$ represents C$_{1-6}$ alkyl (such as methyl).

In one embodiment, m represents 0.

In a further embodiment, m represents 2.

In an alternative embodiment, m represents 1 and R$^5$ represents C$_{1-6}$ alkyl (such as methyl, n-propyl, i-propyl or i-butyl) or —X-aryl (such as —CH$_2$-phenyl).

In an alternative embodiment, m represents 2 and R$^5$ represents C$_{1-6}$ alkyl (such as methyl or ethyl) or said two R$^5$ groups join to form a C$_{3-8}$ cycloalkyl group (such as cyclopropyl or cyclobutyl).

In a further embodiment, m represents 2 and R$^5$ represents C$_{1-6}$ alkyl (such as methyl or ethyl). In a yet further embodiment, m represents 2 and R$^5$ represents C$_{1-6}$ alkyl (such as methyl).

In an alternative embodiment, m represents 3 and R$^5$ represents C$_{1-6}$ alkyl (such as methyl).

In one embodiment, the invention provides a compound of formula (I) which is the free base of a compound of Examples 1-295 or a pharmaceutically acceptable salt or solvate thereof.

In one embodiment, the invention provides a compound of formula (I) which is the free base of a compound of Example 1, Example 48 or Example 92 or a pharmaceutically acceptable salt or solvate thereof.

A reference to a compound of the formula (I) and subgroups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, prodrugs, isotopes and protected forms thereof as defined in any aspect of the invention (except intermediate compounds in chemical processes) are referred to as "compounds of the invention".

Salts

Certain compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (-)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pK$_a$ of the acid from which the salt is formed.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse, *J. Pharm. Sci.* 1977, 66, pp. 1-19. Such pharmaceutically acceptable salts include acid addition salts formed with inorganic acids e.g. hydrochloric, hydrobromic, sulfuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates may be used, for example in the isolation of compounds of formula (I) and are included within the scope of this invention. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Certain of the compounds of formula (I) may form acid addition salts with one or more equivalents of the acid. The present invention includes within its scope all possible stoichiometric and non-stoichiometric forms.

Solvates

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention. In one embodiment, the pharmaceutically acceptable solvates of the compounds of the invention include the hydrate thereof.

It will be understood that the invention includes pharmaceutically acceptable derivatives of compounds of formula (I) and that these are included within the scope of the invention.

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof.

N-Oxides

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience. More particularly, N-oxides can be made by the procedure of L. W. Deady (*Syn. Commun.* 1977, 7, 509-514) in which the amine compound is reacted with m-chloroperoxybenzoic acid (mCPBA), for example, in an inert solvent such as dichloromethane.

Prodrugs

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, 19, 9, 1983, 499-538 and in *Topics in Chemistry*, Chapter 31, pp. 306-316 and in "*Design of Prodrugs*" by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "*Design of Prodrugs*" (the disclosure in which document is incorporated herein by reference) may be placed on appropriate functionalities when such functionalities are present within compounds of the invention.

Also included within the scope of the compound and various salts of the invention are polymorphs thereof.

Enantiomers

The compounds of formula (I) may be achiral or R or S enantiomers. Where additional chiral centres are present in compounds of formula (I), the present invention includes within its scope all possible enantiomers and diastereoisomers, including mixtures thereof. The different isomeric forms may be separated or resolved one from the other by conventional methods, or any given isomer may be obtained by conventional synthetic methods or by stereospecific or asymmetric syntheses. The invention also extends to any tautomeric forms or mixtures thereof.

Isotopes

The subject invention also includes all pharmaceutically acceptable isotopically-labelled compounds which are identical to those recited in formula (I) but for the fact that one or more atoms are replaced by an atom having an atomic mass or mass number different from the atomic mass or mass number most commonly found in nature.

Examples of isotopes suitable for inclusion in the compounds of the invention comprise isotopes of hydrogen, such as $^{2}H$ (D) and $^{3}H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase) etc. The radioactive isotopes tritium, i.e. $^{3}H$ (T), and carbon-14, i.e. $^{14}C$, are particularly useful for this purpose in view of their ease of incorporation and ready means of detection.

Substitution with heavier isotopes such as deuterium, i.e. $^{2}H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labelled compounds of formula (I) can generally be prepared by conventional techniques known to those skilled in the art or by processes analogous to those described in the accompanying Examples and Preparations using appropriate isotopically-labelled reagents in place of the non-labelled reagent previously employed.

Purity

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are given on a weight for weight basis). Impure preparations of the compounds may be used for preparing the more pure forms used in the pharmaceutical compositions.

Processes

According to a further aspect of the present invention there is provided a process for the preparation of compounds of formula (I) and derivatives thereof. The following schemes are examples of synthetic schemes that may be used to synthesise the compounds of the invention. In the following schemes reactive groups can be protected with protecting groups and de-protected according to well established techniques.

According to a further aspect of the invention there is provided a process for preparing a compound of formula (I) as herein defined which comprises:

(a) reacting a compound of formula (II):

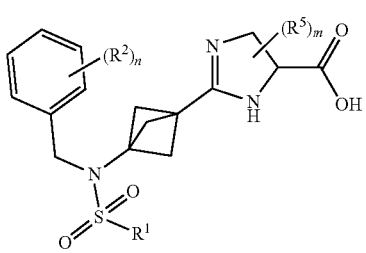

wherein $R^1$, $R^2$, n, $R^5$ and m are as defined herein, with a compound of formula $HNR^3R^4$;

(b) deprotection of a protected derivative of a compound of formula (I);
(c) interconversion of a compound of formula (I) or protected derivative thereof to a further compound of formula (I) or protected derivative thereof; and
(d) optional formation of a pharmaceutically acceptable salt of a compound of formula (I).

Process (a) typically comprises dissolving a compound of formula (II) in suitable reagents, such as MeCN and DIEA, followed by addition of a compound of formula $HNR^3R^4$ in the presence of a suitable reagent such as COMU.

Compounds of formula (II) may be prepared in accordance with the Schemes and experimental procedures provided in Examples 1 to 5 herein.

Compounds of formula $HNR^3R^4$ are either known or may be prepared in accordance with known procedures.

A wide range of well known functional group interconversions for process (c) are known by a person skilled in the art for converting a precursor compound to a compound of formula (I) and are described in Advanced Organic Chemistry by Jerry March, $4^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions described herein are followed or preceded by one or more reactions known to the skilled of the art and are performed in an appropriate order to achieve the requisite substitutions on $R^1$, $R^2$, $R^3$, $R^4$ and $R^5$ defined herein to afford other compounds of formula (I). Non-limiting examples of such reactions whose conditions can be found in the literature include:

protection of reactive functions,
deprotection of reactive functions,
halogenation,
dehalogenation,
dealkylation,
alkylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of esters groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

It is recognised that the sequence of reactions involving aryl coupling and reduction may be varied. It is also recognised that a wide range of palladium based catalysts are suitable for conducting aryl coupling reactions.

It may also be recognised that isomer separation may occur at any suitable stage in the synthetic sequence. It should be stressed that such chiral separation forms a key aspect of the invention and that such separation may be conducted in accordance with the methodology described herein or may be conducted in accordance with known methodology.

It is also recognised that it may be beneficial to temporarily form a protected derivative of an intermediate in the synthesis, for example, a Boc-protected amine, or SEM-protected amide, in order to facilitate chromatographic separation, chiral resolution or to give improved solubility or yields in particular steps.

In many of the reactions described above, it may be necessary to protect one or more groups to prevent reaction from taking place at an undesirable location on the molecule. Examples of protecting groups, and methods of protecting and de-protecting functional groups, can be found in Protective Groups in Organic Synthesis (T. Green and P. Wuts; 4th Edition; John Wiley and Sons, 2007).

A hydroxy group may be protected, for example, as an ether (—OR) or an ester (—OC(=O)R), for example, as: a tert-butyl ether; a tetrahydropyranyl (THP) ether; a benzyl, benzhydryl (diphenylmethyl), or trityl (triphenylmethyl) ether; a trimethylsilyl or tert-butyldimethylsilyl ether; or an acetyl ester (—OC(=O)CH$_3$).

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a tert-butyl carbamate (—NHCOOC(CH$_3$)$_3$, NH-Boc); a 2-biphenyl-2-propyl carbamate (—NHCO—OC(CH$_3$)$_2$C$_6$H$_4$C$_6$H$_5$, NH-Boc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH-Psec).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an $C_{1-7}$ alkyl ester (e.g. a methyl ester; a tert-butyl ester); a $C_{1-7}$ haloalkyl ester (e.g. a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester; para-methoxybenzyl ester.

It will be understood by those skilled in the art that certain compounds of the invention can be converted into other compounds of the invention according to standard chemical methods.

Pharmaceutically acceptable salts may be prepared conventionally by reaction with the appropriate acid or acid derivative.

Therapeutic Utility

The compounds of the invention, subgroups and examples thereof, are potassium channel inhibitors, and which may be useful in preventing or treating disease states or conditions described herein. In addition, the compounds of the invention, and subgroups thereof, will be useful in preventing or treating diseases or condition mediated by potassium channel inhibition, in particular inhibition of the potassium channel Kv1.3.

Examples of diseases or conditions mediated by potassium channel inhibition include: autoimmune, inflammatory, cardiovascular, neuronal, auditory, renal and metabolic mediated diseases.

Thus, according to a further aspect of the invention there is a provided a compound of formula (I) as defined herein for use in therapy.

According to a further aspect of the invention there is provided a compound of formula (I) as defined herein for use in preventing or treating diseases or condition mediated by potassium channel inhibition, in particular inhibition of the potassium channel Kv1.3.

According to a further aspect of the invention there is provided the use of a compound of formula (I) as defined herein in the manufacture of a medicament for preventing or treating diseases or condition mediated by potassium channel inhibition, in particular inhibition of the potassium channel Kv1.3.

According to a further aspect of the invention there is provided a compound of formula (I) as defined herein for use in preventing or treating autoimmune, inflammatory, cardiovascular, neuronal, auditory, renal and metabolic mediated diseases.

According to a further aspect of the invention there is provided the use of a compound of formula (I) as defined herein in the manufacture of a medicament for preventing or treating autoimmune, inflammatory, cardiovascular, neuronal, auditory, renal and metabolic mediated diseases.

The compounds of the present invention may be useful for the treatment of the adult population. The compounds of the present invention may be useful for the treatment of the pediatric population.

Examples of autoimmune disorders include: rheumatoid arthritis and multiple sclerosis.

One particular example of cardiovascular diseases includes arrhymias.

Examples of specific diseases or conditions mediated by potassium channels, such as Kv1.3 include: psoriasis, psoriatric arthritis, autoimmune thyroiditis, Hashimoto's disease, Grave's disease, rheumatoid arthritis, vitiligo, Crohn's disease, ulcerative colitis, inflammatory bowel disease, ankylosing spondylitis (Morbus Bechterew), periodontal disease, diabetes type 1, multiple sclerosis, systemic lupus erythematosus, anti-glomerular basement membrane glomerulonephritis, rapidly progressive glomerulonephritis, advanced chronic renal failure, chronic kidney disease, renal fibrosis, uveitis, pars planitis, asthma, *Pemphigus foliaceus*, inclusion body myositis, dermatomyositis, scleroderma, Behcet disease, atopic dermatitis, allergic and irritant contact dermatitis, Lichen planus, Sjogren's syndrome, Graft-versus-Host-Reaction, Host-versus-Graft-Reaction, transplant rejection, end-stage renal disease, vascularized composite allotransplantation rejection, alopecia areata, inflammatory bone resorption disease, anti-neutrophil cytoplasmic autoantibody-associated vasculitis, osteoarthritis, diseases associated with intimal hyperplasia, breast cancer, leukemia, chronic lymphocytic leukemia, human lung adenocarcinoma, cutaneous T-cell lymphoma, osteosarcoma, neuroblastoma, ovarian cancer and melanoma, neuroinflammatory disorders, neurodegeneration, HIV-1-associated neurocognitive disorders (HAND), microglia-induced oxidative stress in Alzheimer's disease, obesity, and insulin resistance, restenosis/neointimal hyperplasia, atherosclerosis (arteriosclerotic vascular disease or ASVD), acute coronary syndrome, acute ischemic stroke, hypertension.

In one embodiment, the disease or condition mediated by potassium channels, such as Kv1.3 includes: psoriasis, rheumatoid arthritis, diabetes type I, multiple sclerosis, anti-glomerular basement membrane glomerulonephritis, rapidly progressive glomerulonephritis, advanced chronic renal failure, chronic kidney disease, renal fibrosis, allergic and irritant contact dermatitis, transplant rejection, asthma, end-stage renal disease, vascularized composite allotransplantation rejection, alopecia areata, inflammatory bone resorption disease, human lung adenocarcinoma, melanoma, neuroinflammatory disorders, neurodegeneration, obesity, and insulin resistance, restenosis/neointimal hyperplasia, atherosclerosis (arteriosclerotic vascular disease or ASVD) and acute coronary syndrome.

In a further embodiment, the disease or condition mediated by potassium channels, such as Kv1.3 includes: psoriasis, atopic dermatitis, allergic and irritant contact dermatitis, rheumatoid arthritis, uveitis and multiple sclerosis, such as atopic dermatitis, allergic and irritant contact dermatitis, rheumatoid arthritis, uveitis and multiple sclerosis.

In one embodiment, the disease or condition mediated by potassium channels, such as Kv1.3, is one which requires an antiproliferative response, such as breast cancer, ovarian cancer, leukemia, chronic lymphocytic leukemia, osteosarcoma, neuroblastoma, human lung adenocarcinoma, melanoma, restenosis and neointimal hyperplasia.

In one embodiment, the disease or condition mediated by potassium channels, such as Kv1.3, is one which requires a neuroprotective response, such as neurodegeneration.

In one embodiment, the disease or condition mediated by potassium channels, such as Kv1.3, is one which requires modulation of cellular metabolism, such as obesity and insulin resistance.

In one embodiment, the disease or condition mediated by potassium channels, such as Kv1.3, is one which is treatable by inhibition of $Kv1.3^{high}$ phenotype cells, particularly $Kv1.3^{high}$ phenotype immune system cells, more particularly class-switched memory B-cells and/or effector memory T-cells of the $Kv1.3^{high}$ phenotype, even more particularly T-cell driven autoimmune disorders and chronic inflammation conditions, in particular selected from the group consisting of psoriatic arthritis, Type 1 diabetes, rheumatoid arthritis, multiple sclerosis, psoriasis, asthma, anti-glomerular basement membrane glomerulonephritis, acute coronary syndrome.

It will be appreciated that $Kv1.3^{high}$ phenotype cells are cells wherein Kv1.3 expression numbers range from 750 to 2900, particularly 950 to 2900 Kv1.3 channels per cell, which can be determined either by immunohistochemical staining or patch-clamp analysis well known to the skilled person, and for example described in Wulff et al. (2003) J. Clin. Invest. 111, 1703; Rus et al (2005) PNAS 102, 11094.

It will be apparent to the skilled person that analysis of whether Kv1.3 expression in cells of a subject is high as defined herein, can particularly be determined by:
 (a) obtaining a sample from said subject;
 (b) optionally isolating cells wherein Kv1.3 expression is to be determined from said sample;
 (c) optionally culturing said cells in a suitable medium; and (d) determining the Kv1.3 expression in said cells.

In one embodiment, said sample is a fluid sample, particularly a synovial or cerebrospinal fluid sample, leukapheresis sample, or peripheral blood sample, e.g. from a subject suspected of suffering from rheumatoid arthritis, or a tissue sample, particularly a sample from the affected tissue, such as a psoriatic lesion, synovial tissue or brain infiltrate, from said subject.

In one embodiment, said cells wherein Kv1.3 expression is to be determined may be selected from: lymphocytes, B-cells, or T-cells, such as TEM cells; $CD4^+$ T-cells or $CD8^+$ T-cells.

In one embodiment, said cells wherein Kv1.3 expression is to be determined are isolated by techniques known in the art, particularly density gradient centrifugation and FACS (fluorescence activated cell sorting), wherein in particular such isolation is used in the case of fluid samples.

In one embodiment, said suitable medium is known in the art, e.g. Dulbecco's media, such as Iscove's modified Dulbecco's medium, which may be supplemented with the necessary additives, such as antibiotics.

In the embodiment wherein the sample comprises tissue samples, the isolation and culturing may in certain cases be replaced by a step of sample preparation, e.g. paraffin preparation.

It will be appreciated that the Kv1.3 expression in said cells is determined via art-known techniques, particularly by patch-clamp, such as the patch-clamp techniques referenced herein, or by subjecting said cells to immunohistochemical staining and determining Kv1.3 expression by fluorescence microscopy, such as described in the literature references included herein, wherein the corresponding Kv1.3 expression in said cells may be calculated from the results obtained by the aforementioned techniques via art-known methods, such as described in the literature references cited herein. Examples of such methods are described in e.g. PNAS 2006, 103, 17414; J. Clin. Invest. 2003, 111, 1703; J. Invest. Dermatol. 2011, 131, 118; PNAS 2005, 102, 11094.

Pharmaceutical Compositions

While it is possible for the active compound to be administered alone, it is preferable to present it as a pharmaceutical composition (e.g. formulation). In one embodiment this is a sterile pharmaceutical composition.

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one particular embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another particular embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract. Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Particularly, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, particularly from approximately 20% to approximately 90%, active ingredient. Pharmaceutical compositions according to the invention may be, for example, in unit dose form, such as in the form of ampoules, vials, suppositories, pre-filled syringes, dragees, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by potassium channel inhibition, in particular inhibition of the potassium channel Kv1.3. Thus, according to a further aspect of the invention there is provided a method of treating a disease state or condition mediated by potassium channel inhibition (e.g. Kv1.3) which comprises administering to a subject in need thereof a compound of formula (I) as described herein. Examples of such disease states and conditions are set out above, and in particular include autoimmune, inflammatory, cardiovascular, neuronal, auditory, renal and metabolic mediated diseases.

The compounds are generally administered to a subject in need of such administration, for example a human or animal patient, particularly a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

In another particular dosing schedule, a patient is given the compound orally once a week.

In another particular dosing schedule, a patient is given the compound orally once-daily for between 7 and 28 days such as 7, 14 or 28 days.

In another particular dosing schedule, a patient is given the compound orally once-daily for 1 day, 2 days, 3 days, 5 days or 1 week followed by the required amount of days off to complete a one or two week cycle.

In another particular dosing schedule, a patient is given the compound orally once-daily for 2 weeks followed by 2 weeks off.

In another particular dosing schedule, a patient is given the compound orally once-daily for 2 weeks followed by 1 week off.

In another particular dosing schedule, a patient is given the compound orally once-daily for 1 week followed by 1 week off.

Ultimately, however, the quantity of compound administered and the type of composition used will be commensurate with the nature of the disease or physiological condition being treated and will be at the discretion of the physician.

It will be appreciated that potassium channel inhibitors can be used as a single agent or in combination with other therapeutically active agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example autoimmune, inflammatory, cardiovascular, neuronal, auditory, renal and metabolic mediated diseases. For the treatment of the above conditions, the compounds of the invention may be advantageously employed in combination with one or more other therapeutically agents which support the therapy of the disease being treated.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen.

Where the compound of the formula (I) is administered in combination therapy with one, two, three, four or more other therapeutic agents (particularly one or two, more particularly one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

In one embodiment is provided a compound of formula (I) for the manufacture of a medicament for use in therapy wherein said compound is used in combination with one, two, three, or four other therapeutic agents. In another embodiment is provided a medicament for treating autoimmune, inflammatory, cardiovascular, neuronal, auditory, renal and metabolic mediated diseases which comprises a compound of formula (I) wherein said medicament is used in combination with one, two, three, or four other therapeutic agents.

It will be appreciated that the particular method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other therapeutic agent(s) when given as a combination may be determined by the person skilled in the art. Said ratio and the exact dosage and frequency of administration depends on the particular compound according to the invention and the other therapeutic agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another therapeutic agent may range from 1/10 to 10/1, more in particular from 1/5 to 5/1, even more in particular from 1/3 to 3/1.

In one embodiment the pharmaceutical composition comprises a compound of formula (I) together with a pharmaceutically acceptable carrier and optionally one or more therapeutic agent(s).

In another embodiment the invention relates to the use of a combination according to the invention in the manufacture of a pharmaceutical composition for preventing or treating autoimmune, inflammatory, cardiovascular, neuronal, auditory, renal and metabolic mediated diseases.

In a further embodiment the invention relates to a product containing a compound of formula (I) and one or more additional therapeutic agents, as a combined preparation for simultaneous, separate or sequential use in the treatment of patients suffering from autoimmune, inflammatory, cardiovascular, neuronal, auditory, renal and metabolic mediated diseases.

Examples of suitable additional therapeutic agents include: methotrexate, corticosteroids like prednisone, prednisolone, methylprednisolone, dexamethasone, betamethasone, cortisone and the like; mycophenolate mofetil, tacrolimus, leflunomide or teriflunomide, cyclosporine A, cyclophosphamide, mitoxanthrone, fingolimod, azathioprine, glatiramer acetate, dimethyl fumarate, an IK-1 inhibitor like TRAM-34, a JAK-inhibitor like Tofacitinib or braticinip, a SYK-inhibitor like Fostamatinib, interferon-beta (IFN-β).

Examples

The invention will now be illustrated, but not limited, by reference to the specific embodiments described in the following examples.

Synthesis of (2S)-3-methyl-3-nitro-2-{[(1 'S)-1'-phenylethyl]amino}butanoic acid (4)[1]

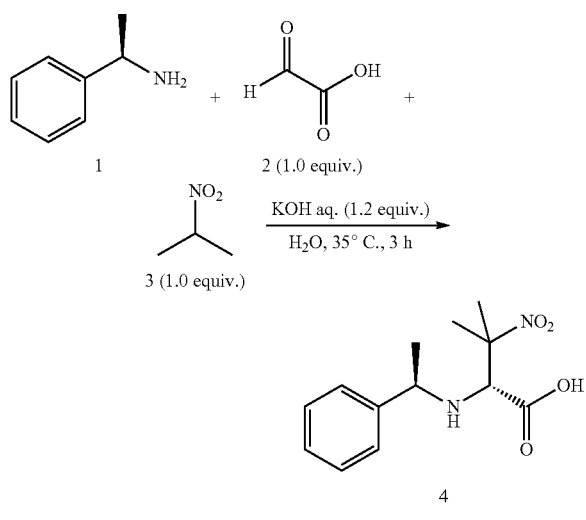

2-Nitropropane (3, 3.7 mL, 40 mol, 1.0 equiv) and water (40 mL) were placed under argon in a 500 mL flask with a stir bar, potassium hydroxide (2.7 g, 48 mmol, and 1.2 equiv) was added all at once. The flask was placed in a regulated oil bath heated to 45° C. (S)-(−)-α-Methylbenzylamine (1, 4.8 g, 40 mmol) was added quickly. The reaction mixture was maintained at ca. 45° C. and stirred swiftly as glyoxylic acid (2, 50% aq, 3.7 g, 40 mmol, 1.0 equiv.) was added slowly dropwise (60 min, slowest for the last one-third) via a syringe. The reaction mixture became cloudy, then clear, and when the solid began forming again the addition was slowed down. After completion of the addition, the reaction was stirred for an additional 3 h under argon at 35° C., and stirred swiftly as 3M aq hydrochloric acid (30.4 mL, 92 mmol) was added dropwise (over 30 min). The resulting thick off-white suspension was stirred for overnight at room temperature. The cooled suspension was filtered with suction filtration, and the filter cake was rinsed with diluted aqueous HCl, water and diethyl ether. The solid in the filter cake was dried by suction, and then dried under high vacuum for 3 h at 50° C. to got a slightly off-white power (5.4 g).

Purification of 3-methyl-3-nitro-(2(S)-(1(S)-phenyl-ethyl-amino))-butyric acid (4)[1]

3M HCl, water and acetic acid was placed in an Erlenmeyer flask and stirred well as it as immersed in a 60° C. bath and warmed to 40-50° C. When the solution was up to the temperature, dissolved 4 in the stirred warm DMSO solution (50° C., dry, 40 mL) and added 25 mL of acetic acid to form a clear solution, then added the warm DMSO solution to the Erlenmeyer at an even dropwise rat. The suspension was then filtered through paper by suction and ethyl ether. The filter cake was then suction to compact "dryness" over 30 min. The solids then transferred to room temperature and dried under full vacuum for 12 hours.

Second purification of 3-methyl-3-nitro-(2(S)-(1 (S)-phenylethyl-amino))-butyric acid (4) (Procedure is Similar to the First Precipitation Above)[1]

A solution of diluted aq hydrochloric acid, water and acetic acid was placed in a 1 L Erlenmeyer flask and stirred well as it was immersed in a 45-60° C. bath and warmed to 40° C. Another flask, to a solution of the 4 in anhydrous DMSO (40 mL) was added acetic acid. The mixture was then warmed to 50° C. and added dropwise to the Erlenmeyer flask. Upon complete addition, the suspension was stirred and placed in a 0° C. bath to cool room temperature. The suspension was then filtered through paper by suction and rinsed with dilute aq hydrochloric acid, water, isopropanol and diethyl ether. The filter cake was then suctioned to compact "dryness" over 30 min. The filtered was then transferred to room temperature vacuum and dried under full vacuum for 14 hours. After that, the solids was dried at 50° C. under high vacuum for 3 hours to yield 4 as white powder (1.4 g, 13.2% yield).

Synthesis of methyl (2S)-3-methyl-3-nitro-2-{[(1'S)-1'-phenylethyl]amino}butanoate (5)[1]

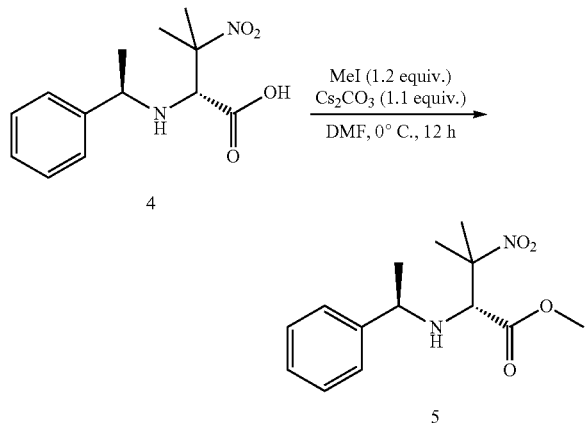

In an oven-dried 100 mL flask with a stir bar was charged with 4 (1.4 g, 5.3 mmol) and cesium carbonate (1.8 g, 5.6 mmol, 1.1 equiv) under argon with rapid string. Dimethylformamide (10 mL) was added rapidly and stirred for 10 min, with aid of sonication for 5 min. After the reaction mixture was cooled to 0° C., iodomethane (378.7 uL, 6.1 mmol, 1.2 equiv) was added dropwise over 15 min. The reaction mixture was stirred under argon and at 0° C. for 1 h then was allowed to warm to ambient temperature with stirring was continued for 12 h. The reaction was washed with EtOAc and water into a separatory funnel containing EtOAc, water and 3.0 M aq hydrochloric acid. The organic layer was separated. And the aqueous layer was adjusted pH to 7-8 and extracted with EtOAc. The combined organic phases were washed with 3% $Li_2SO_4$, half-saturated aq $NaHCO_3$ and brine and dried over anhydrous $Na_2SO_4$. The solvent was concentrated to give amber oil (1.5 g, quant.). The obtained 5 was used without further purification.

Synthesis of methyl (2S)-3-amino-3-methyl-2-{[(1'S)-1'-phenylethyl]amino}butanoate (6)[1]

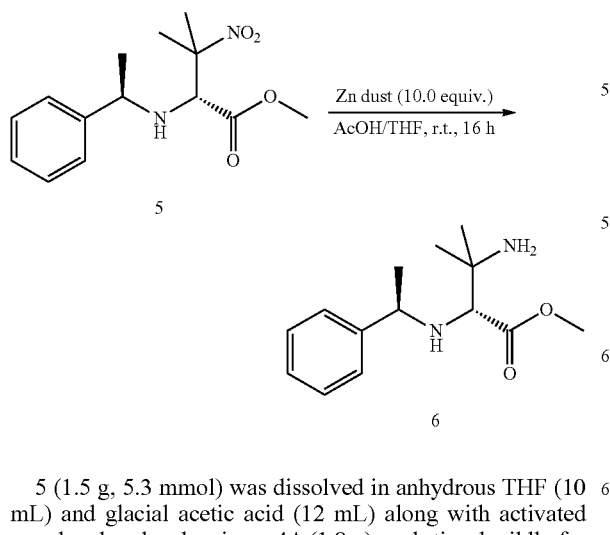

5 (1.5 g, 5.3 mmol) was dissolved in anhydrous THF (10 mL) and glacial acetic acid (12 mL) along with activated powdered molecular sieves 4A (1.8 g), and stirred mildly for 3 h under argon. The flask was then immersed in 0° C. bath and stirred well for 20 min. To the cold reaction mixture was added zinc dust (3.1 g, 52.9 mmol, 10.0 equiv). The mixture reaction was stirred at 0° C. for 2 h, and then allowed warm to ambient temperature with stirring continued for 16 h. The mixture was then diluted with THF and filtered through a celite pad with additional THF washing. The solution was rotary evaporated to yield a slightly yellow oily solid. This material was dissolved in 3:1 chloroform/isopropanol and EDTA solutions at pH 10.5-11.0. Additional 4M NaOH solutions are added in portions to reach pH=10.5-11.0. The funnel contents were thoroughly shaken, and the aqueous phase separated. The organic phase was then washed with EDTA pH=10.5-11.0, brine, dried over $Na_2SO_4$, filtered and evaporated under reduced pressure, followed with additional heptane and evaporation to yield a light-amber oil. The obtained 6 was used without further purification.

Synthesis of methyl(2S)-3-{[(tert-butoxy)carbonyl]amino}-3-methyl-2-{[(1'S)-1'-phenylethyl]amino}butanoate (7)[1]

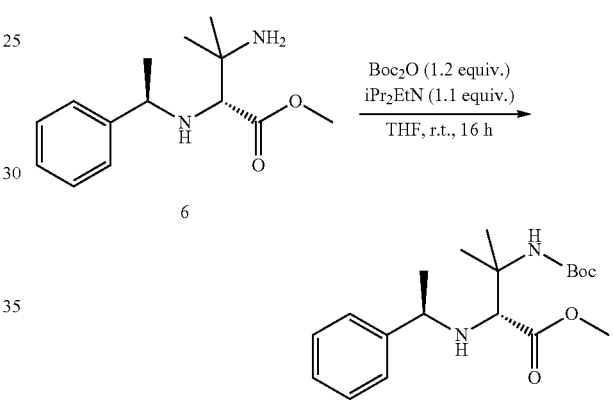

6 (5.3 mmol) was dissolved in anhydrous THF (10 mL) under argon, and diisopropylethylamine (1.0 mL, 5.8 mmol, 1.1 equiv) was added to this solution. tert-Butylpyrocarbonate (1.3 g, 5.9 mmol, 1.2 equiv) was added. After stirring at room temperature for 16 h, the reaction mixture was dissolved in EtOAc, and washed with water containing 1 eq HCl, half saturated $NaHCO_3$ solution, 14% $NH_4OH$, brine, dried over $Na_2SO_4$, filtered and contracted under reduced pressure to yield the BOC-diamino-ester residue, which was purified by CombiFlash (eluting with EtOAc in DCM 0-5%) to afford it as viscous oil (940.3 mg, 51% yield (3 steps)).

Synthesis of methyl (2S)-2-amino-3-{[(tert-butoxy)carbonyl]amino}-3-methylbutanoate (8)[1]

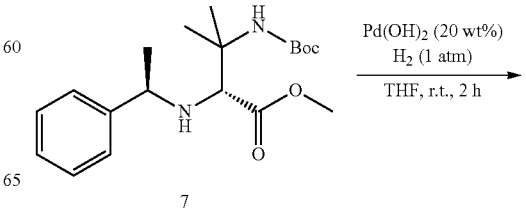

-continued

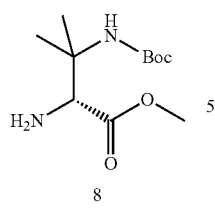

8

7 (0.6 g, 1.7 mmol) was dissolved in anhydrous THF (10 mL) in 50 mL flask and placed under argon. Palladium hydroxide catalyst (0.12 g, 20 wt %) was rapidly weight and added to the flask. The flask was then filled with hydrogen and refilled. After 2 h, LC/MS showed the reaction was completed. The mixture was filtered through a celite pad, and the filtrate was condensed to dryness. The residue was purified by CombiFlash (eluting with 0-5% MeOH in DCM) to afford 8 as white solid (451.7 mg, quant.)

Synthesis of methyl 3-(phenylsulfonamido)bicyclo[1.1.1]pentane-1-carboxylate (11)

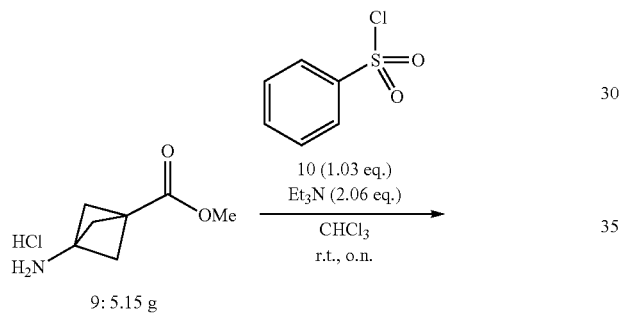

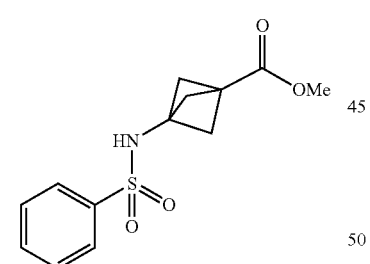

11: 9.1 g (crude, o.w.)

To a stirred solution of methyl 3-aminobicyclo[1.1.1]pentane-1-carboxylate hydrochloride (9, 5.15 g) and Et₃N (8.36 mL, 2.06 eq.) in CHCl₃ (60 mL), phenylsulfonyl chloride (10, 5.30 g, 1.03 eq.) was added at 0° C. The reaction mixture was stirred and warmed to ambient temperature for over night. After the reaction completion was checked by TLC, H₂O and 1N HCl was added to the reaction mixture, and the aqueous phase was extracted twice with AcOEt. The combined extract was dried over anhydrous Na₂SO₄, filtered and concentrated in vacuo to give methyl 3-(phenylsulfonamido)bicyclo[1.1.1]pentane-1-carboxylate (11, 9.07 g, overweight). The obtained 2 was used without further purification.

Synthesis of methyl 3-(N-(4-chloro-3-fluorobenzyl)phenylsulfonamido)bicyclo[1.1.1]pentane-1-carboxylate (13)

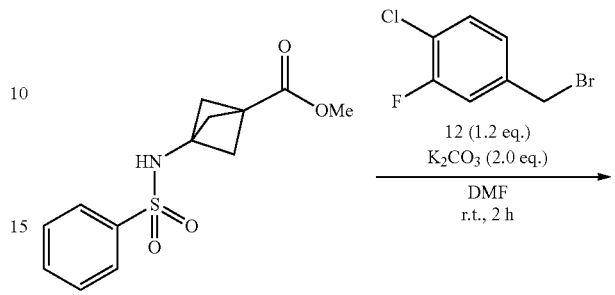

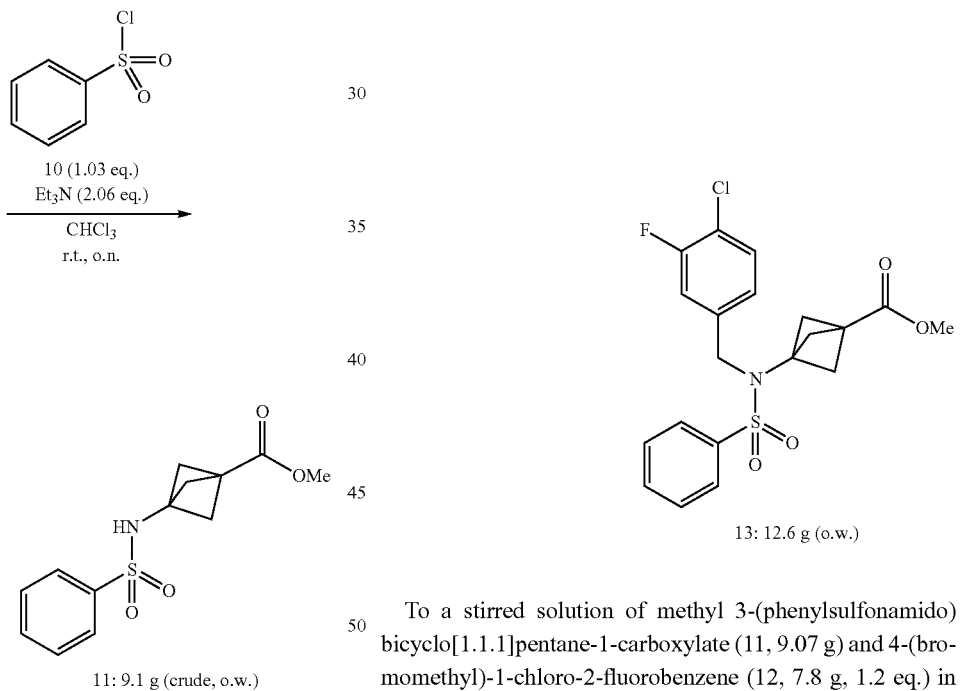

13: 12.6 g (o.w.)

To a stirred solution of methyl 3-(phenylsulfonamido)bicyclo[1.1.1]pentane-1-carboxylate (11, 9.07 g) and 4-(bromomethyl)-1-chloro-2-fluorobenzene (12, 7.8 g, 1.2 eq.) in DMF (20 mL), K₂CO₃ (8.3 g, 2. eq.) was added at room temperature. The reaction mixture was stirred for 2 hours. After the reaction completion was checked by TLC, H₂O and 1N HCl was added to the reaction mixture, and the aqueous phase was extracted twice with AcOEt. The combined extract was washed twice with diluted HCl aq. and brine. The organic phase was dried over anhydrous Na₂SO₄, filtered and concentrated in vacuo to give crude product. The crude product was purified by column chromatography on silica-gel (eluent: n-hexane/ethyl acetate) to give the 3-(N-(4-chloro-3-fluorobenzyl)phenylsulfonamido)bicyclo[1.1.1]pentane-1-carboxylate (13, 12.65 g, overweight).

Synthesis of 3-(N-(4-chloro-3-fluorobenzyl)phenylsulfonamido)bicyclo[1.1.1]pentane-1-carboxylic acid (14)

Synthesis of methyl (R)-3-((tert-butoxycarbonyl)amino)-2-(3-(N-(4-chloro-3-fluorobenzyl)phenylsulfonamido) bicyclo[1.1.1]pentane-1-carboxamido)-3-methylbutanoate (15)

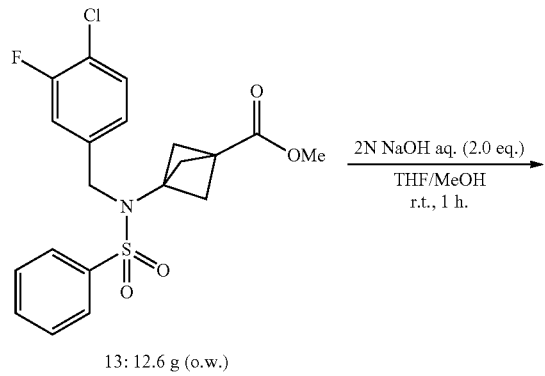

13: 12.6 g (o.w.)

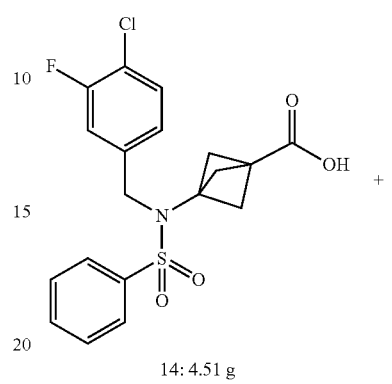

14: 4.51 g

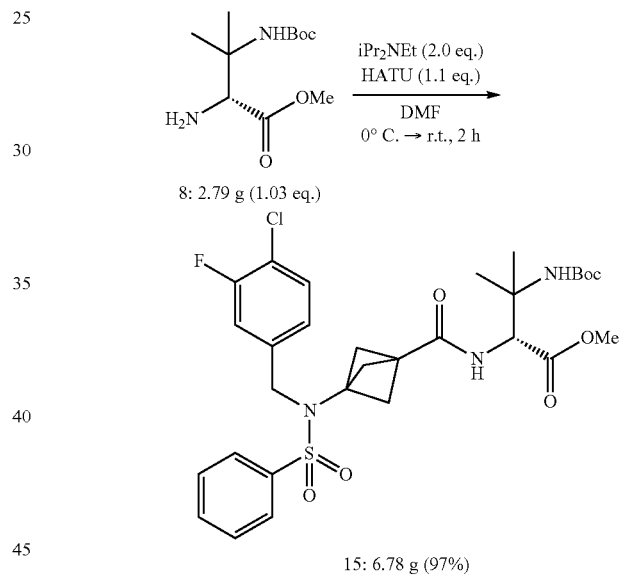

15: 6.78 g (97%)

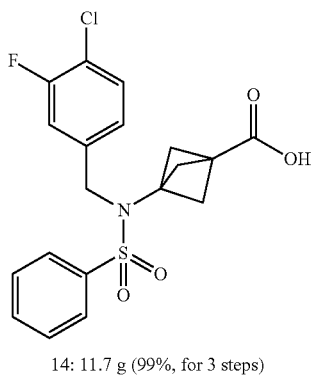

14: 11.7 g (99%, for 3 steps)

To a stirred solution of 3-(N-(4-chloro-3-fluorobenzyl)phenylsulfonamido)bicyclo[1.1.1]pentane-1-carboxylate (13, 12.65 g) in THF and MeOH (1:1, 60 mL), 2N NaOH aq. (60 mL, 2.0 eq.) was added at room temperature. The reaction mixture was stirred for 1 hour. After the reaction completion was checked by TLC, the reaction mixture was concentrated in vacuo, then 1N HCl aq. was added, and the aqueous phase was extracted twice with AcOEt. The combined extract was washed with brine. The organic phase was dried over anhydrous Na₂SO₄, filtered and concentrated in vacuo to give 3-(N-(4-chloro-3-fluorobenzyl)phenylsulfonamido)bicyclo[1.1.1]pentane-1-carboxylic acid (14, 11.75 g, 99% for 3 steps from 1). The obtained 14 was used without further purification.

To a stirred solution of 3-(N-(4-chloro-3-fluorobenzyl) phenylsulfonamido) bicyclo[1.1.1]pentane-1-carboxylic acid (14, 4.5 g), methyl (R)-2-amino-3-((tert-butoxycarbonyl)amino)-3-methylbutanoate (8, 2.8 g, 1.03 eq.) and iPr₂NEt (3.83 mL, 2.0 eq.) in DMF (20 mL), HATU (4.6 g, 1.1 eq.) was added at 0° C. The reaction mixture was stirred and warmed to ambient temperature for 2 hours. After the reaction completion was checked by TLC, H₂O and 1N HCl was added to the reaction mixture, and the aqueous phase was extracted twice with AcOEt. The combined extract was washed twice with H₂O and brine. The combined extract was dried over anhydrous Na₂SO₄, filtered and concentrated in vacuo to give crude product. The crude product was purified by column chromatography on silica-gel (eluent: n-hexane/ethyl acetate) to give the methyl(R)-3-((tert-butoxycarbonyl)amino)-2-(3-(N-(4-chloro-3-fluorobenzyl) phenylsulfonamido)bicyclo[1.1.1]pentane-1-carboxamido)-3-methylbutanoate (15, 6.78 g, 97%). The obtained 6 was used without further purification.

31

Synthesis of methyl (R)-3-amino-2-(3-(N-(4-chloro-3-fluorobenzyl)phenylsulfonamido)bicyclo[1.1.1]pentane-1-carboxamido)-3-methylbutanoate (16)

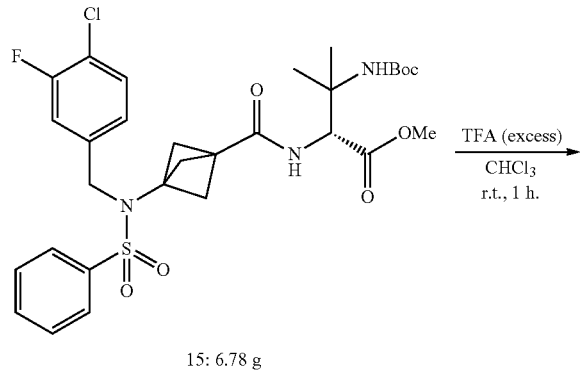

15: 6.78 g

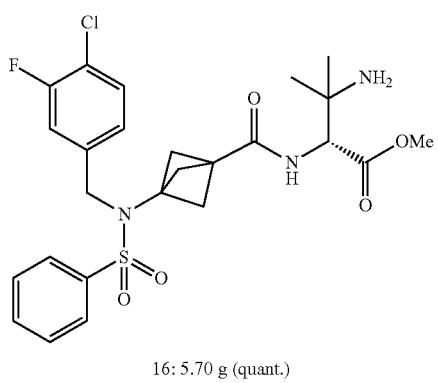

16: 5.70 g (quant.)

To a stirred solution of methyl (R)-3-((tert-butoxycarbonyl)amino)-2-(3-(N-(4-chloro-3-fluorobenzyl)phenylsulfonamido)bicyclo[1.1.1]pentane-1-carboxamido)-3-methylbutanoate (15, 6.78 g) in CHCl₃ (20 mL), TFA (20 mL) was added at room temperature. The reaction mixture was stirred for 1 hour. After the reaction completion was checked by TLC, the reaction mixture was concentrated in vacuo, then sat. NaHCO₃ aq. was carefully added, and the aqueous phase was extracted twice with AcOEt. The combined extract was washed with brine. The organic phase was dried over anhydrous Na₂SO₄, filtered and concentrated in vacuo to give methyl (R)-3-amino-2-(3-(N-(4-chloro-3-fluorobenzyl)phenylsulfonamido)bicyclo[1.1.1]pentane-1-carboxamido)-3-methylbutanoate (7, 5.70 g, quant.). The obtained 16 was used without further purification.

32

Synthesis of methyl (R)-2-(3-(N-(4-chloro-3-fluorobenzyl)phenylsulfonamido)bicyclo[1.1.1]pentan-1-yl)-4,4-dimethyl-4,5-dihydro-1H-imidazole-5-carboxylate (17)

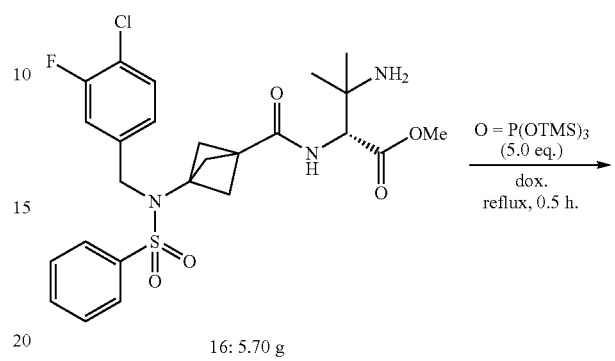

16: 5.70 g

17: 5.56 g (o.w.)

To a stirred solution of methyl (R)-3-amino-2-(3-(N-(4-chloro-3-fluorobenzyl)phenylsulfonamido)bicyclo[1.1.1]pentane-1-carboxamido)-3-methylbutanoate (16, 5.70 g) in dioxane (100 mL), tris(trimethylsilyl) phosphate (17.4 mL, 5.0 eq.) was added at room temperature. The reaction mixture was refluxed for 30 min. After the reaction completion was checked by TLC, the reaction mixture was cooled to ambient temperature, then sat. NaHCO₃ aq. was carefully added at 0° C., and the aqueous phase was extracted twice with AcOEt. The combined extract was washed with sat. NaHCO₃ aq. and brine. The organic phase was dried over anhydrous Na₂SO₄, filtered and concentrated in vacuo to give methyl (R)-2-(3-(N-(4-chloro-3-fluorobenzyl)phenylsulfonamido)bicyclo[1.1.1]pentan-1-yl)-4,4-dimethyl-4,5-dihydro-1H-imidazole-5-carboxylate (17, 5.56 g, overweight). The obtained 17 was used without further purification.

Synthesis of (R)-2-(3-(N-(4-chloro-3-fluorobenzyl)phenylsulfonamido)bicyclo[1.1.1]pentan-1-yl)-4,4-dimethyl-4,5-dihydro-1_H-imidazole-5-carboxylic acid hydrochloride (19)

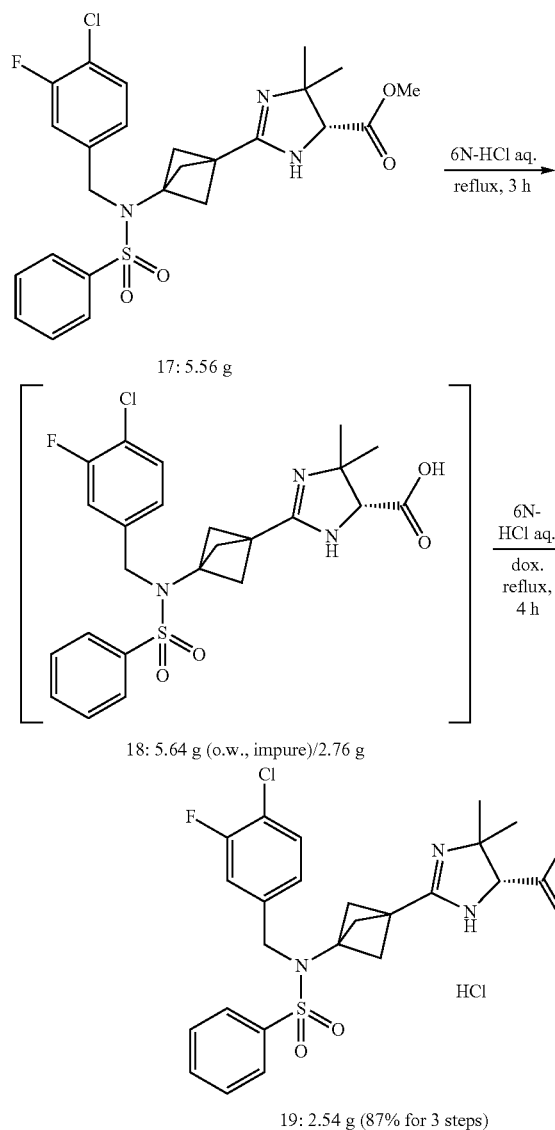

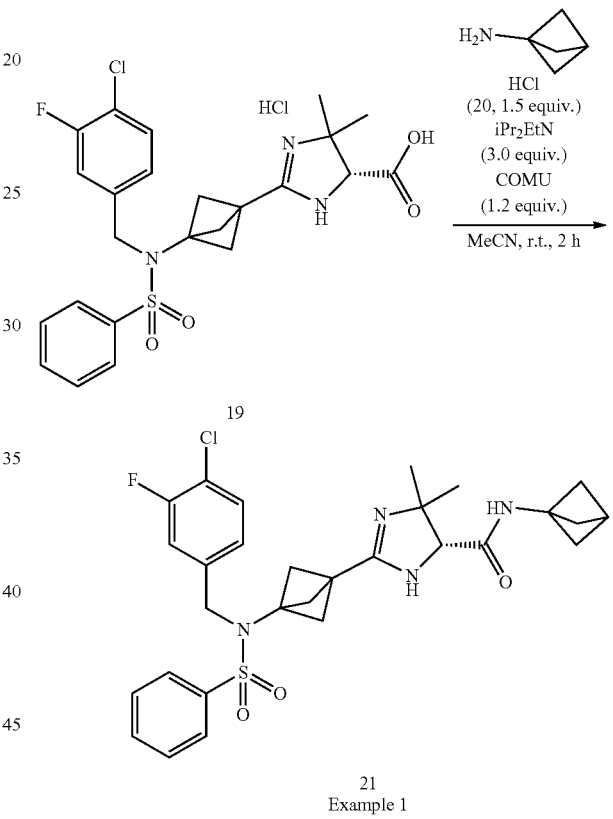

Example 1

(R)-N-(Bicyclo[1.1.1]pentan-1-yl)-2-(3-(N-(4-chloro-3-fluorobenzyl)phenylsulfonamido)bicyclo[1.1.1]pentan-1-yl)-4,4-dimethyl-4,5-dihydro-1H-imidazole-5-carboxamide (E1)

The stirred solution of methyl (R)-2-(3-(N-(4-chloro-3-fluorobenzyl)phenylsulfonamido) bicyclo[1.1.1]pentan-1-yl)-4,4-dimethyl-4,5-dihydro-1H-imidazole-5-carboxylate (17, 5.56 g) in 6N HCl aq. (15 mL) was refluxed for 3 hours. After the reaction completion was checked by TLC, the reaction mixture was cooled to ambient temperature, then NaHCO₃ (7.56 g) was carefully added at 0° C., and the aqueous phase was extracted twice with THF. The organic phase was dried over anhydrous Na₂SO₄, filtered and concentrated in vacuo to give crude product (18, 5.64 g, overweight) which contained small amount of 17. The stirred solution of the some portion of obtained mixture (2.76 g) was in 6N HCl aq. (10 mL) and dioxane (10 mL) was refluxed for 4 hours. After the reaction completion was checked by LC-MS, the reaction mixture was cooled to ambient temperature, the reaction mixture was concentrated in vacuo, then H₂O was added, and the aqueous phase was extracted twice with AcOEt. The combined extract was dried over anhydrous Na₂SO₄, filtered and concentrated in vacuo, then slurried by Et₂O to give (R)-2-(3-(N-(4-chloro-3-fluorobenzyl)phenylsulfonamido) bicyclo[1.1.1]pentan-1-yl)-4,4-dimethyl-4,5-dihydro-1H-imidazole-5-carboxylic acid (19, 2.54 g, 87% for 3 steps from 15)

(R)-2-(3-(N-(4-Chloro-3-fluorobenzyl)phenylsulfonamido)bicyclo[1.1.1]pentan-1-yl)-4,4-dimethyl-4,5-dihydro-1H-imidazole-5-carboxylic acid hydrochloride (19, 500 mg, 0.92 mmol) was dissolved in MeCN, and DIEA (357.4 mg, 2.8 mmol, 3.0 equiv), bicyclo[1.1.1]pentan-3-amine hydrochloride (20, 165.3 mg, 1.4 mmol, 1.5 equiv), and COMU (473.7 mg, 1.1 mmol, 1.2 equiv) were added thereto. After stirring at room temperature for 2 h, the solvent was removed under reduced pressure and the residue was purified by preparative TLC (CHCl₃:MeOH=9:1 (v/v)) to give 21 as white solid (198.0 mg, 37%).

MS: M/z Observed (m+H) 572.

NMR: ¹H NMR (400 MHz, Methanol-d₄) δ 1.01 (s, 3H), 1.28 (s, 3H), 2.03-2.09 (m, 12H), 2.40 (s, 1H), 3.77 (s, 1H), 4.54 (s, 2H), 7.22-7.27 (m, 1H), 7.31 (dd, J=10.2, 2.0 Hz, 1H), 7.46 (t, J=7.9 Hz, 1H), 7.58-7.65 (m, 2H), 7.66-7.73 (m, 1H), 7.87-7.93 (m, 2H).

Example 2 (E2)
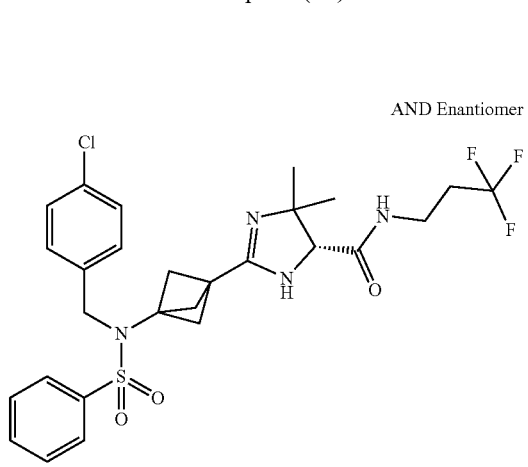
AND Enantiomer
The compound of Example 2 was prepared in an analogous manner to the procedure described hereinbefore for Example 1 in accordance with the following Scheme:
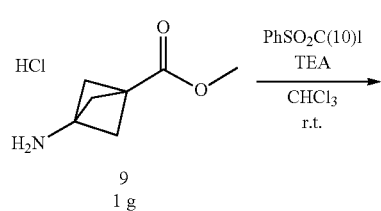
9
1 g
PhSO₂C(10)l
TEA
CHCl₃
r.t.
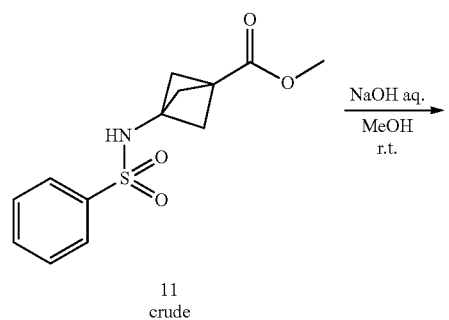
11
crude
NaOH aq.
MeOH
r.t.
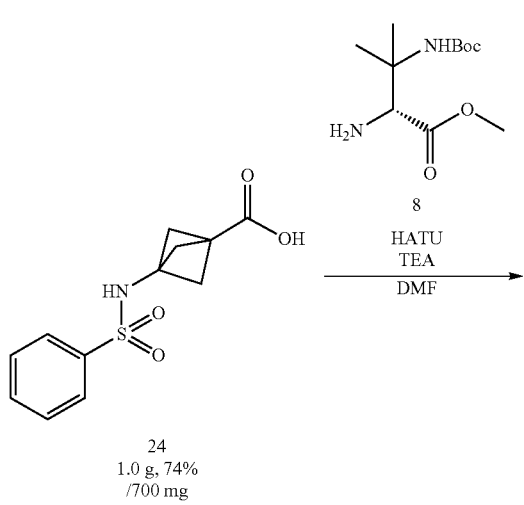
24
1.0 g, 74%
/700 mg
8
HATU
TEA
DMF
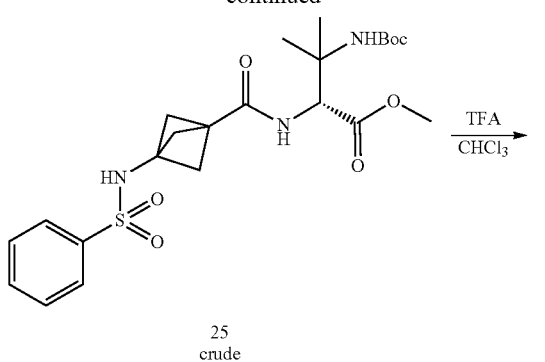
25
crude
TFA
CHCl₃
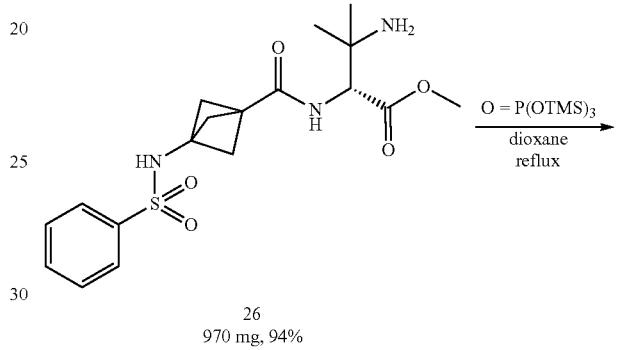
26
970 mg, 94%
O=P(OTMS)₃
dioxane
reflux
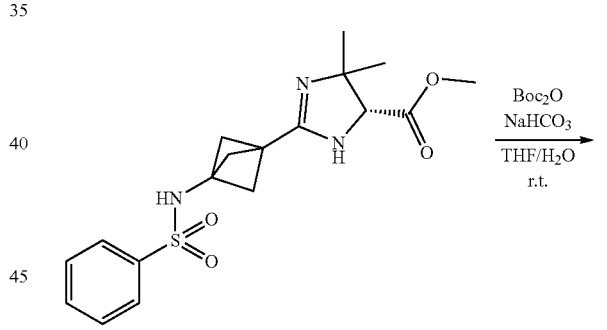
27
750 mg, 83%
/715 mg
Boc₂O
NaHCO₃
THF/H₂O
r.t.
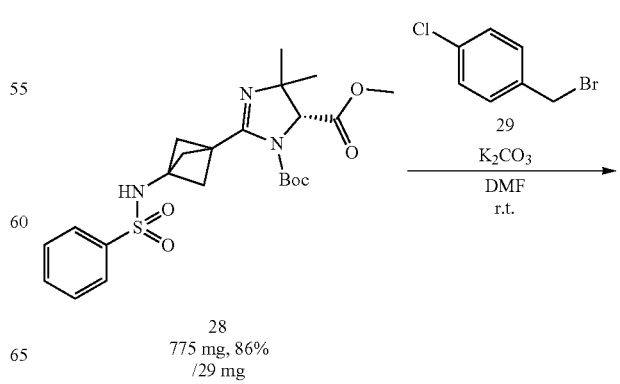
28
775 mg, 86%
/29 mg
29
K₂CO₃
DMF
r.t.

37
-continued
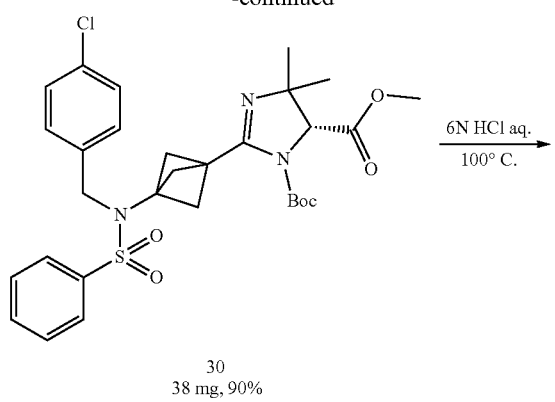
30
38 mg, 90%
38
Example 3 (E3)
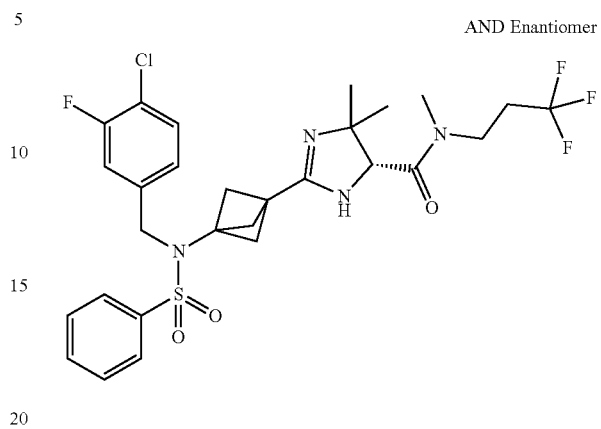
AND Enantiomer
The compound of Example 3 was prepared in an analogous manner to the procedure described hereinbefore for Example 1 in accordance with the following Scheme:
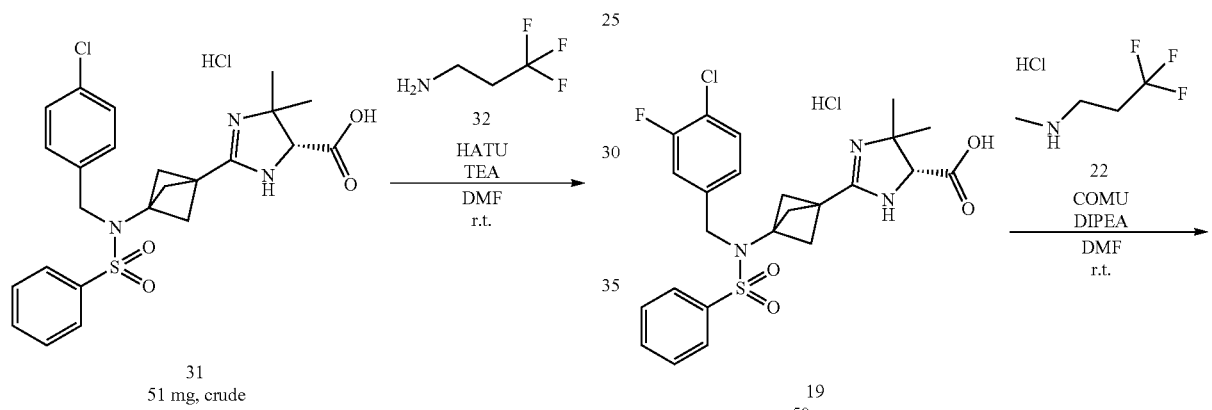
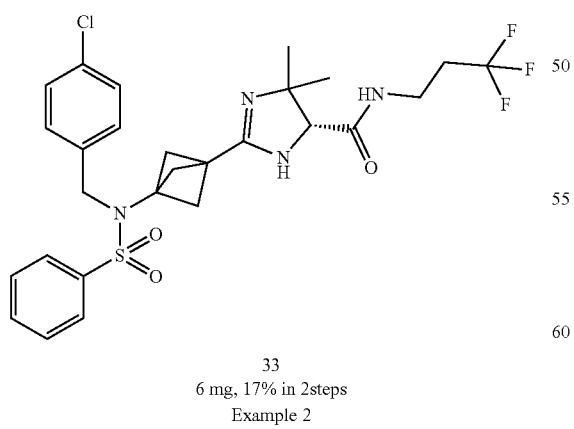
33
6 mg, 17% in 2steps
Example 2
MS: M/z Observed (m + H) 584.
23
14 mg, 25%
Example 3
MS: M/z Observed (m + H) 616.

Example 4 (E4)
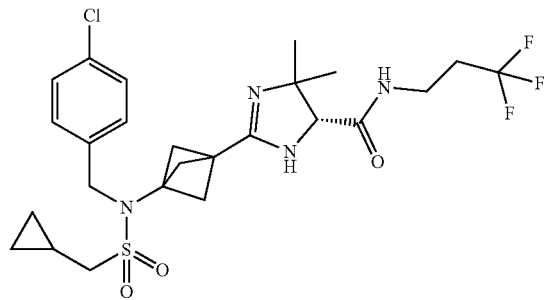
AND Enantiomer
The compound of Example 4 was prepared in an analogous manner to the procedure described hereinbefore for Example 1 in accordance with the following Scheme:
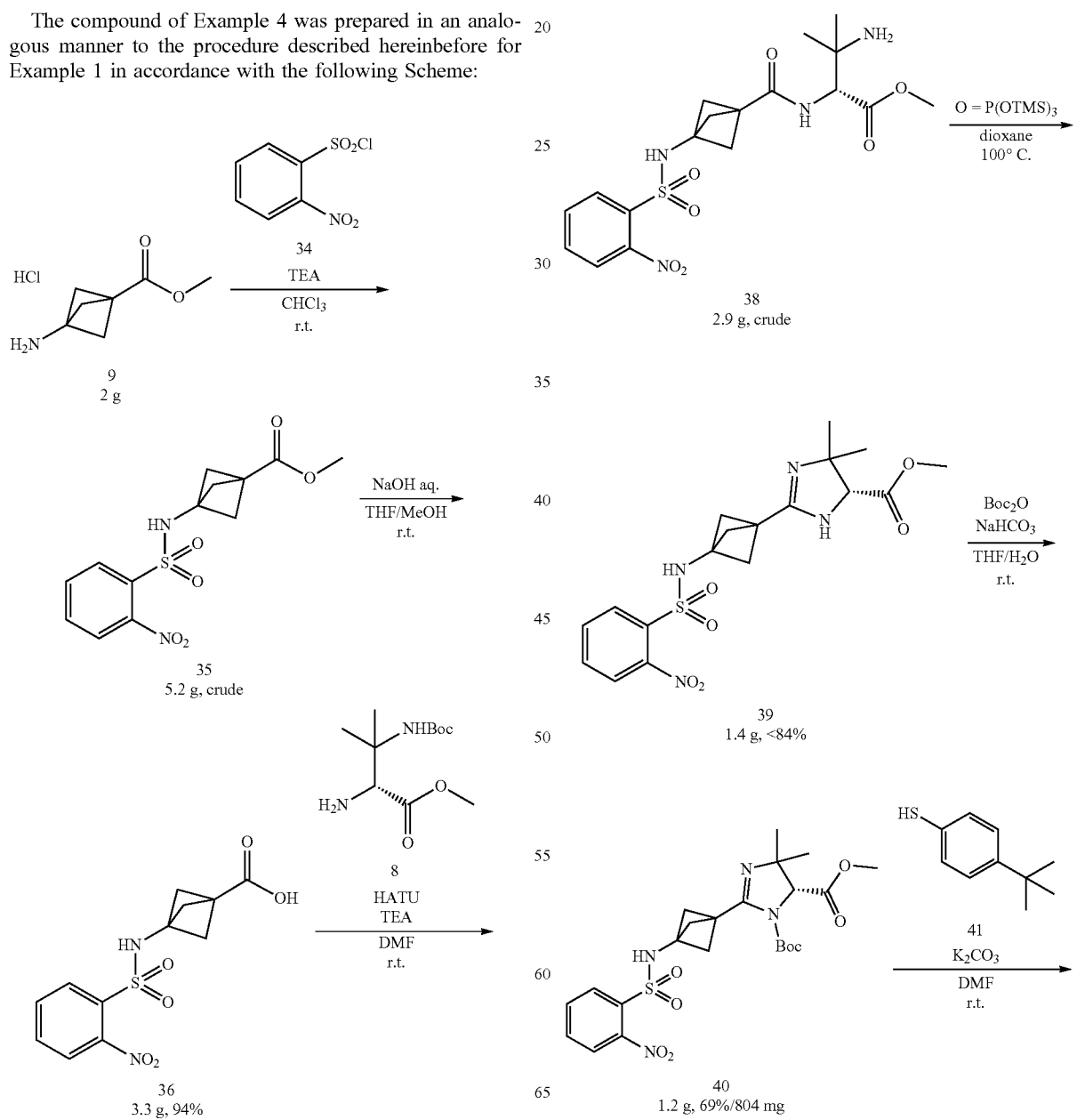

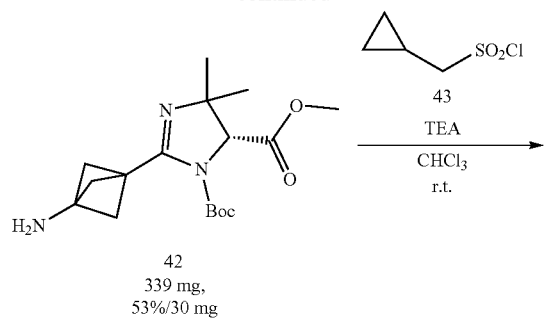
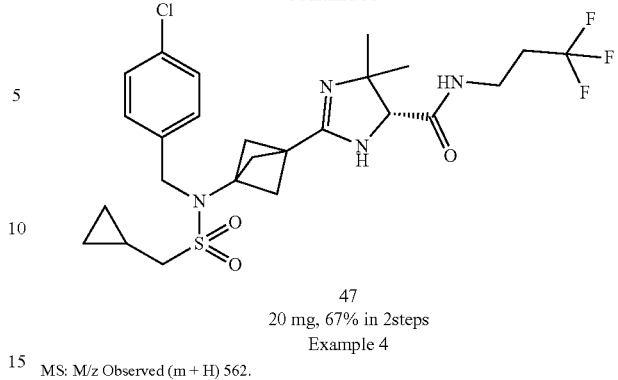
MS: M/z Observed (m + H) 562.
Example 5 (E5)
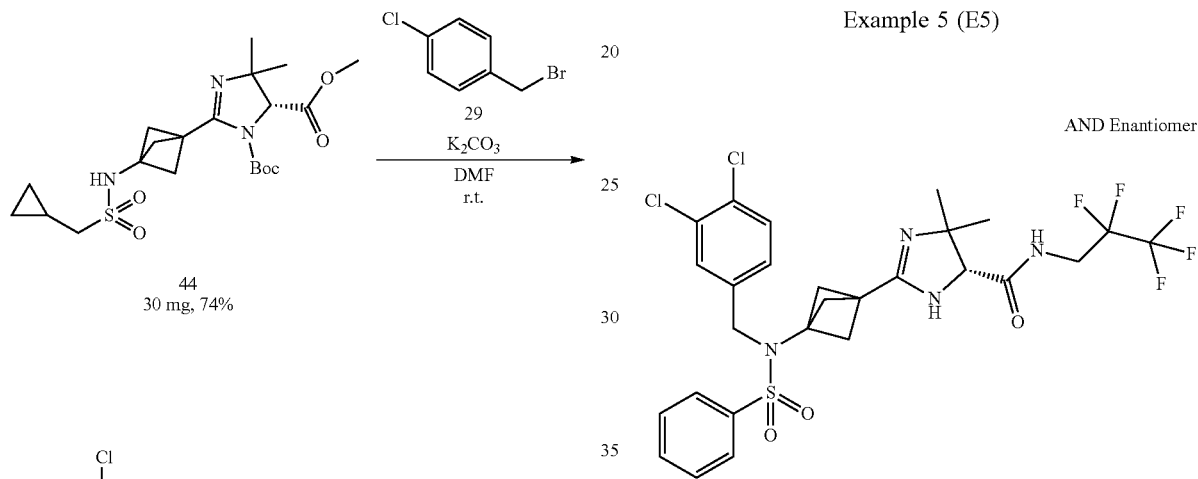
The compound of Example 5 was prepared in an analogous manner to the procedure described hereinbefore for Example 1 in accordance with the following Scheme:
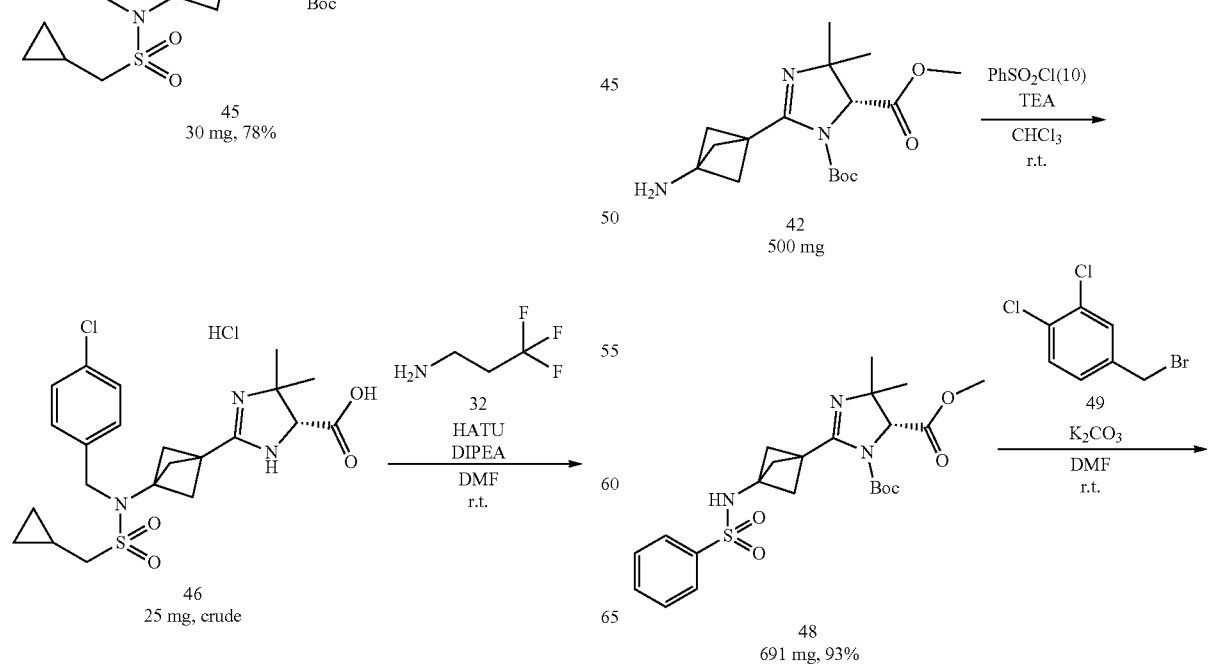

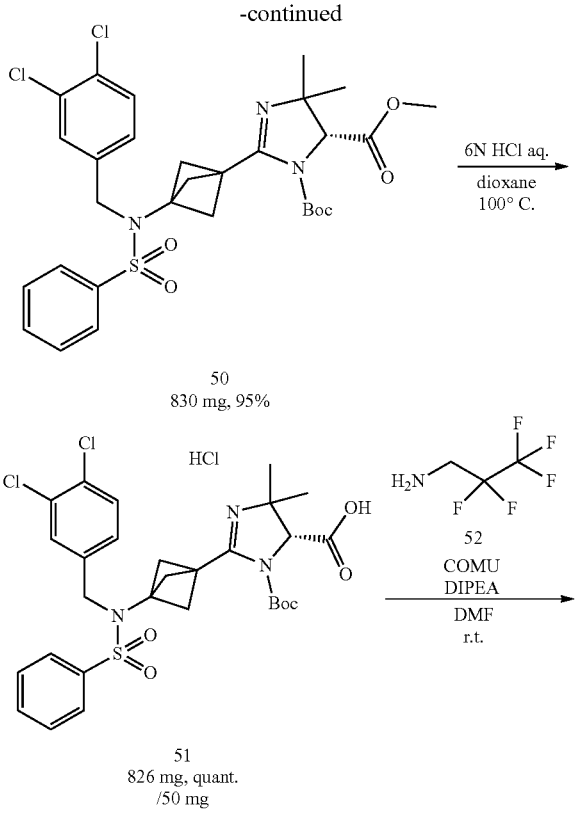
50
830 mg, 95%
51
826 mg, quant.
/50 mg
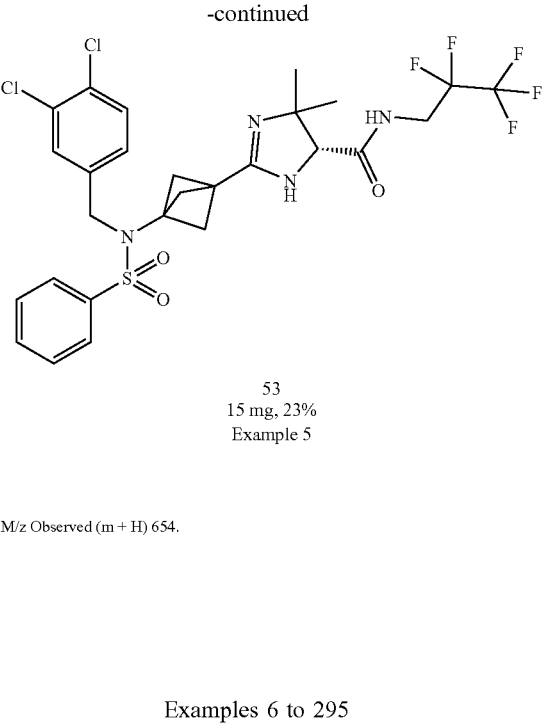
53
15 mg, 23%
Example 5
MS: M/z Observed (m + H) 654.
Examples 6 to 295
The compounds of Examples 6 to 295 were prepared in an analogous manner to the procedure described hereinbefore for Example 1:
| Example Number | Structure | | Characterising Data |
|---|---|---|---|
| 6 | 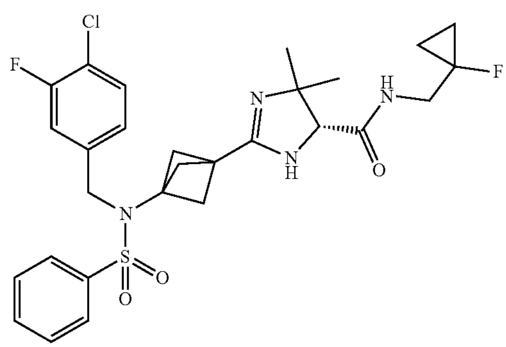 | AND Enantiomer | MS: M/z Observed (m+H) 578 |
| 7 | 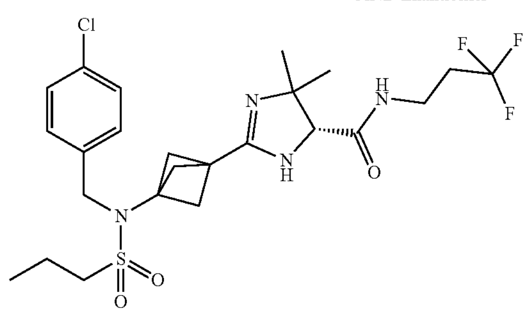 | AND Enantiomer | MS: M/z Observed 550 |

-continued
| Example Number | Structure | | Characterising Data |
|---|---|---|---|
| 8 | 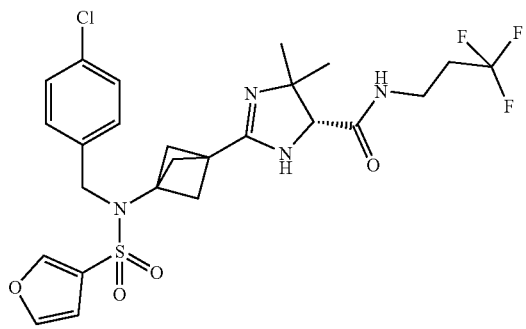 | AND Enantiomer | MS: M/z Observed 574 |
| 9 | 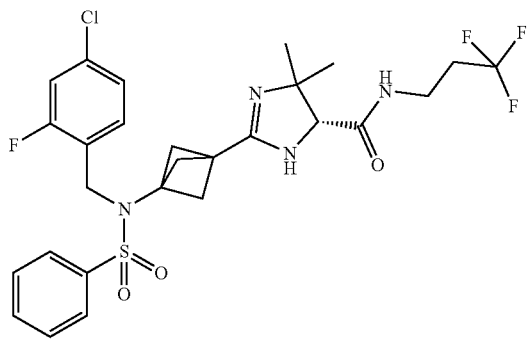 | AND Enantiomer | MS: M/z Observed 602 |
| 10 | 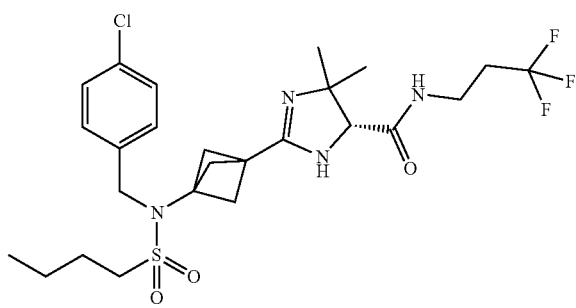 | AND Enantiomer | MS: M/z Observed 564 |
| 11 | 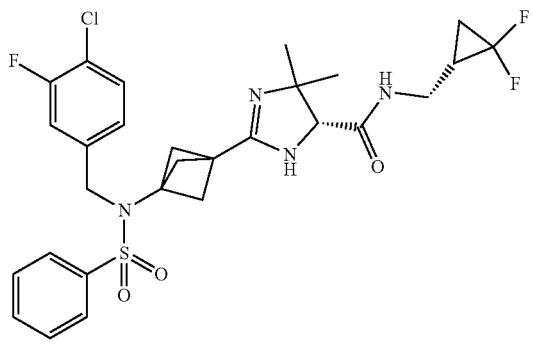 | AND Enantiomer | MS: M/z Observed 596 |

| Example Number | Structure | Characterising Data |
|---|---|---|
| 12 | AND Enantiomer 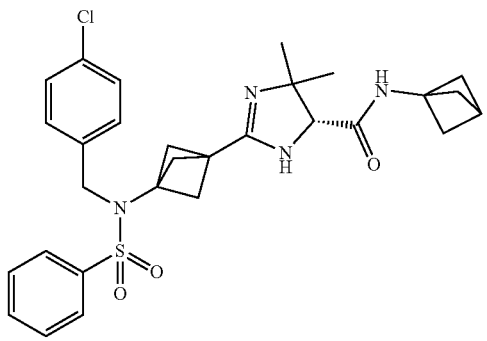 | MS: M/z Observed 554 |
| 13 | AND Enantiomer 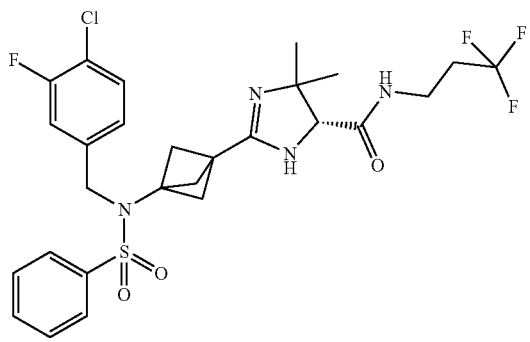 | MS: M/z Observed 602 |
| 14 | AND Enantiomer 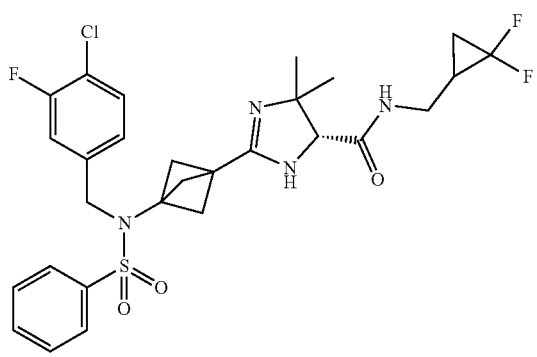 | MS: M/z Observed 596 |
| 15 | AND Enantiomer 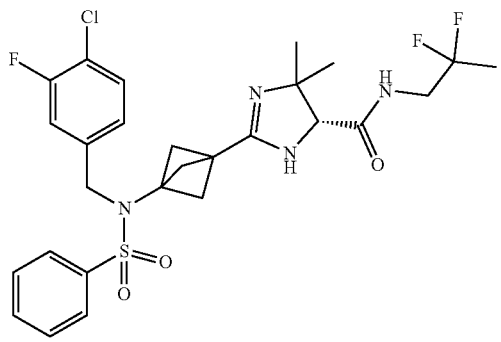 | MS: M/z Observed 584 |

-continued
| Example Number | Structure | Characterising Data |
|---|---|---|
| 16 | 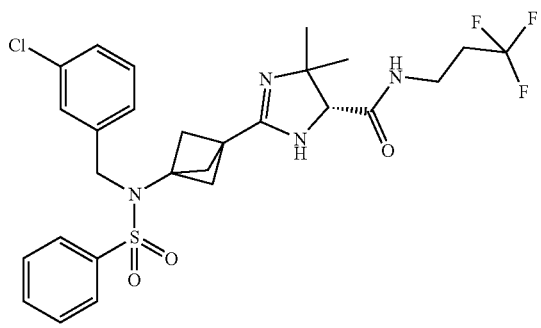 AND Enantiomer | MS: M/z Observed 584 |
| 17 | 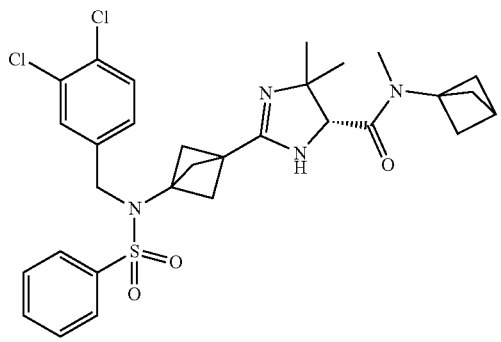 AND Enantiomer | MS: M/z Observed 602 |
| 18 | 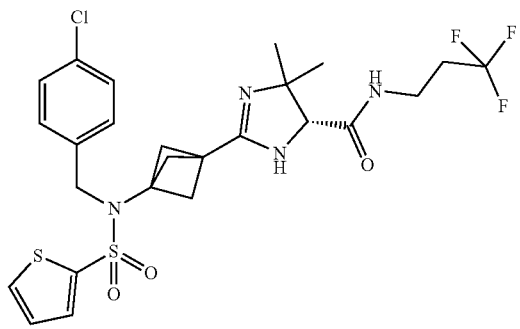 AND Enantiomer | MS: M/z Observed 590 |
| 19 | 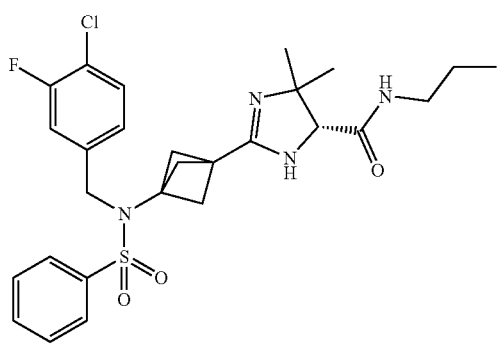 AND Enantiomer | MS: M/z Observed 548 |

| Example Number | Structure | | Characterising Data |
|---|---|---|---|
| 20 | 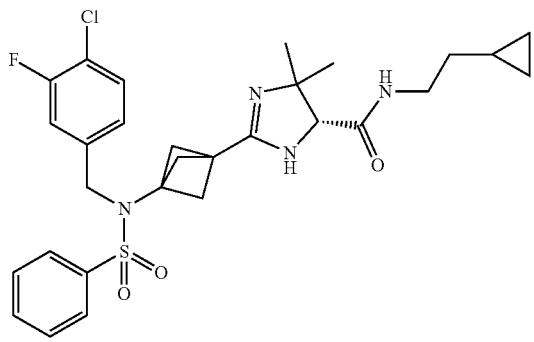 | AND Enantiomer | MS: M/z Observed 574 |
| 21 | 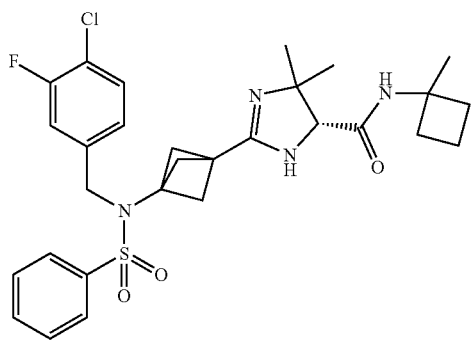 | AND Enantiomer | MS: M/z Observed 574 |
| 22 | 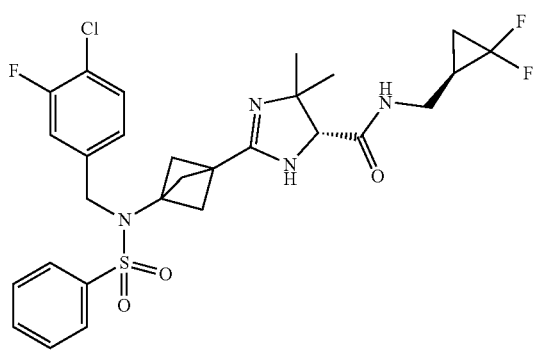 | AND Enantiomer | MS: M/z Observed 596 |
| 23 | 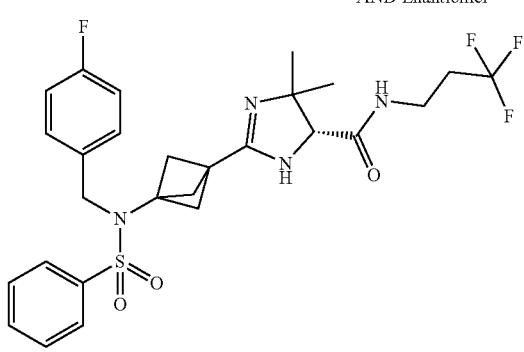 | AND Enantiomer | MS: M/z Observed 567 |

| Example Number | Structure | Characterising Data |
|---|---|---|
| 24 | AND Enantiomer 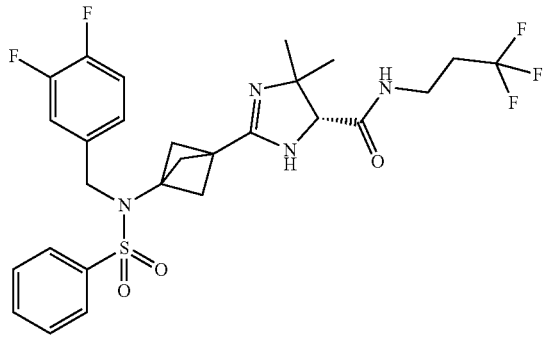 | MS: M/z Observed 585 |
| 25 | AND Enantiomer 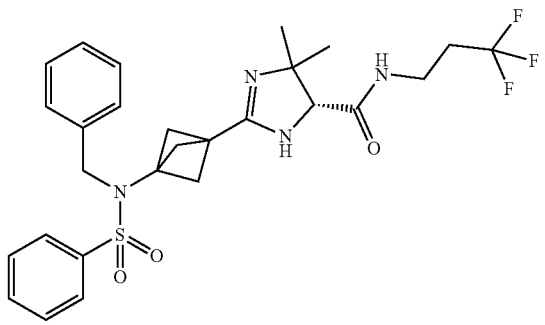 | MS: M/z Observed 549 |
| 26 | AND Enantiomer 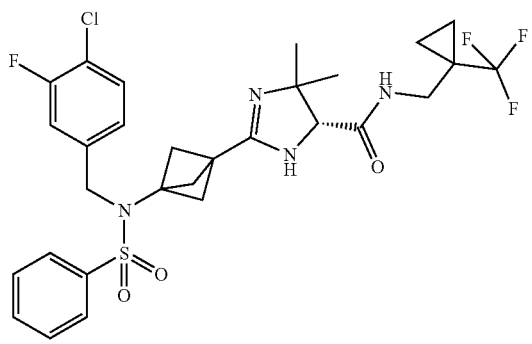 | MS: M/z Observed 628 |
| 27 | AND Enantiomer 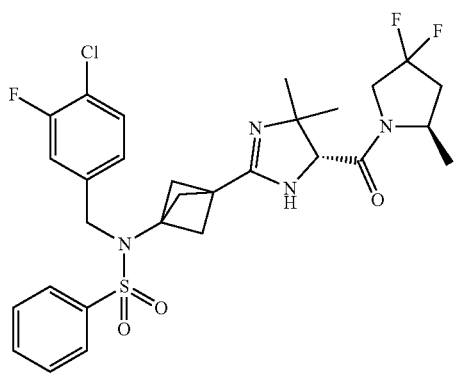 | MS: M/z Observed 610 |

| Example Number | Structure | | Characterising Data |
|---|---|---|---|
| 28 | 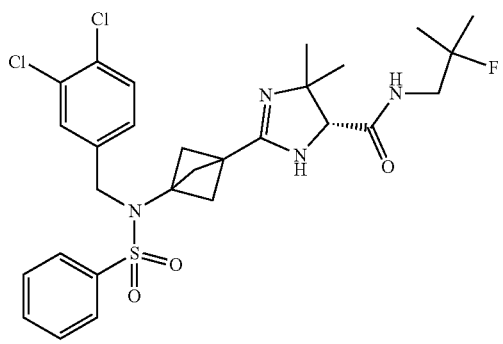 | AND Enantiomer | MS: M/z Observed 596 |
| 29 | 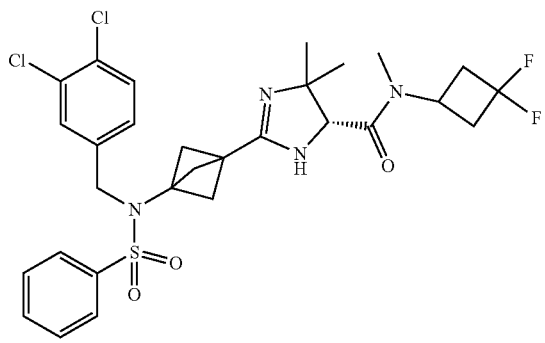 | AND Enantiomer | MS: M/z Observed 626 |
| 30 | 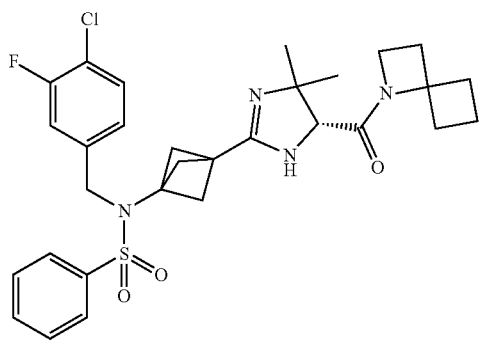 | AND Enantiomer | MS: M/z Observed 586 |
| 31 | 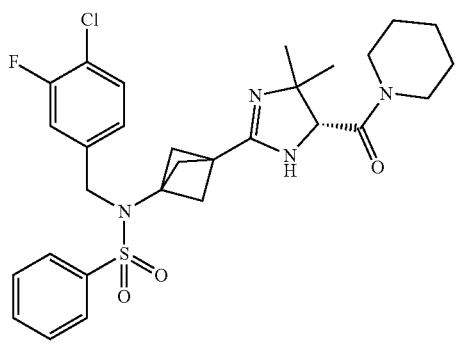 | AND Enantiomer | MS: M/z Observed 574 |

| Example Number | Structure | Characterising Data |
|---|---|---|
| 32 | AND Enantiomer 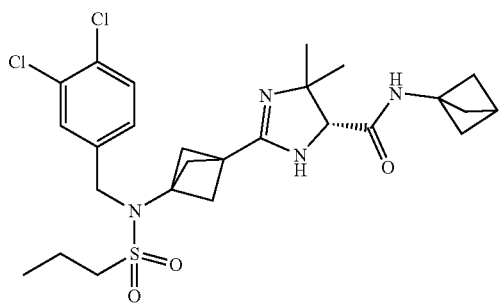 | MS: M/z Observed 554 |
| 33 | AND Enantiomer 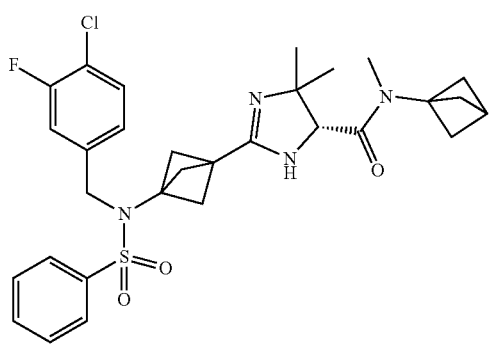 | MS: M/z Observed 586 |
| 34 | AND Enantiomer 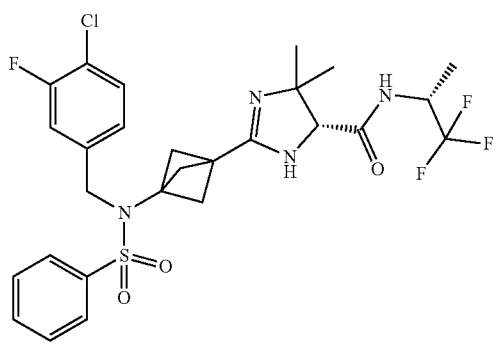 | MS: M/z Observed 602 |
| 35 | AND Enantiomer 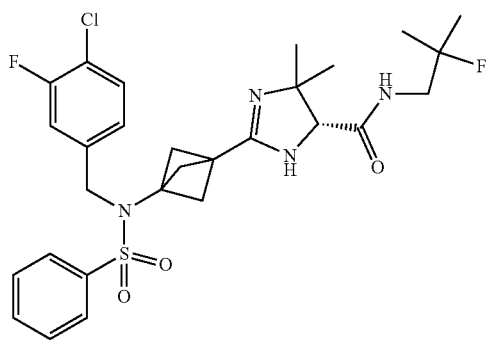 | MS: M/z Observed 580 |

| Example Number | Structure | Characterising Data |
|---|---|---|
| 36 | AND Enantiomer | MS: M/z Observed 592 |
| 37 | AND Enantiomer | MS: M/z Observed 592 |
| 38 | AND Enantiomer | MS: M/z Observed 624 |
| 39 | AND Enantiomer | MS: M/z Observed 578 |

-continued
| Example Number | Structure | Characterising Data |
|---|---|---|
| 40 | 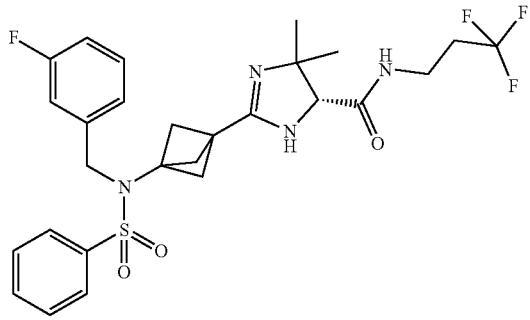 AND Enantiomer | MS: M/z Observed 567 |
| 41 | 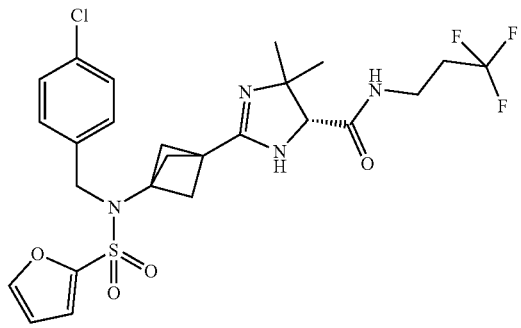 AND Enantiomer | MS: M/z Observed 574 |
| 42 | 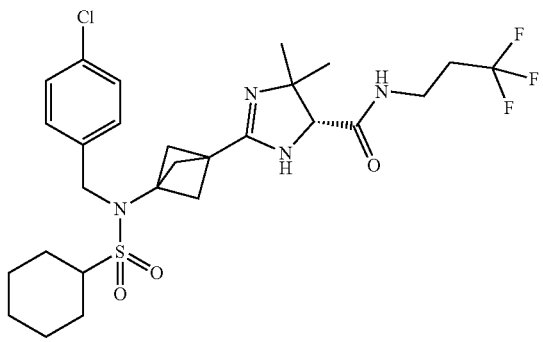 AND Enantiomer | MS: M/z Observed 590 |
| 43 | 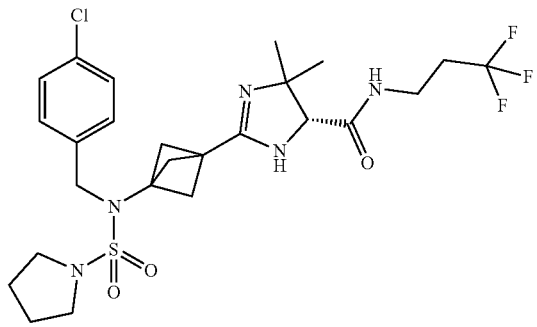 AND Enantiomer | MS: M/z Observed 577 |

| Example Number | Structure | Characterising Data |
|---|---|---|
| 44 | AND Enantiomer | MS: M/z Observed 610 |
| 45 | AND Enantiomer | MS: M/z Observed 592 |
| 46 | AND Enantiomer | MS: M/z Observed 612 |
| 47 | AND Enantiomer | MS: M/z Observed 626 |

| Example Number | Structure | | Characterising Data |
|---|---|---|---|
| 48 | 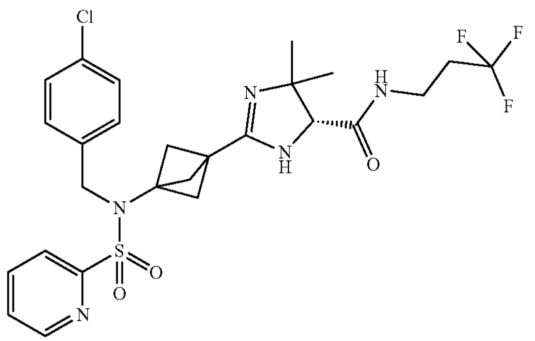 | AND Enantiomer | MS: M/z Observed 585<br>NMR: 1H-NMR (400MHz, CHLOROFORM-D) δ 1.00 (s, 3H), 1.25 (s, 1H), 1.45 (s, 3H), 2.07 (s, 6H), 2.22-2.43 (m, 2H), 3.35-3.49 (m, 1H), 3.50-3.62 (m, 1H), 4.02 (s, 1H), 4.65 (s, 2H), 7.29-7.42 (m, 4H), 7.52 (ddd, J = 7.4, 4.7, 1.0 Hz, 1H), 7.93 (td, J = 7.8, 1.8 Hz, 1H), 7.97-8.05 (m, 1H), 8.67-8.76 (m, 1H) |
| 49 | 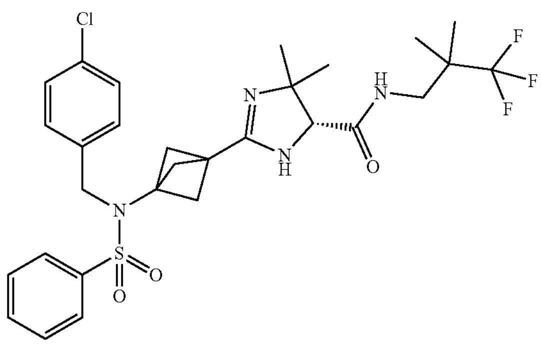 | AND Enantiomer | MS: M/z Observed 612 |
| 50 | 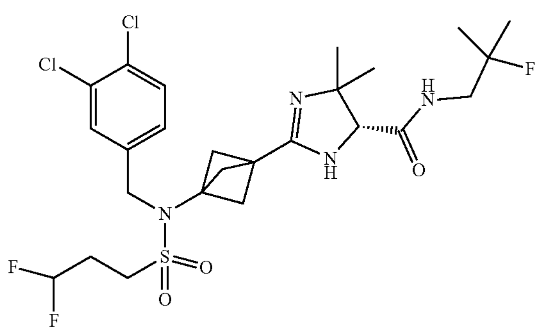 | AND Enantiomer | MS: M/z Observed 598 |
| 51 | 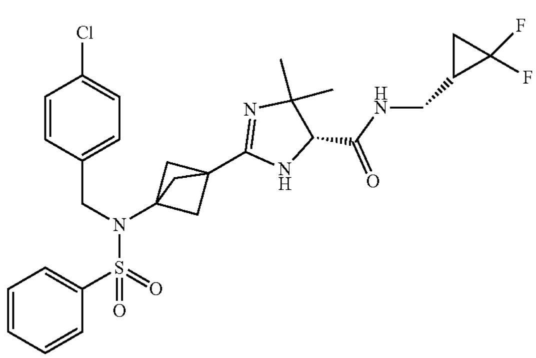 | AND Enantiomer | MS: M/z Observed 578 |

| Example Number | Structure | | Characterising Data |
|---|---|---|---|
| 52 | 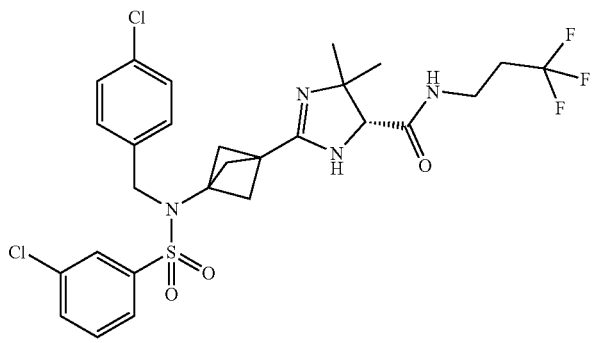 | AND Enantiomer | MS: M/z Observed 618 |
| 53 | 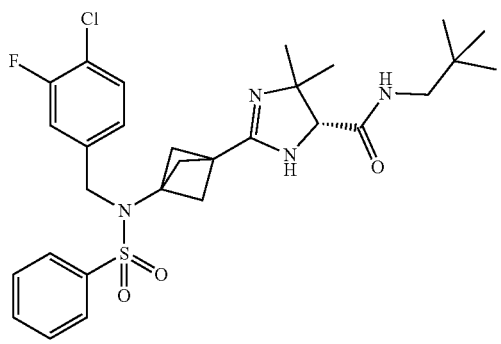 | AND Enantiomer | MS: M/z Observed 576 |
| 54 | 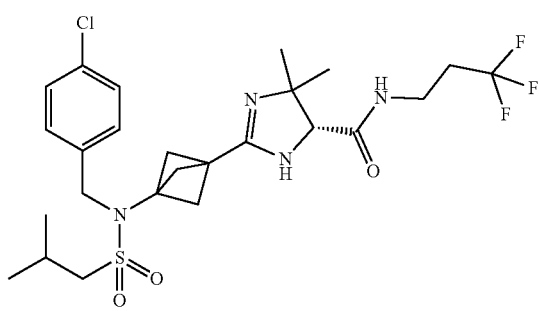 | AND Enantiomer | MS: M/z Observed 564 |
| 55 | 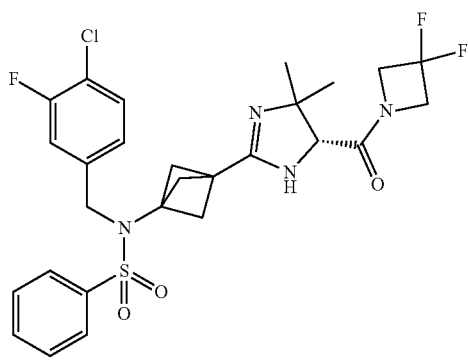 | AND Enantiomer | MS: M/z Observed 582 |

-continued
| Example Number | Structure | Characterising Data |
|---|---|---|
| 56 | AND Enantiomer 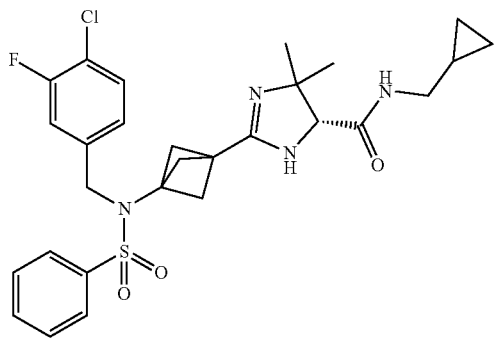 | MS: M/z Observed 560 |
| 57 | AND Enantiomer 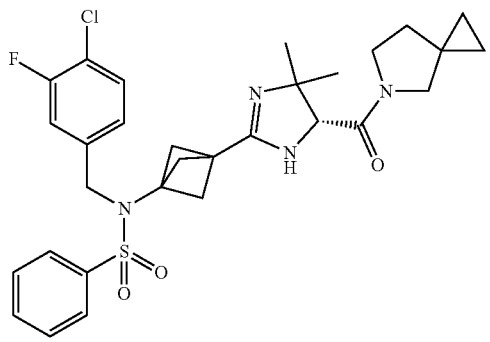 | MS: M/z Observed 586 |
| 58 | AND Enantiomer 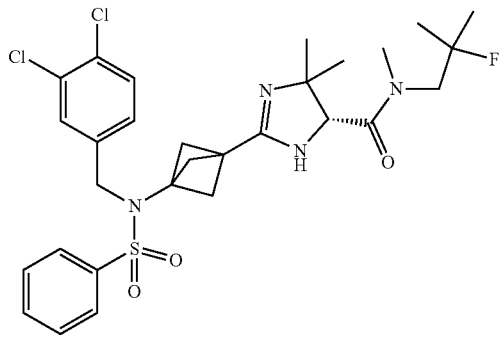 | MS: M/z Observed 610 |
| 59 | AND Enantiomer 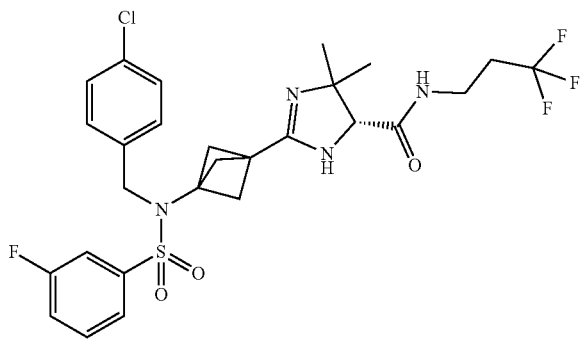 | MS: M/z Observed 602 |

-continued

| Example Number | Structure | Characterising Data |
|---|---|---|
| 60 | AND Enantiomer | MS: M/z Observed 560 |
| 61 | AND Enantiomer | MS: M/z Observed 632 |
| 62 | AND Enantiomer | MS: M/z Observed 618 |
| 63 | AND Enantiomer | MS: M/z Observed 610 |

| Example Number | Structure | | Characterising Data |
|---|---|---|---|
| 64 | 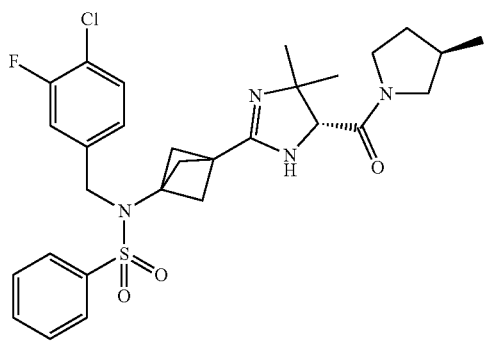 | AND Enantiomer | MS: M/z Observed 574 |
| 65 | 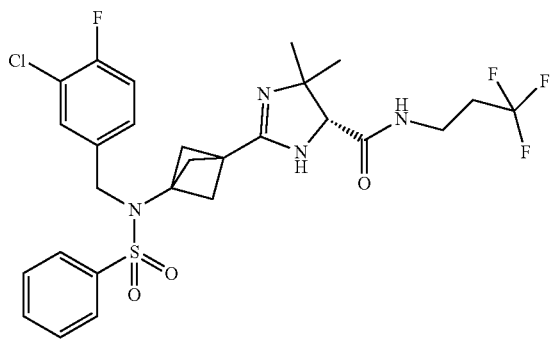 | AND Enantiomer | MS: M/z Observed 602 |
| 66 | 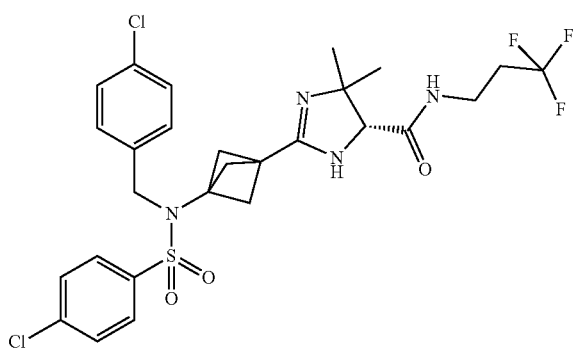 | AND Enantiomer | MS: M/z Observed 618 |
| 67 | 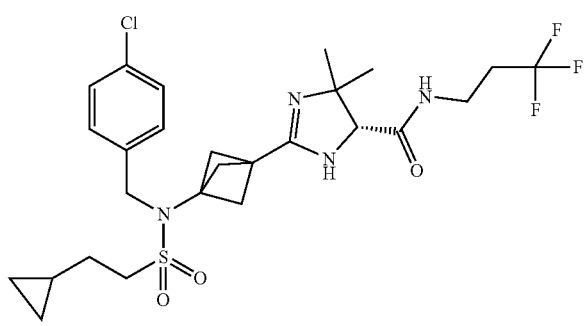 | AND Enantiomer | MS: M/z Observed 576 |

| Example Number | Structure | | Characterising Data |
|---|---|---|---|
| 68 | 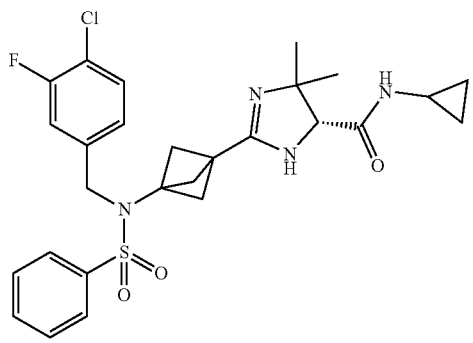 | AND Enantiomer | MS: M/z Observed 546 |
| 69 | 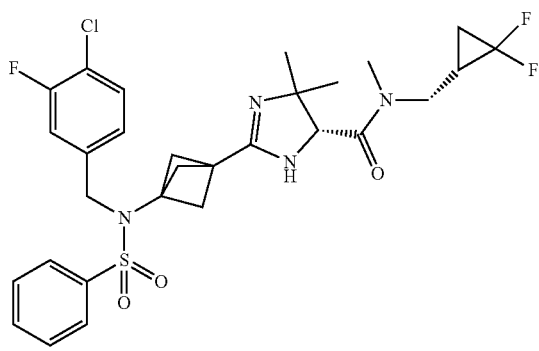 | AND Enantiomer | MS: M/z Observed 610 |
| 70 | 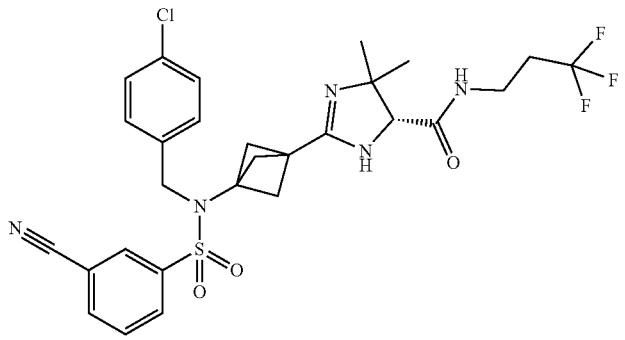 | AND Enantiomer | MS: M/z Observed 609 |

| Example Number | Structure | Characterising Data |
|---|---|---|
| 71 | AND Enantiomer 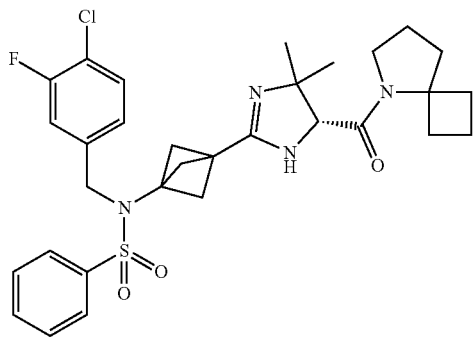 | MS: M/z Observed 600 |
| 72 | AND Enantiomer 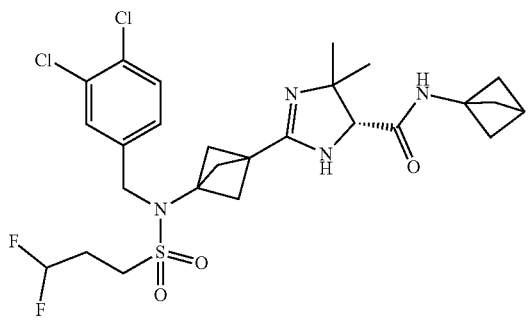 | MS: M/z Observed 590 |
| 73 | AND Enantiomer 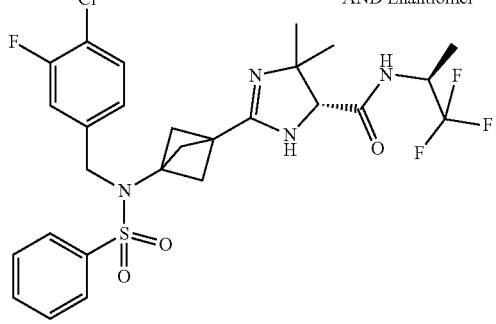 | MS: M/z Observed 602 |
| 74 | AND Enantiomer 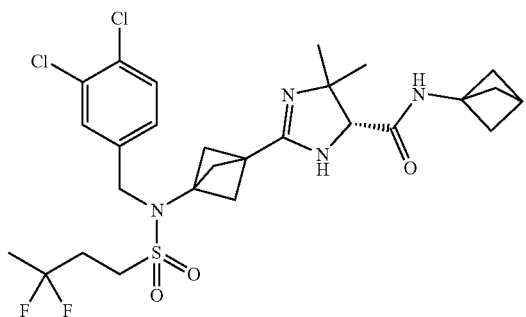 | MS: M/z Observed 604 |

-continued
| Example Number | Structure | Characterising Data |
|---|---|---|
| 75 | AND Enantiomer 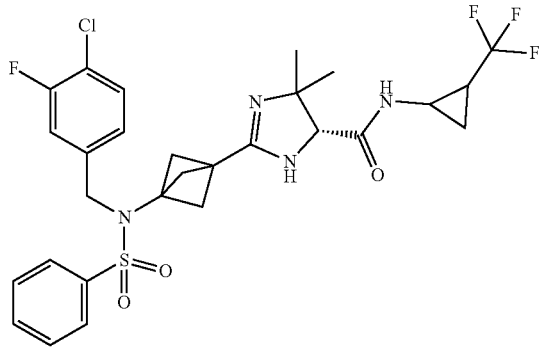 | MS: M/z Observed 614 |
| 76 | AND Enantiomer 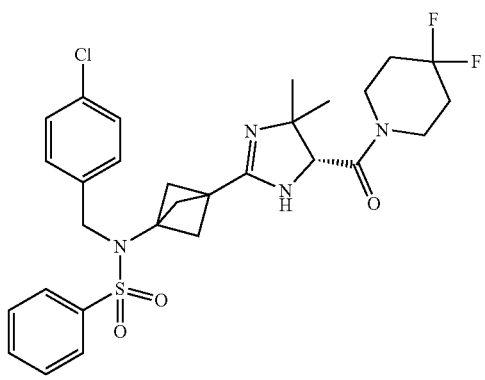 | MS: M/z Observed 592 |
| 77 | AND Enantiomer 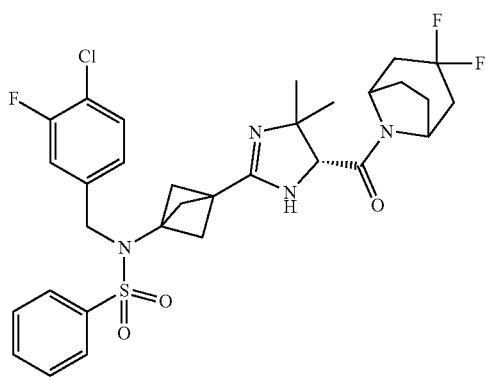 | MS: M/z Observed 636 |
| 78 | AND Enantiomer 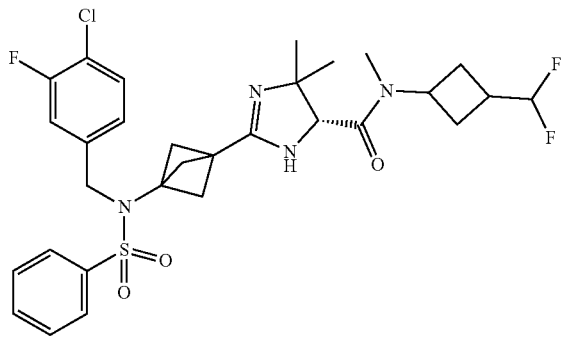 | MS: M/z Observed 624 |

| Example Number | Structure | Characterising Data |
|---|---|---|
| 79 | AND Enantiomer 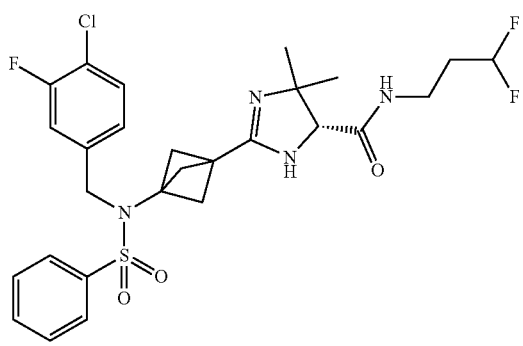 | MS: M/z Observed 584 |
| 80 | AND Enantiomer 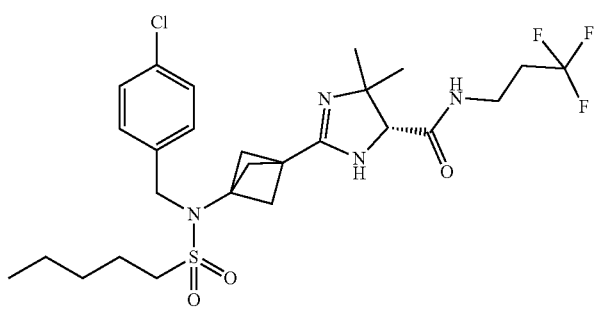 | MS: M/z Observed 578 |
| 81 | AND Enantiomer 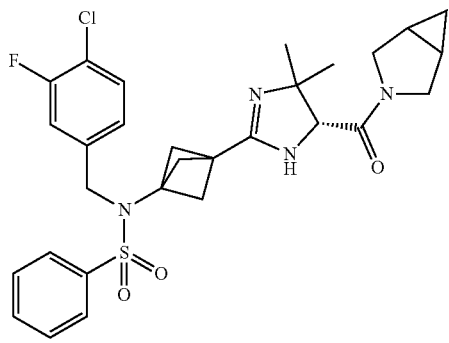 | MS: M/z Observed 572 |
| 82 | AND Enantiomer 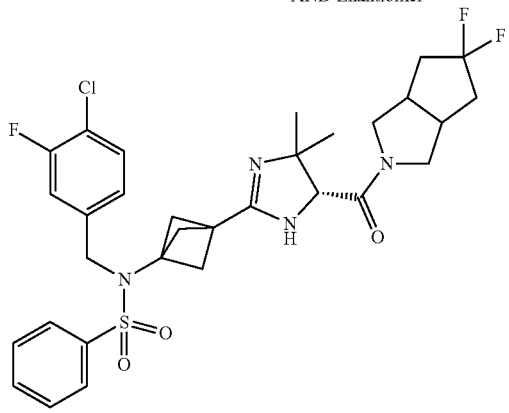 | MS: M/z Observed 636 |

-continued
| Example Number | Structure | Characterising Data |
|---|---|---|
| 83 | AND Enantiomer 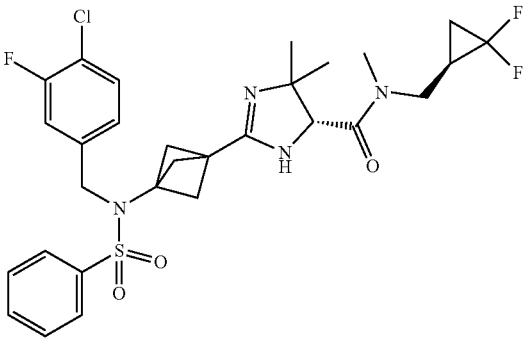 | MS: M/z Observed 610 |
| 84 | AND Enantiomer 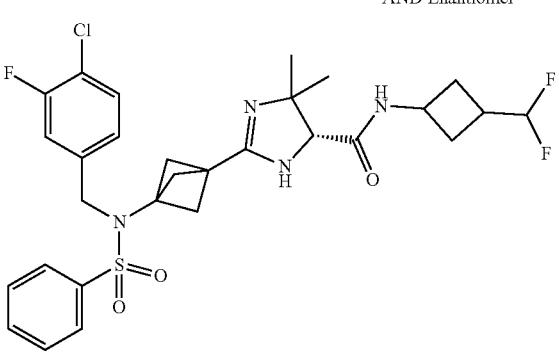 | MS: M/z Observed 610 |
| 85 | AND Enantiomer 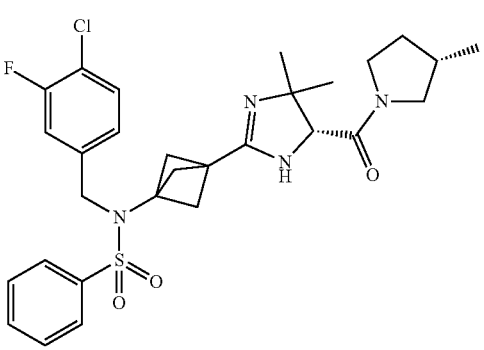 | MS: M/z Observed 574 |
| 86 | AND Enantiomer 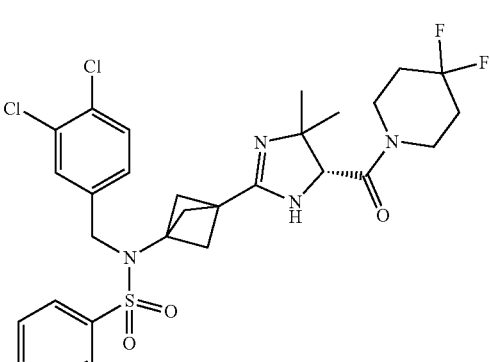 | MS: M/z Observed 626 |

| Example Number | Structure | Characterising Data |
|---|---|---|
| 87 | AND Enantiomer 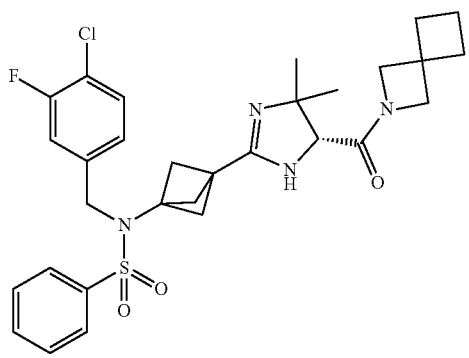 | MS: M/z Observed 586 |
| 88 | AND Enantiomer 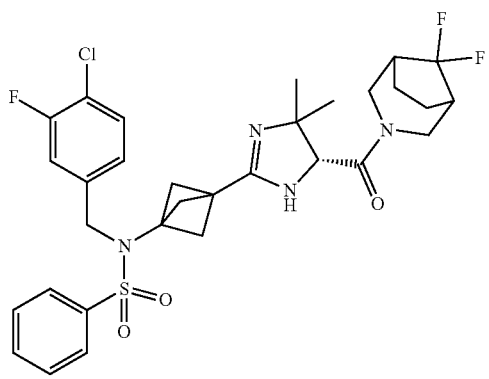 | MS: M/z Observed 636 |
| 89 | AND Enantiomer 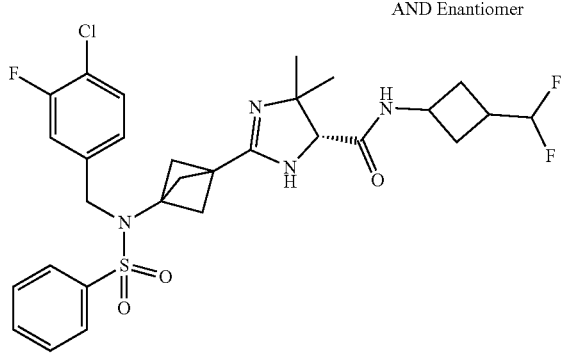 [SMILES: CC1(C)N=C(C23CC(N(Cc4ccc(Cl)c(F)c4)S(=O)(=O)c4ccccc4)(C2)C3)N[C@H]1C(=O)NC1CC(C(F)F)C1] | MS: M/z Observed 610 |

| Example Number | Structure | | Characterising Data |
|---|---|---|---|
| 90 | 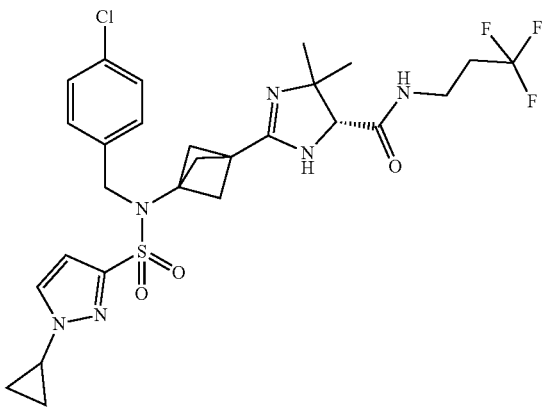 | AND Enantiomer | MS: M/z Observed 614 |
| 91 | 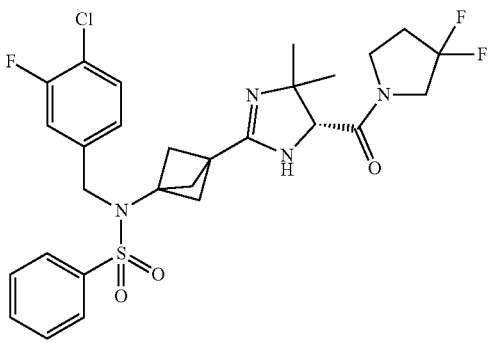 | AND Enantiomer | MS: M/z Observed 596 |
| 92 | 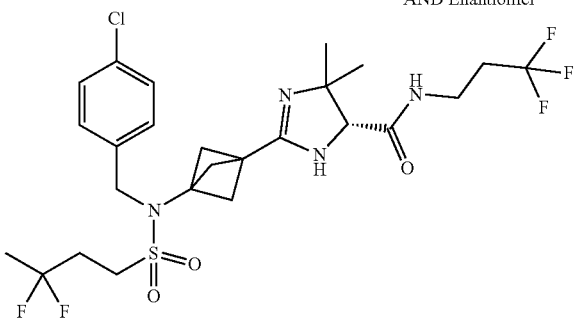 | AND Enantiomer | MS: M/z Observed 568<br>NMR: 1H-NMR (400 MHz, CHLOROFORM-D) δ 1.03 (s, 3H), 1.25 (s, 1H), 1.48 (s, 3H), 2.12-2.48 (m, 10H), 3.15 (t, J = 7.6 Hz, 2H), 3.36-3.52 (m, 1H), 3.52-3.66 (m, 1H), 4.05 (s, 1H), 4.45 (s, 2H), 4.52 (t, J = 5.5 Hz, 1H), 4.64 (t, J = 5.5 Hz, 1H), 7.15 (br s, 1H), 7.28-7.36 (m, 4H) |
| 93 | 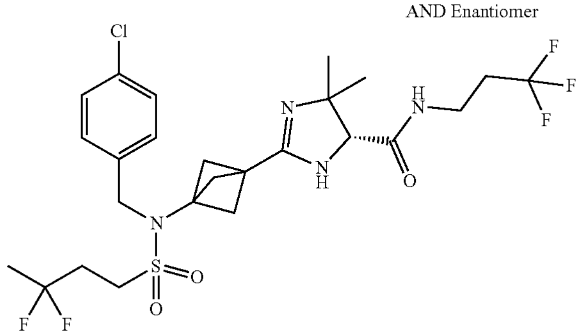 [SMILES: CC(F)(F)CCS(=O)(=O)N(Cc1ccc(Cl)cc1)C12CC(C3=NC(C)(C)[C@H](C(=O)NCCC(F)(F)F)N3)(C1)C2] | AND Enantiomer | MS: M/z Observed 600 |

| Example Number | Structure | Characterising Data |
|---|---|---|
| 94 | AND Enantiomer 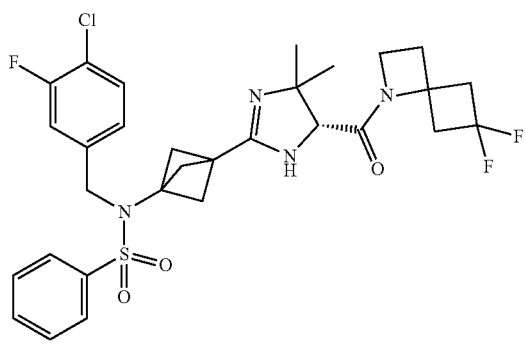 | MS: M/z Observed 622 |
| 95 | AND Enantiomer 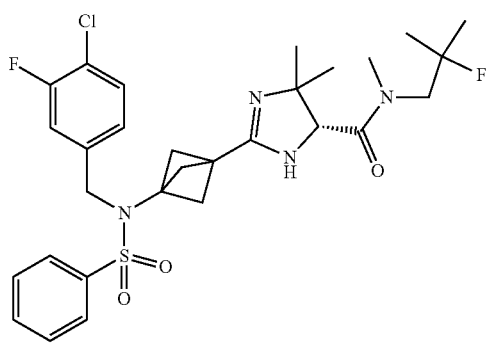 | MS: M/z Observed 594 |
| 96 | AND Enantiomer 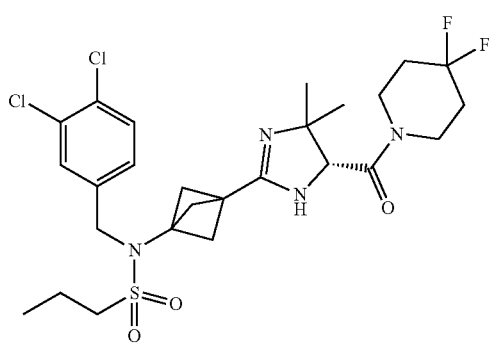 | MS: M/z Observed 592 |
| 97 | 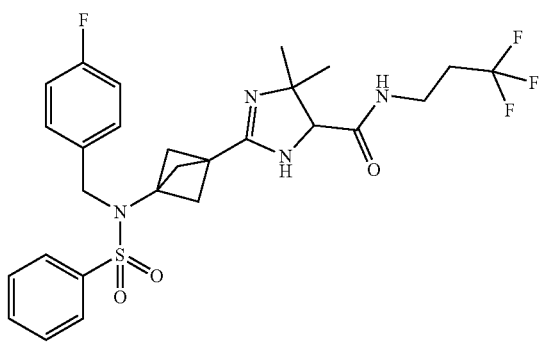 [SMILES: CC1(C)N=C(C23CC(N(Cc4ccc(F)cc4)S(=O)(=O)c4ccccc4)(C2)C3)NC1C(=O)NCCC(F)(F)F] | MS: M/z Observed 567 |

| Example Number | Structure | | Characterising Data |
|---|---|---|---|
| 98 | 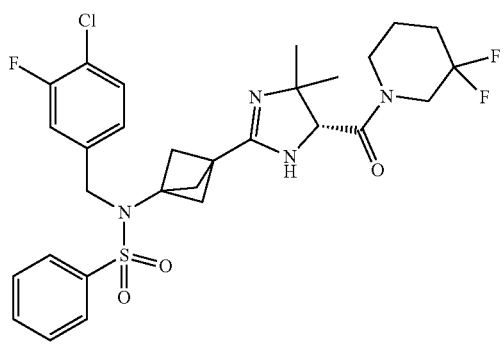 | AND Enantiomer | MS: M/z Observed 610 |
| 99 | 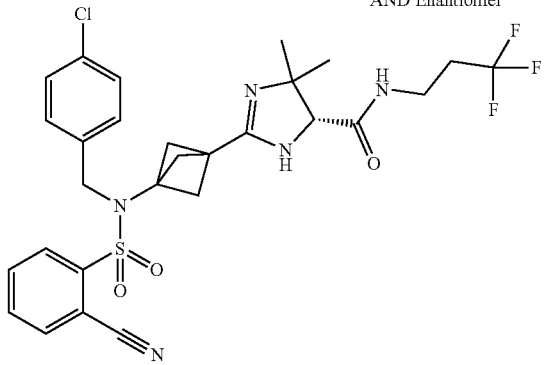 | AND Enantiomer | MS: M/z Observed 609 |
| 100 | 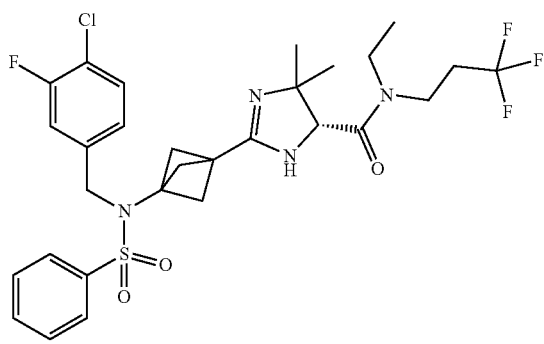 | AND Enantiomer | MS: M/z Observed 630 |
| 101 | 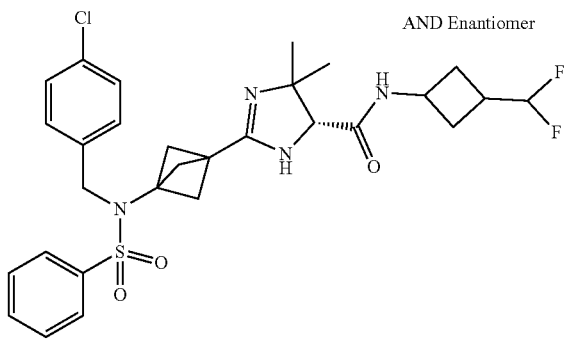 [SMILES: CC1(C)N=C(C23CC(N(Cc4ccc(Cl)cc4)S(=O)(=O)c4ccccc4)(C2)C3)N[C@H]1C(=O)NC1CC(C(F)F)C1] | AND Enantiomer | MS: M/z Observed 592 |

| Example Number | Structure | | Characterising Data |
|---|---|---|---|
| 102 | 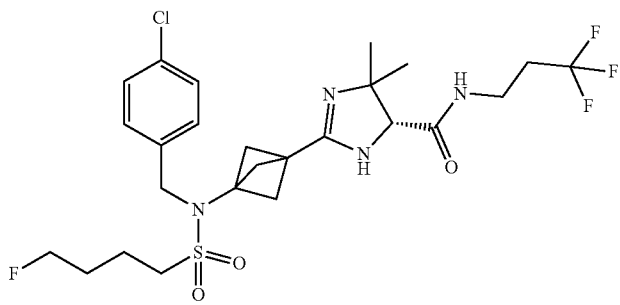 | AND Enantiomer | MS: M/z Observed 582 |
| 103 | 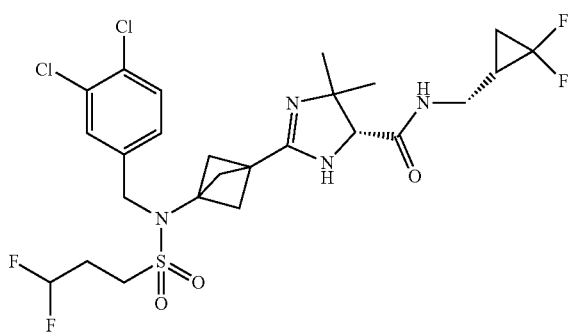 | AND Enantiomer | MS: M/z Observed 614 |
| 104 | 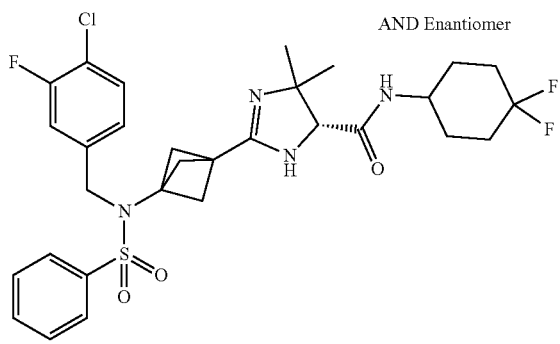 [SMILES: CC1(C)N=C(C23CC(N(Cc4ccc(Cl)c(F)c4)S(=O)(=O)c4ccccc4)(C2)C3)N[C@H]1C(=O)NC1CCC(F)(F)CC1] | AND Enantiomer | MS: M/z Observed 624 |
| 105 | 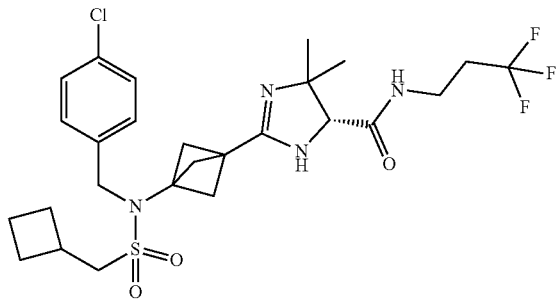 | AND Enantiomer | MS: M/z Observed 576 |

-continued

| Example Number | Structure | Characterising Data |
|---|---|---|
| 106 | AND Enantiomer | MS: M/z Observed 594 |
| 107 | AND Enantiomer | MS: M/z Observed 618 |
| 108 | AND Enantiomer | MS: M/z Observed 616 |
| 109 | AND Enantiomer | MS: M/z Observed 600 |

-continued
| Example Number | Structure | | Characterising Data |
|---|---|---|---|
| 110 | 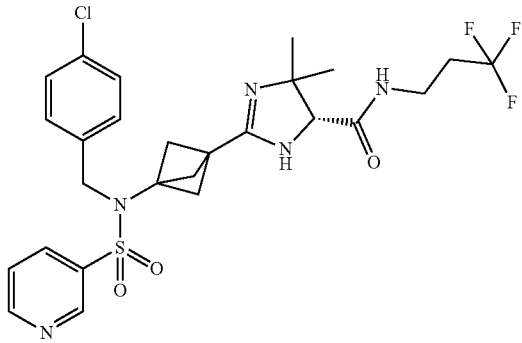 | AND Enantiomer | MS: M/z Observed 585 |
| 111 | 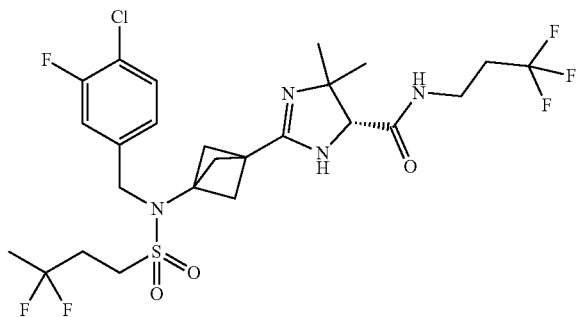 | AND Enantiomer | MS: M/z Observed 618 |
| 112 | 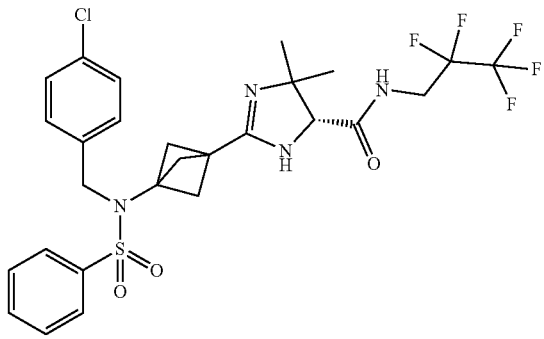 | AND Enantiomer | MS: M/z Observed 620 |
| 113 | 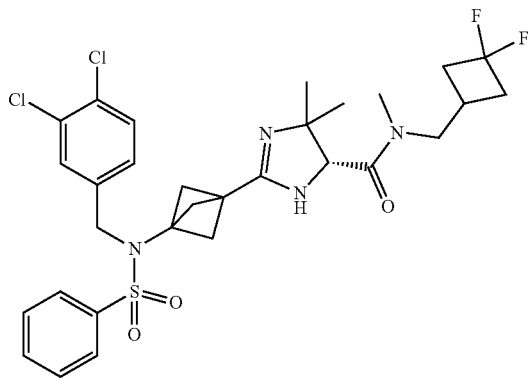 | AND Enantiomer | MS: M/z Observed 640 |

| Example Number | Structure | | Characterising Data |
|---|---|---|---|
| 114 | 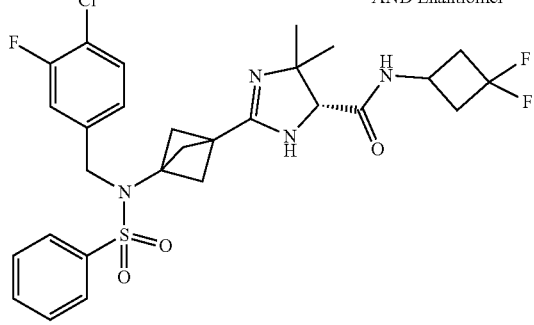 | AND Enantiomer | MS: M/z Observed 596 |
| 115 | 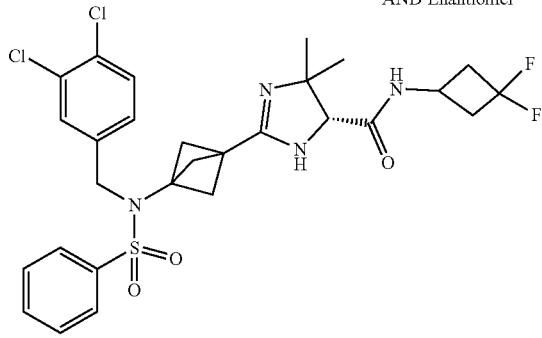 | AND Enantiomer | MS: M/z Observed 612 |
| 116 | 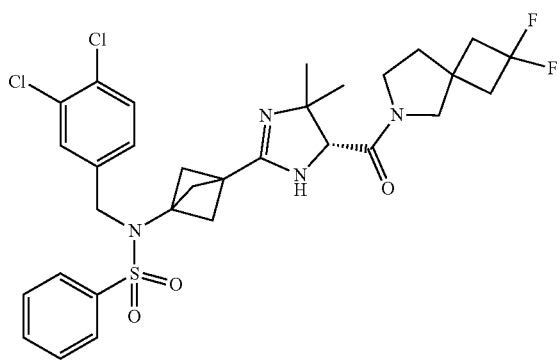 | AND Enantiomer | MS: M/z Observed 652 |
| 117 | 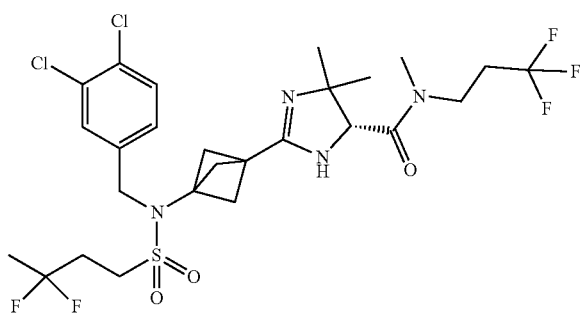 | AND Enantiomer | MS: M/z Observed 648 |

| Example Number | Structure | | Characterising Data |
|---|---|---|---|
| 118 | 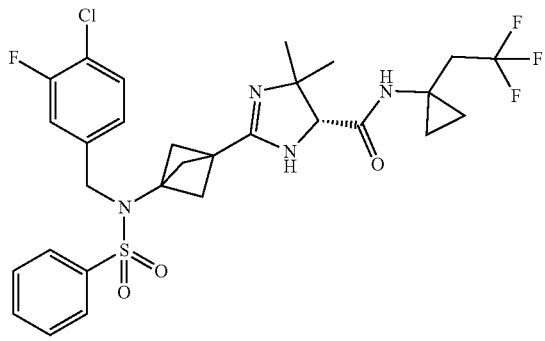 | AND Enantiomer | MS: M/z Observed 628 |
| 119 | 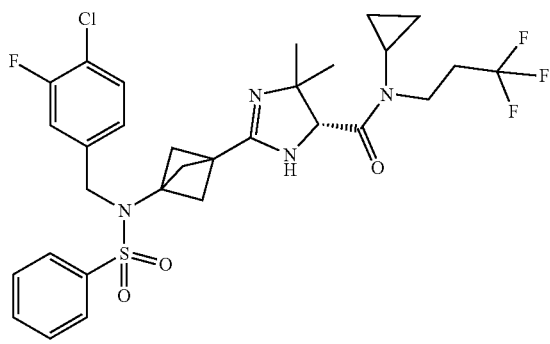 | AND Enantiomer | MS: M/z Observed 642 |
| 120 | 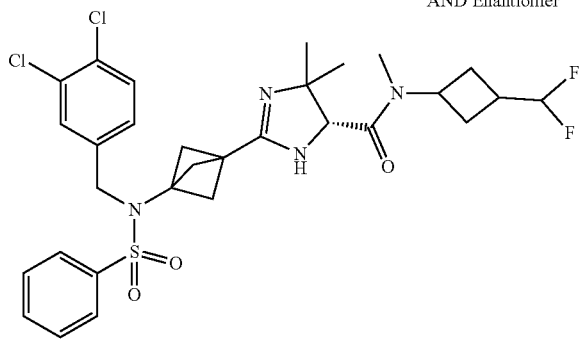 | AND Enantiomer | MS: M/z Observed 640 |
| 121 | 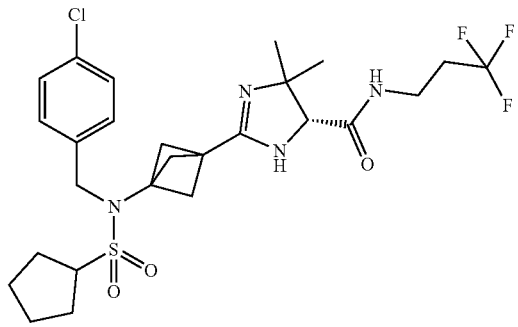 | AND Enantiomer | MS: M/z Observed 576 |

| Example Number | Structure | | Characterising Data |
|---|---|---|---|
| 122 | 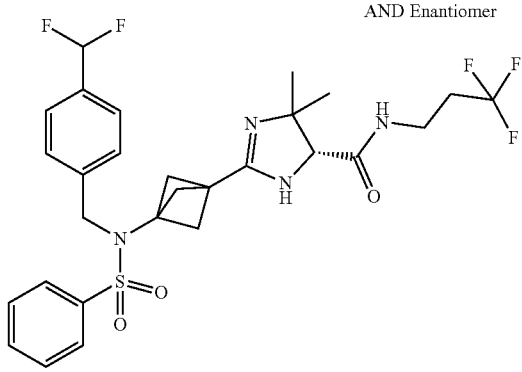 [SMILES: CC1(C)N=C(C23CC(N(Cc4ccc(C(F)F)cc4)S(=O)(=O)c4ccccc4)(C2)C3)N[C@H]1C(=O)NCCC(F)(F)F] | AND Enantiomer | MS: M/z Observed 599 |
| 123 | 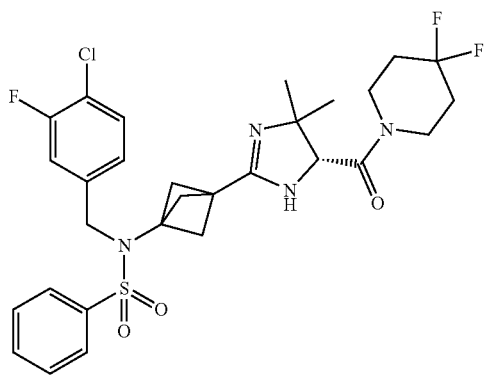 | AND Enantiomer | MS: M/z Observed 610 |
| 124 | 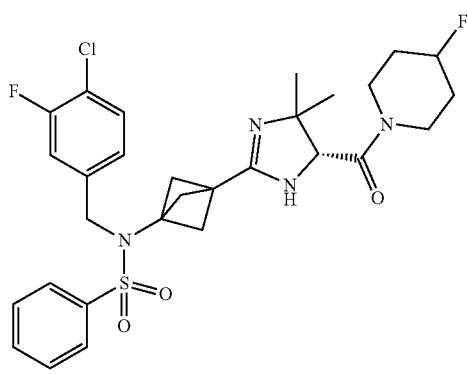 | AND Enantiomer | MS: M/z Observed 592 |

-continued
| Example Number | Structure | | Characterising Data |
|---|---|---|---|
| 125 | 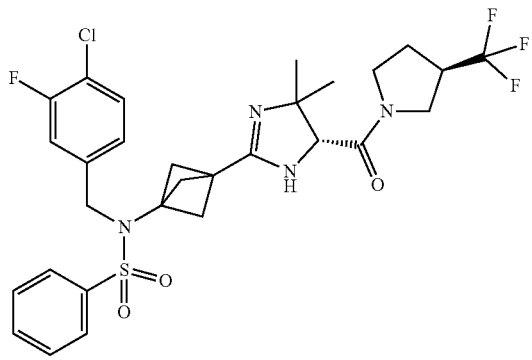 | AND Enantiomer | MS: M/z Observed 628 |
| 126 | 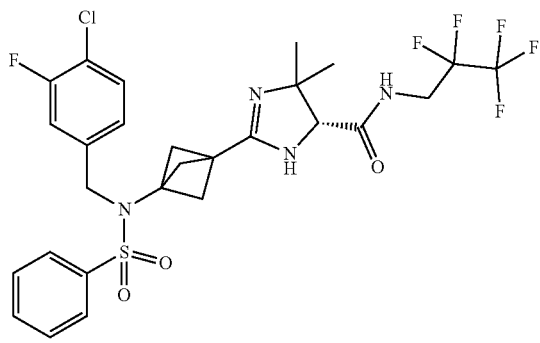 | AND Enantiomer | MS: M/z Observed 638 |
| 127 | 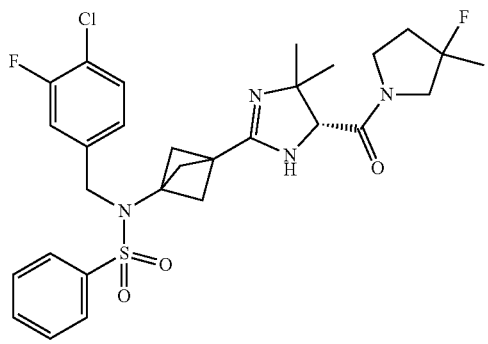 | AND Enantiomer | MS: M/z Observed 592 |

| Example Number | Structure | | Characterising Data |
|---|---|---|---|
| 128 | 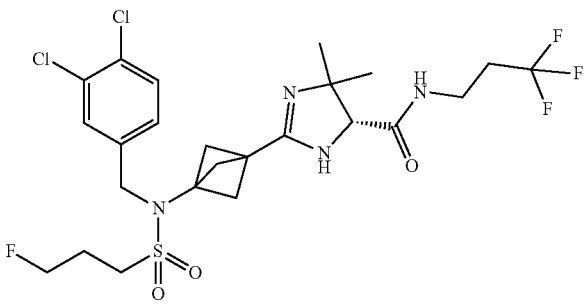 | AND Enantiomer | MS: M/z Observed 602 |
| 129 | 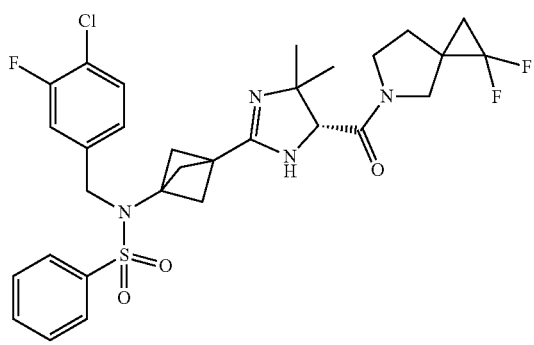 | AND Enantiomer | MS: M/z Observed 622 |
| 130 | 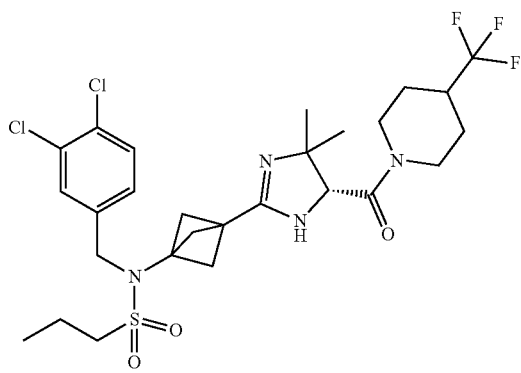 | AND Enantiomer | MS: M/z Observed 624 |
| 131 | 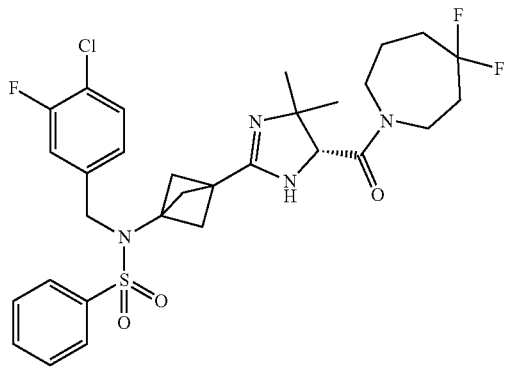 | AND Enantiomer | MS: M/z Observed 624 |

| Example Number | Structure | | Characterising Data |
|---|---|---|---|
| 132 | 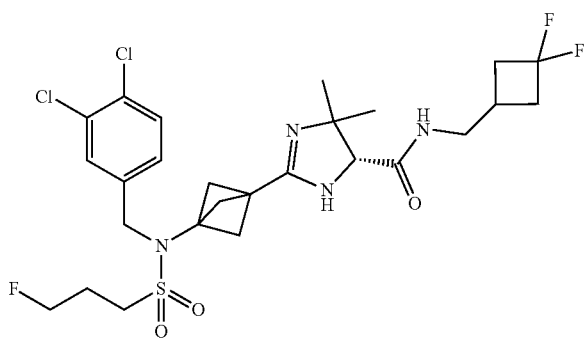 | AND Enantiomer | MS: M/z Observed 610 |
| 133 | 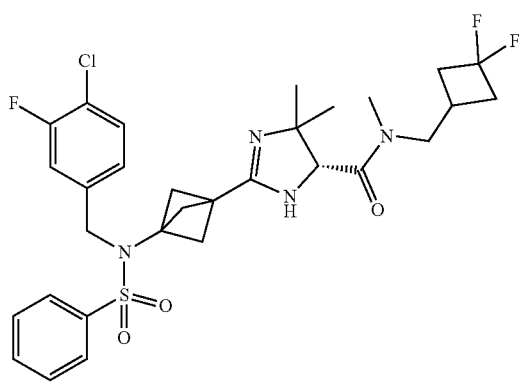 | AND Enantiomer | MS: M/z Observed 624 |
| 134 | 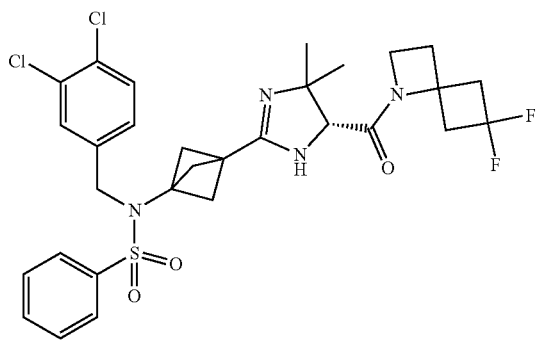 | AND Enantiomer | MS: M/z Observed 638 |

| Example Number | Structure | | Characterising Data |
|---|---|---|---|
| 135 | 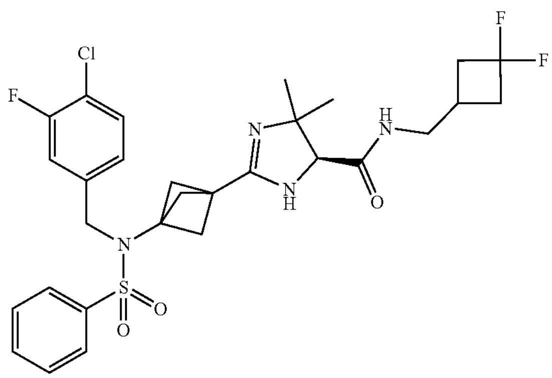 | AND Enantiomer | MS: M/z Observed 610 |
| 136 | 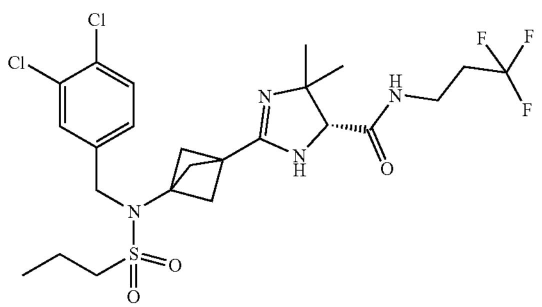 | AND Enantiomer | MS: M/z Observed 584 |
| 137 | 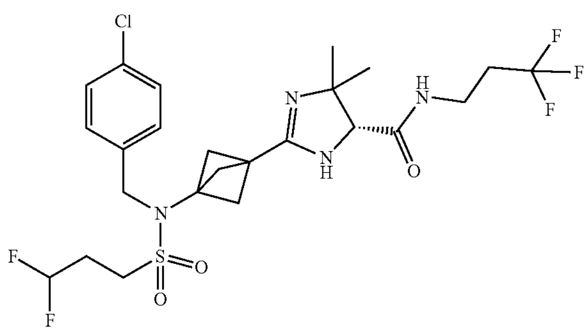 | AND Enantiomer | MS: M/z Observed 586 |
| 138 | 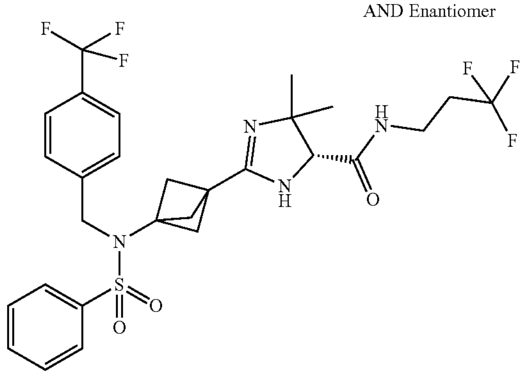 [SMILES: CC1(C)N=C(C23CC(N(Cc4ccc(C(F)(F)F)cc4)S(=O)(=O)c4ccccc4)(C2)C3)N[C@H]1C(=O)NCCC(F)(F)F] | AND Enantiomer | MS: M/z Observed 617 |

| Example Number | Structure | Characterising Data |
|---|---|---|
| 139 | AND Enantiomer 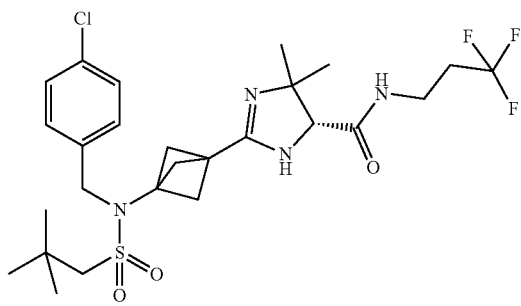 | MS: M/z Observed 578 |
| 140 | AND Enantiomer 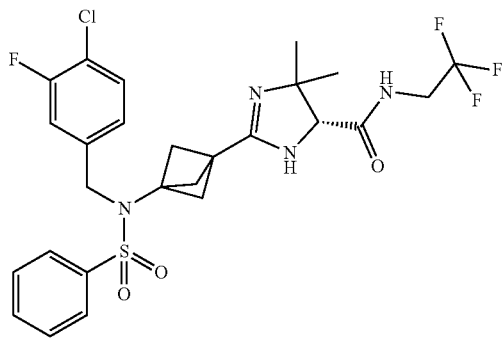 | MS: M/z Observed 588 |
| 141 | AND Enantiomer 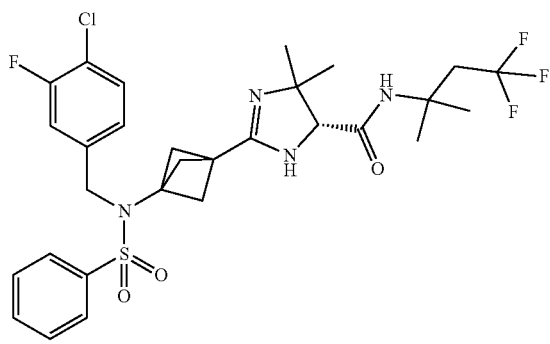 | MS: M/z Observed 630 |
| 142 | AND Enantiomer 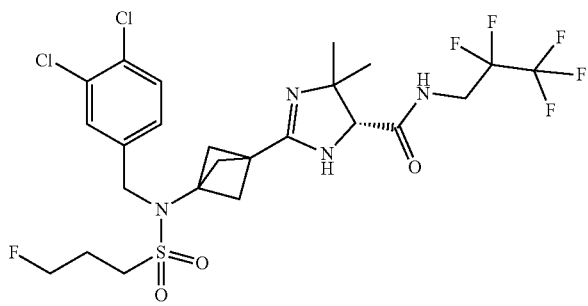 | MS: M/z Observed 638 |

| Example Number | Structure | | Characterising Data |
|---|---|---|---|
| 143 | 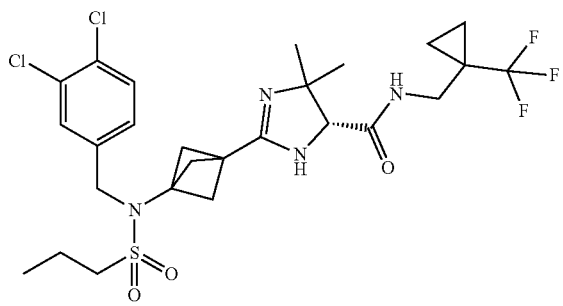 | AND Enantiomer | MS: M/z Observed 610 |
| 144 | 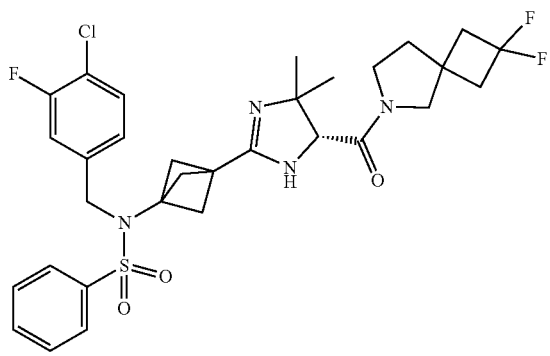 | AND Enantiomer | MS: M/z Observed 636 |
| 145 | 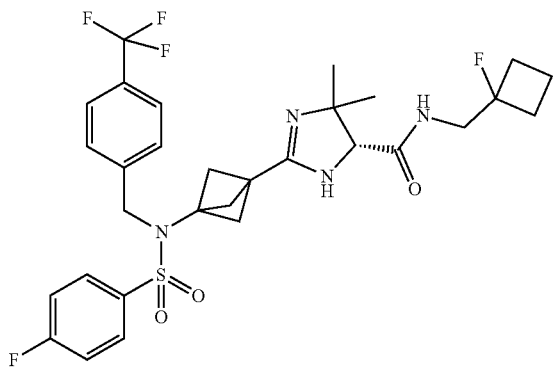 [SMILES: CC1(C)N=C(C23CC(N(Cc4ccc(C(F)(F)F)cc4)S(=O)(=O)c4ccc(F)cc4)(C2)C3)N[C@H]1C(=O)NCC1(F)CCC1] | | MS: M/z Observed 625 |
| 146 | 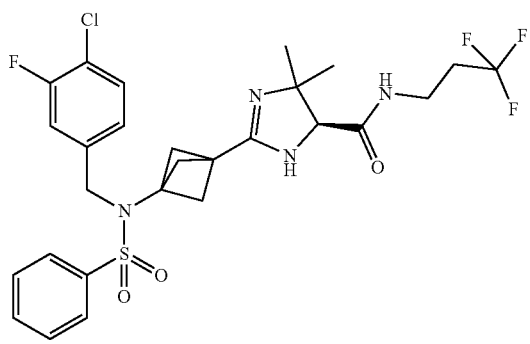 | AND Enantiomer | MS: M/z Observed 602 |

| Example Number | Structure | Characterising Data |
|---|---|---|
| 147 | 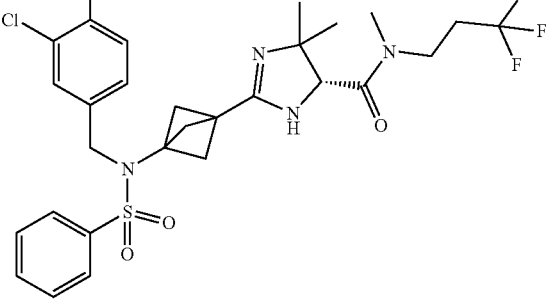 AND Enantiomer | MS: M/z Observed 632 |
| 148 | 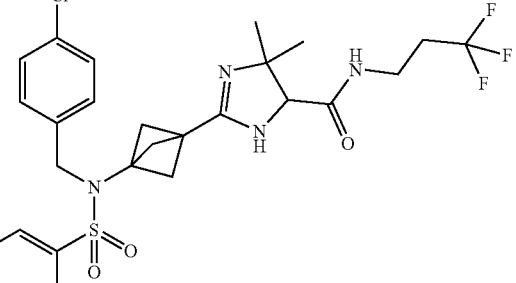 | MS: M/z Observed 584 |
| 149 | 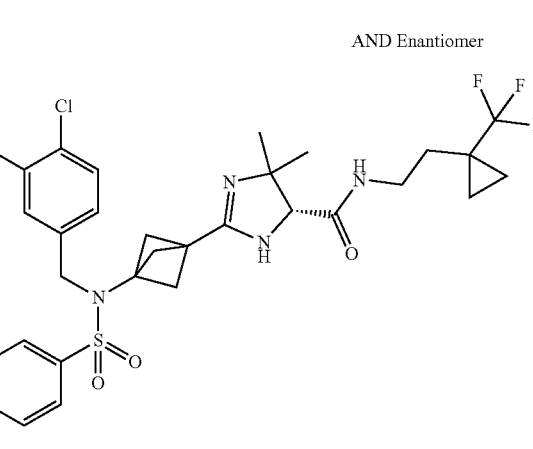 AND Enantiomer | MS: M/z Observed 642 |
| 150 | 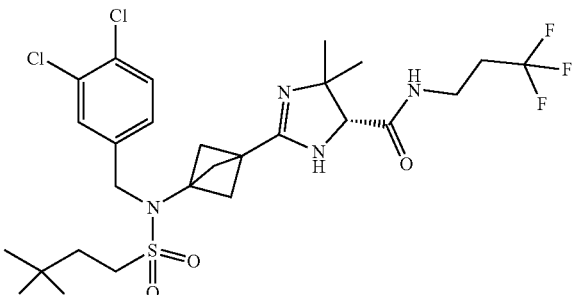 AND Enantiomer | MS: M/z Observed 634 |

| Example Number | Structure | | Characterising Data |
|---|---|---|---|
| 151 | 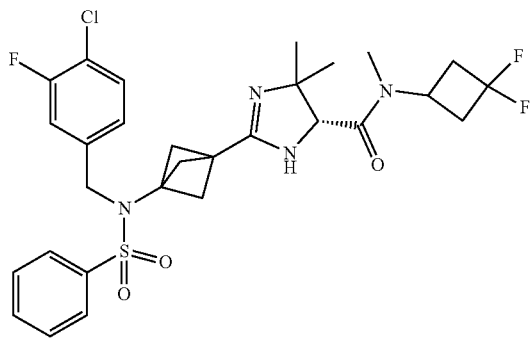 | AND Enantiomer | MS: M/z Observed 610 |
| 152 | 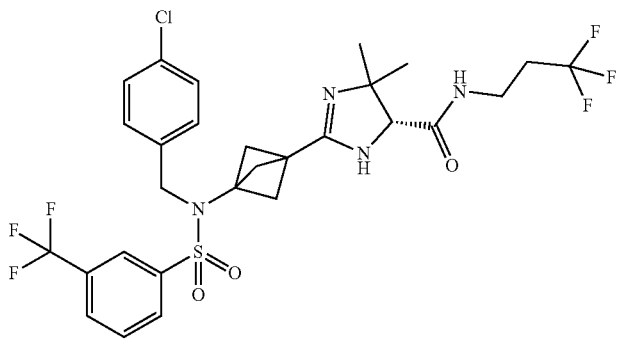 | AND Enantiomer | MS: M/z Observed 652 |
| 153 | 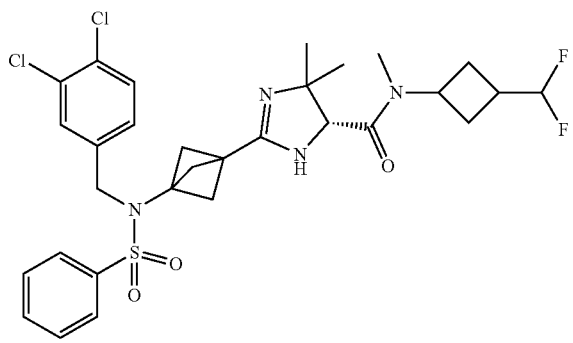 | AND Enantiomer | MS: M/z Observed 640 |
| 154 | 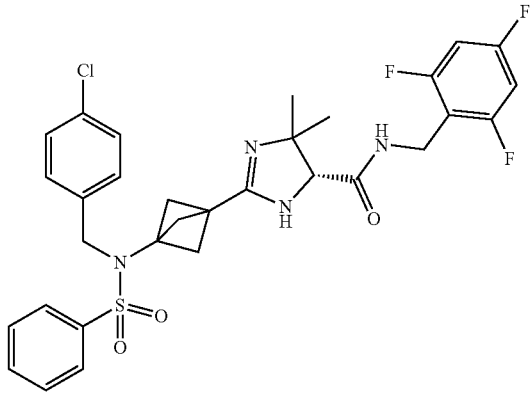 | AND Enantiomer | MS: M/z Observed 632 |

-continued
| Example Number | Structure | | Characterising Data |
|---|---|---|---|
| 155 | 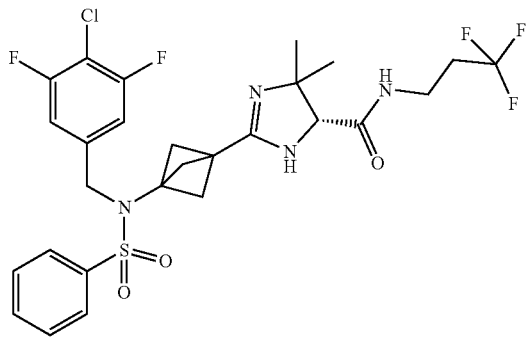 | AND Enantiomer | MS: M/z Observed 620 |
| 156 | 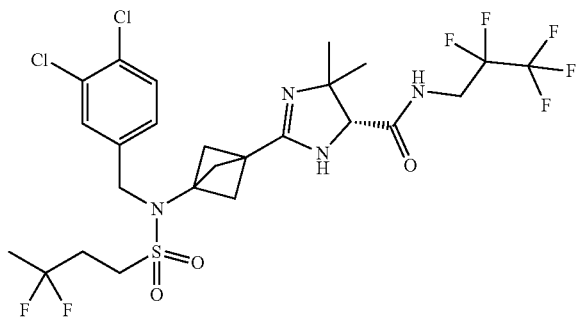 | AND Enantiomer | MS: M/z Observed 670 |
| 157 | 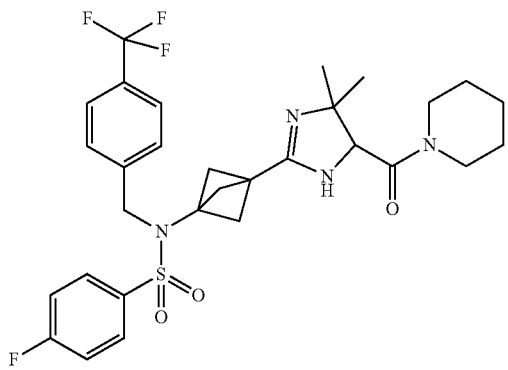 [SMILES: CC1(C)N=C(C23CC(N(Cc4ccc(C(F)(F)F)cc4)S(=O)(=O)c4ccc(F)cc4)(C2)C3)NC1C(=O)N1CCCCC1] | | MS: M/z Observed 607 |

-continued
| Example Number | Structure | Characterising Data |
|---|---|---|
| 158 | AND Enantiomer 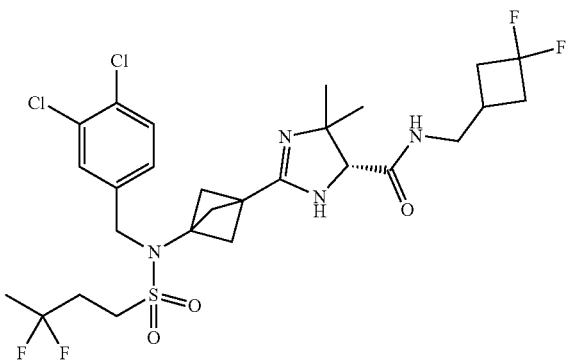 | MS: M/z Observed 642 |
| 159 | AND Enantiomer 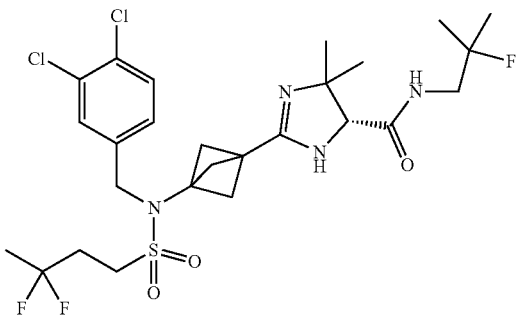 | MS: M/z Observed 612 |
| 160 | AND Enantiomer 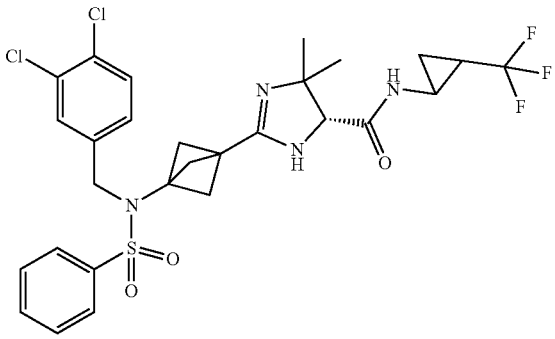 | MS: M/z Observed 630 |
| 161 | 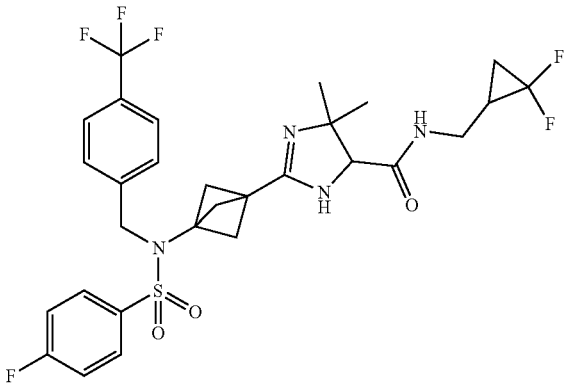 [SMILES: CC1(C)N=C(C23CC(N(Cc4ccc(C(F)(F)F)cc4)S(=O)(=O)c4ccc(F)cc4)(C2)C3)NC1C(=O)NCC1CC1(F)F] | MS: M/z Observed 629 |

| Example Number | Structure | Characterising Data |
|---|---|---|
| 162 | AND Enantiomer 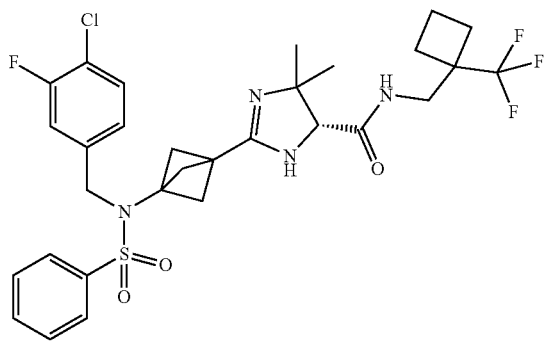 | MS: M/z Observed 642 |
| 163 | AND Enantiomer 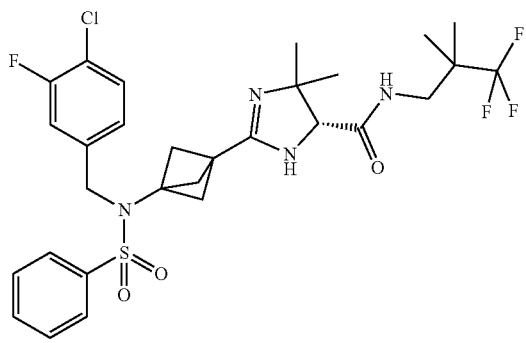 | MS: M/z Observed 630 |
| 164 | 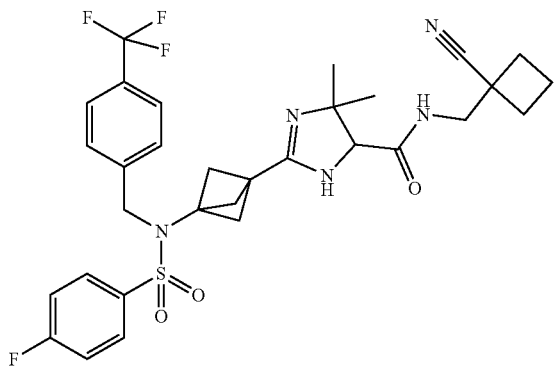 [SMILES: CC1(C)N=C(C23CC(N(Cc4ccc(C(F)(F)F)cc4)S(=O)(=O)c4ccc(F)cc4)(C2)C3)NC1C(=O)NCC1(C#N)CCC1] | MS: M/z Observed 632 |
| 165 | AND Enantiomer 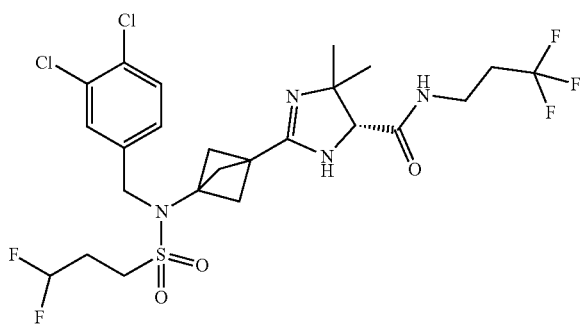 | MS: M/z Observed 620 |

| Example Number | Structure | Characterising Data |
|---|---|---|
| 166 | AND Enantiomer 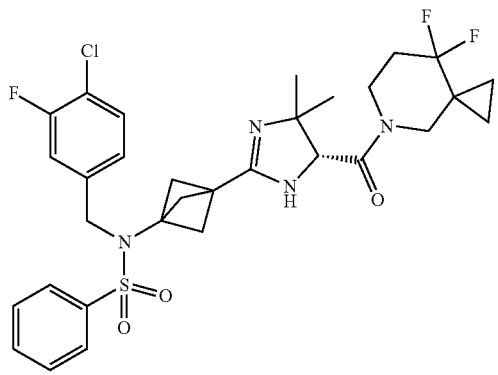 | MS: M/z Observed 636 |
| 167 | AND Enantiomer 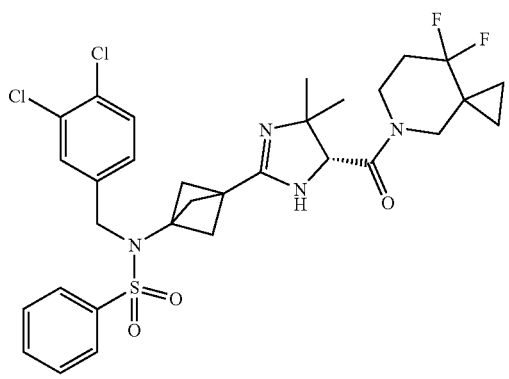 | MS: M/z Observed 652 |
| 168 | AND Enantiomer 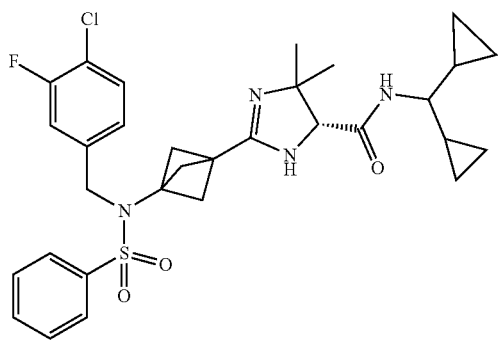 | MS: M/z Observed 600 |

-continued
| Example Number | Structure | Characterising Data |
|---|---|---|
| 169 | AND Enantiomer 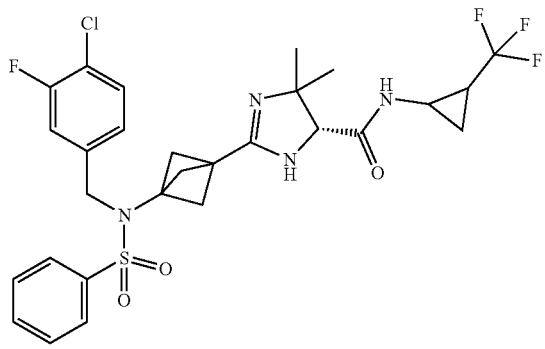 | MS: M/z Observed 614 |
| 170 | AND Enantiomer 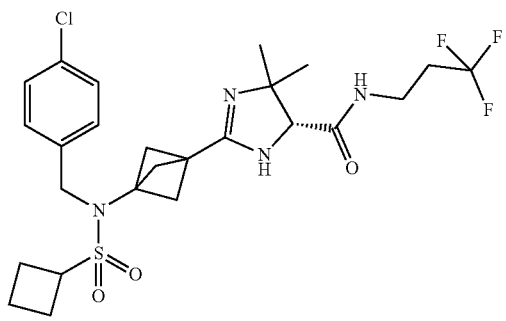 | MS: M/z Observed 562 |
| 171 | AND Enantiomer 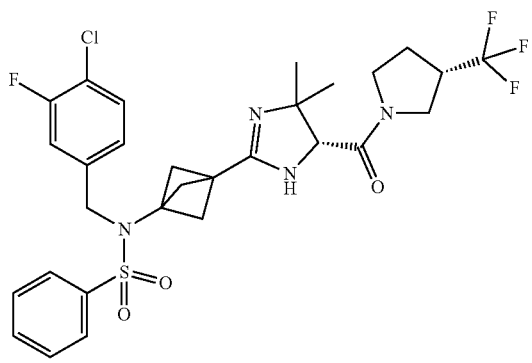 | MS: M/z Observed 628 |

-continued
| Example Number | Structure | Characterising Data |
|---|---|---|
| 172 | AND Enantiomer 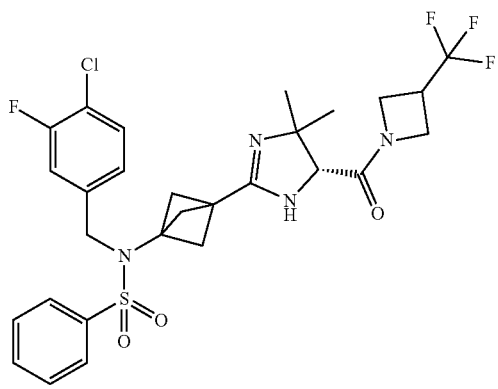 | MS: M/z Observed 614 |
| 173 | HCl  AND Enantiomer 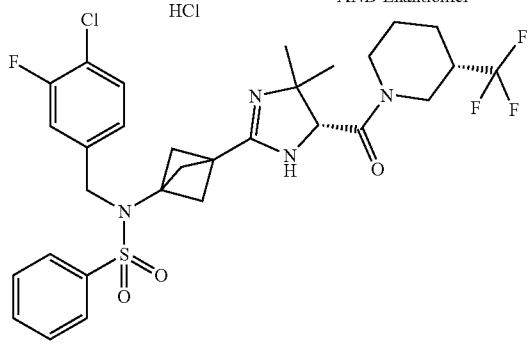 | MS: M/z Observed 678 |
| 174 | AND Enantiomer 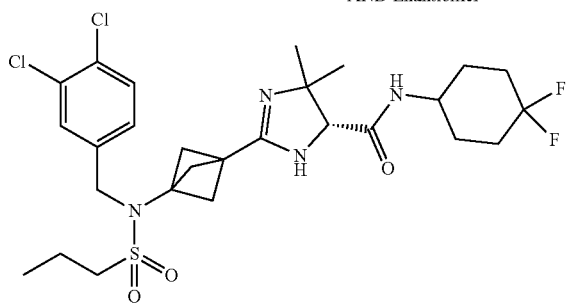 | MS: M/z Observed 606 |
| 175 | AND Enantiomer 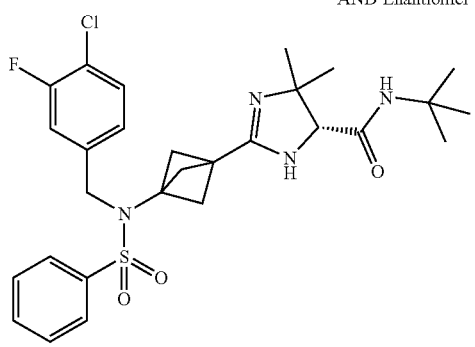 | MS: M/z Observed 562 |

| Example Number | Structure | | Characterising Data |
|---|---|---|---|
| 176 | 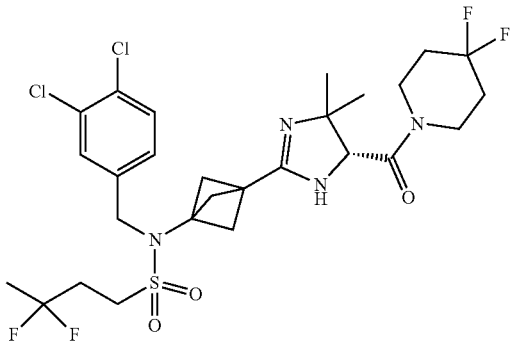 | AND Enantiomer | MS: M/z Observed 642 |
| 177 | 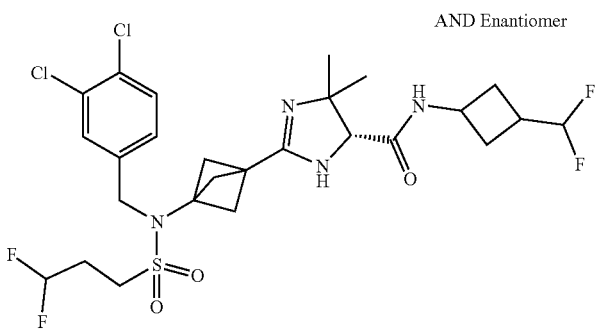 [SMILES: CC1(C)N=C(C23CC(N(Cc4ccc(Cl)c(Cl)c4)S(=O)(=O)CCC(F)F)(C2)C3)N[C@H]1C(=O)NC1CC(C(F)F)C1] | AND Enantiomer | MS: M/z Observed 628 |
| 178 | 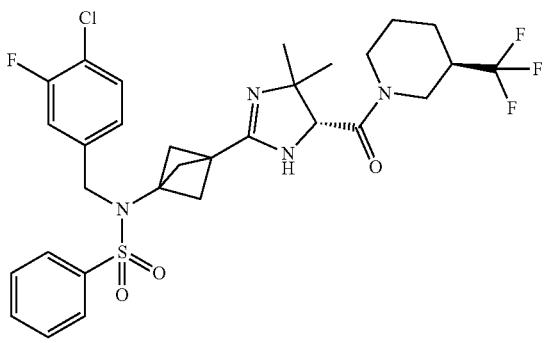 | AND Enantiomer | MS: M/z Observed 642 |
| 179 | 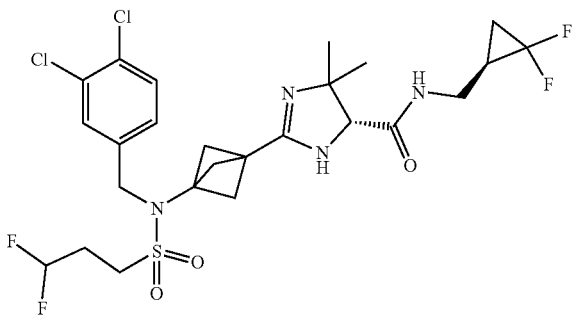 | AND Enantiomer | MS: M/z Observed 614 |

-continued
| Example Number | Structure | | Characterising Data |
|---|---|---|---|
| 180 | 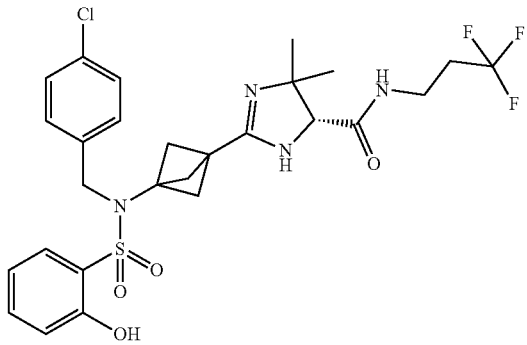 | AND Enantiomer | MS: M/z Observed 600 |
| 181 | 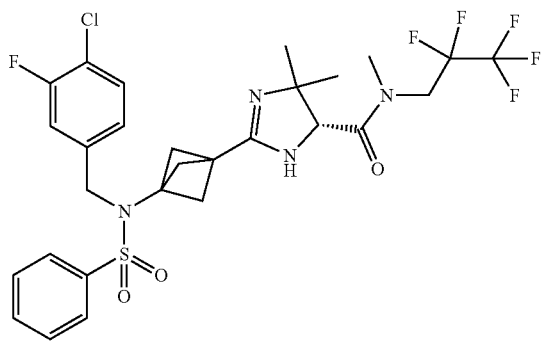 | AND Enantiomer | MS: M/z Observed 652 |
| 182 | 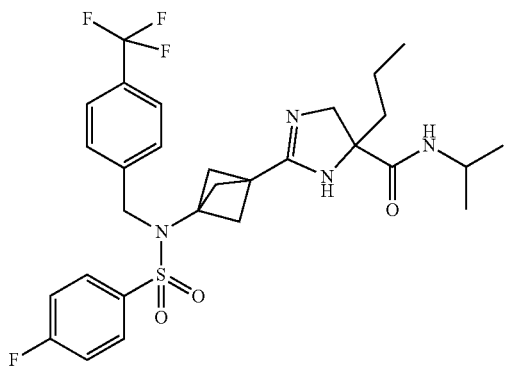 [SMILES: CCCC1(C(=O)NC(C)C)CN=C(C23CC(N(Cc4ccc(C(F)(F)F)cc4)S(=O)(=O)c4ccc(F)cc4)(C2)C3)N1] | | MS: M/z Observed 595 |
| 183 | 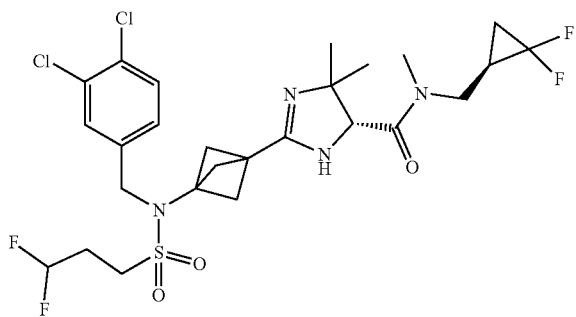 | AND Enantiomer | MS: M/z Observed 628 |

| Example Number | Structure | Characterising Data |
|---|---|---|
| 184 | 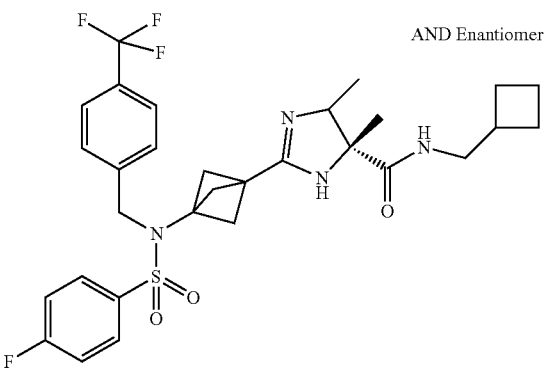 [SMILES: CC1N=C(C23CC(N(Cc4ccc(C(F)(F)F)cc4)S(=O)(=O)c4ccc(F)cc4)(C2)C3)N[C@@]1(C)C(=O)NCC1CCC1] AND Enantiomer | MS: M/z Observed 607 |
| 185 | 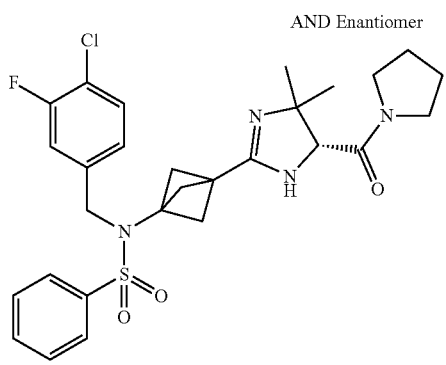 [SMILES: CC1(C)N=C(C23CC(N(Cc4ccc(Cl)c(F)c4)S(=O)(=O)c4ccccc4)(C2)C3)N[C@H]1C(=O)N1CCCC1] AND Enantiomer | MS: M/z Observed 560 |
| 186 | 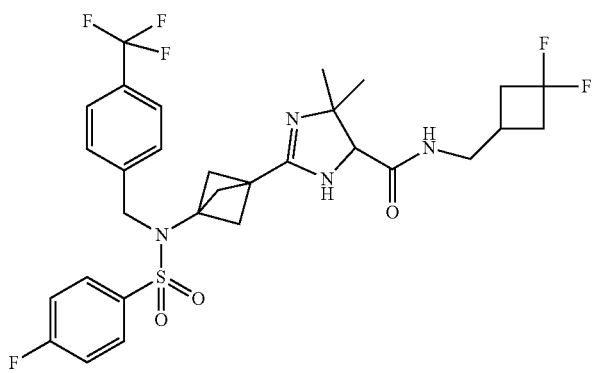 [SMILES: CC1(C)N=C(C23CC(N(Cc4ccc(C(F)(F)F)cc4)S(=O)(=O)c4ccc(F)cc4)(C2)C3)NC1C(=O)NCC1CC(F)(F)C1] | MS: M/z Observed 643 |
| 187 | 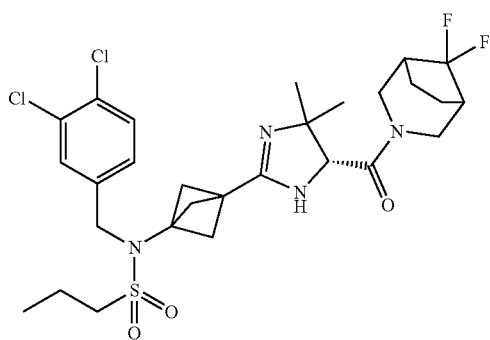 AND Enantiomer | MS: M/z Observed 618 |

-continued
| Example Number | Structure | Characterising Data |
|---|---|---|
| 188 | AND Enantiomer 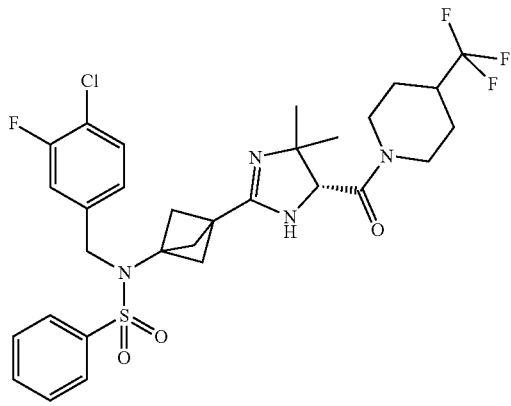 | MS: M/z Observed 642 |
| 189 | AND Enantiomer 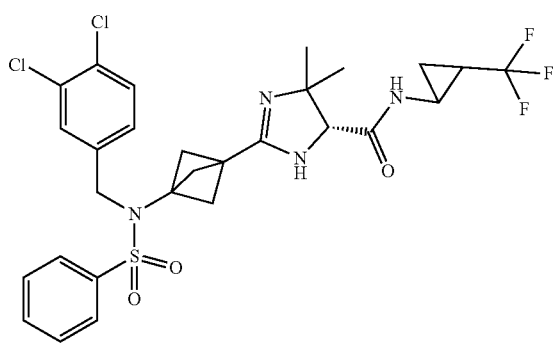 | MS: M/z Observed 630 |
| 190 | AND Enantiomer 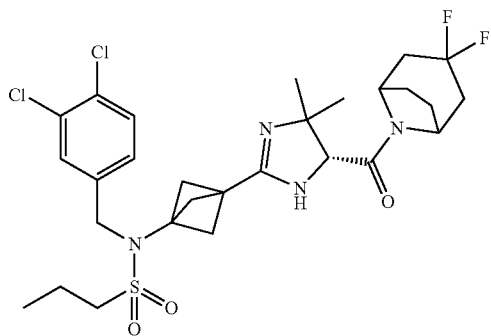 | MS: M/z Observed 618 |

-continued

| Example Number | Structure | Characterising Data |
|---|---|---|
| 191 | AND Enantiomer | MS: M/z Observed 629 |
| 192 | 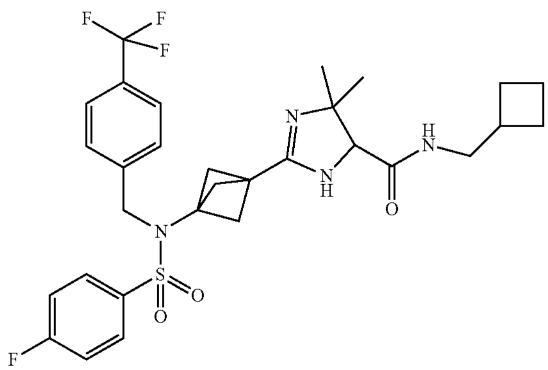 [SMILES: CC1(C)N=C(C23CC(N(Cc4ccc(C(F)(F)F)cc4)S(=O)(=O)c4ccc(F)cc4)(C2)C3)NC1C(=O)NCC1CCC1] | MS: M/z Observed 607 |
| 193 | 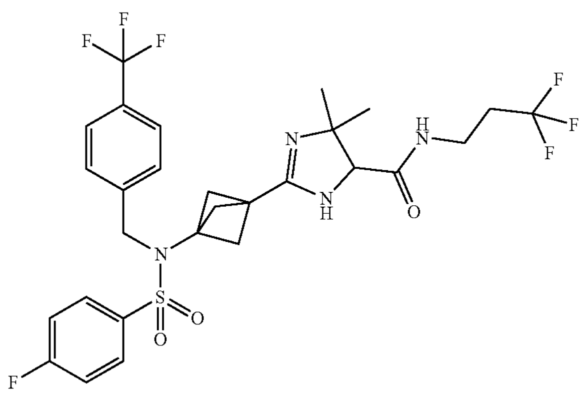 [SMILES: CC1(C)N=C(C23CC(N(Cc4ccc(C(F)(F)F)cc4)S(=O)(=O)c4ccc(F)cc4)(C2)C3)NC1C(=O)NCCC(F)(F)F] | MS: M/z Observed 635 |
| 194 | AND Enantiomer | MS: M/z Observed 628 |

-continued

| Example Number | Structure | Characterising Data |
|---|---|---|
| 195 | AND Enantiomer | MS: M/z Observed 638 |
| 196 | AND Enantiomer | MS: M/z Observed 567 |
| 197 | AND Enantiomer | MS: M/z Observed 635 |
| 198 | AND Enantiomer | MS: M/z Observed 622 |

-continued
| Example Number | Structure | Characterising Data |
|---|---|---|
| 199 | 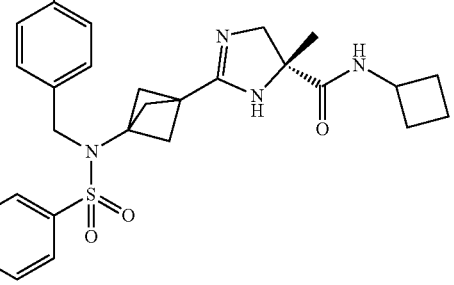 AND Enantiomer | MS: M/z Observed 579 |
| 200 | 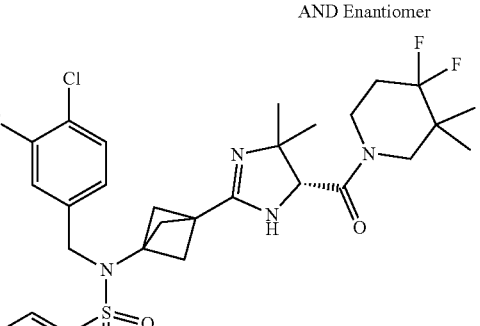 AND Enantiomer | MS: M/z Observed 638 |
| 201 | 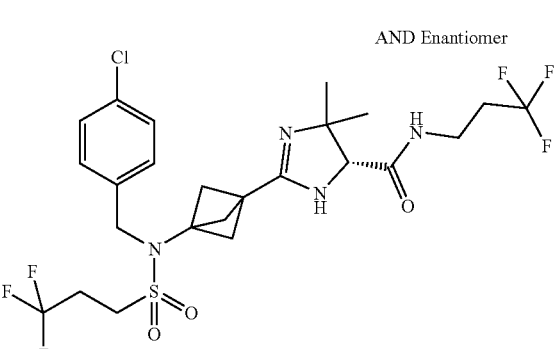 AND Enantiomer | MS: M/z Observed 604 |
| 202 | 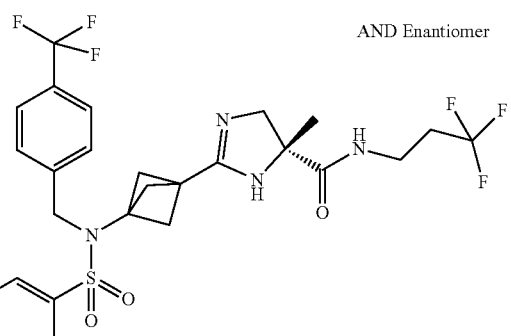 AND Enantiomer | MS: M/z Observed 621 |

| Example Number | Structure | | Characterising Data |
|---|---|---|---|
| 203 | 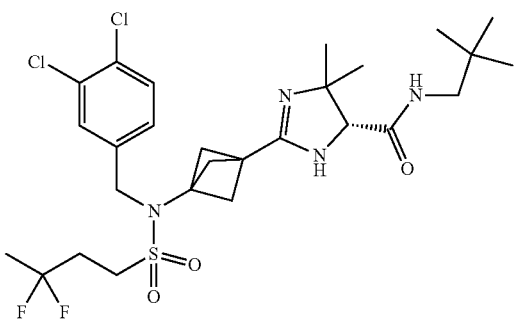 | AND Enantiomer | MS: M/z Observed 608 |
| 204 | 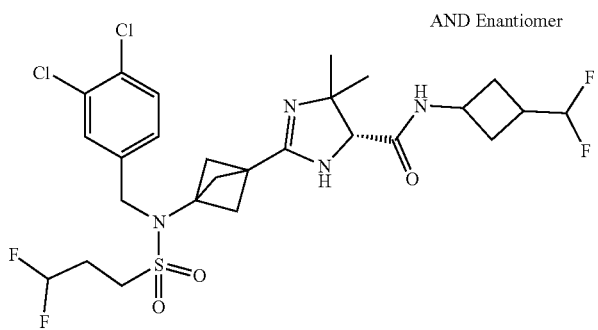 [SMILES: CC1(C)N=C(C23CC(N(Cc4ccc(Cl)c(Cl)c4)S(=O)(=O)CCC(F)F)(C2)C3)N[C@H]1C(=O)NC1CC(C(F)F)C1] | AND Enantiomer | MS: M/z Observed 628 |
| 205 | 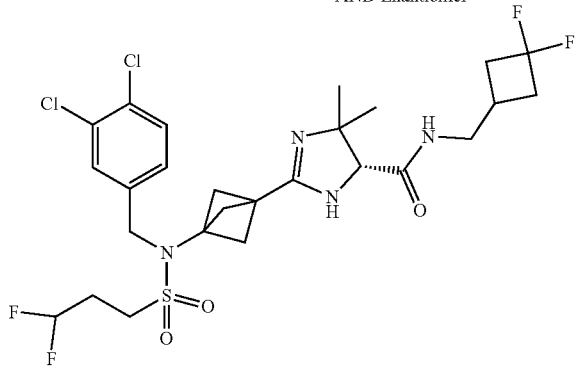 | AND Enantiomer | MS: M/z Observed 628 |
| 206 | 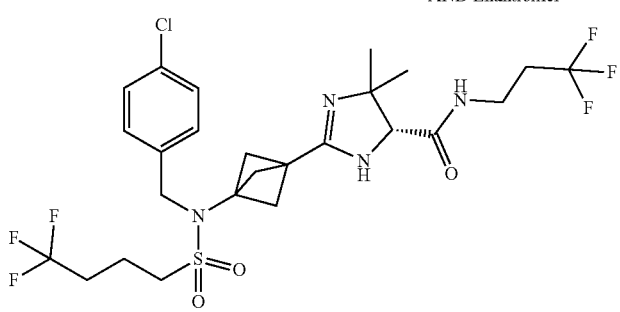 | AND Enantiomer | MS: M/z Observed 618 |

| Example Number | Structure | | Characterising Data |
|---|---|---|---|
| 207 | 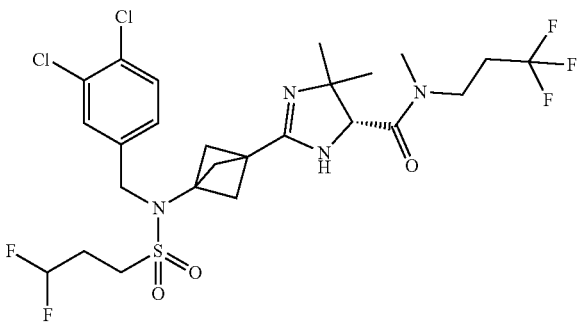 | AND Enantiomer | MS: M/z Observed 634 |
| 208 | 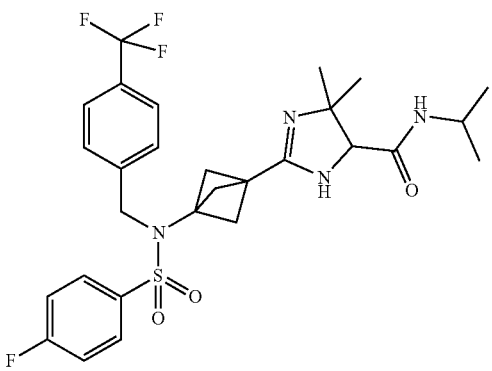 [SMILES: CC(C)NC(=O)C1NC(C23CC(N(Cc4ccc(C(F)(F)F)cc4)S(=O)(=O)c4ccc(F)cc4)(C2)C3)=NC1(C)C] | | MS: M/z Observed 581 |
| 209 | 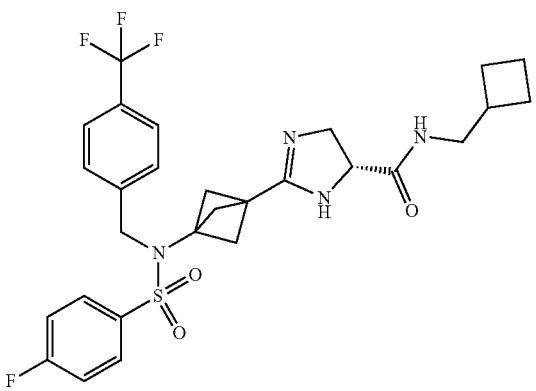 | AND Enantiomer | MS: M/z Observed 579 |
| 210 | 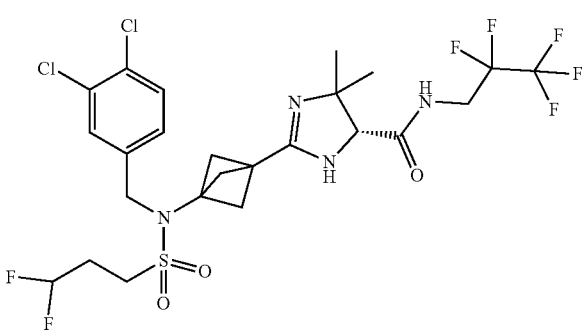 | AND Enantiomer | MS: M/z Observed 656 |

| Example Number | Structure | Characterising Data |
|---|---|---|
| 211 | 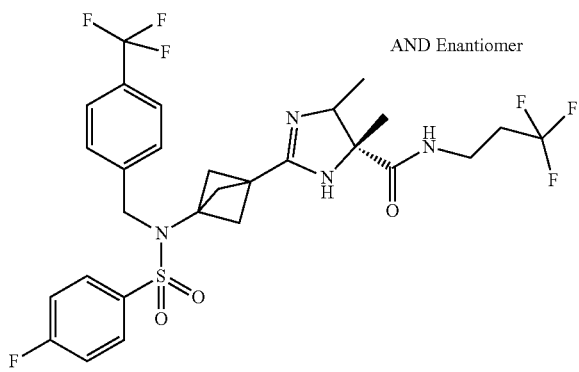 [SMILES: CC1N=C(C23CC(N(Cc4ccc(C(F)(F)F)cc4)S(=O)(=O)c4ccc(F)cc4)(C2)C3)N[C@@]1(C)C(=O)NCCC(F)(F)F] AND Enantiomer | MS: M/z Observed 635 |
| 212 | 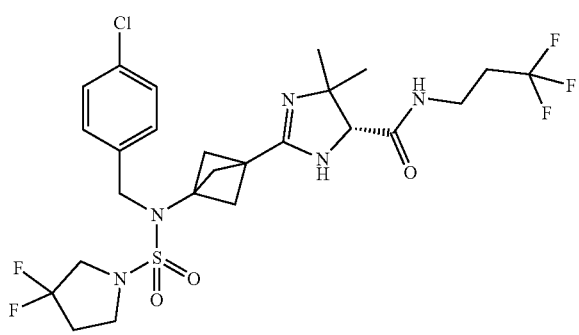 AND Enantiomer | MS: M/z Observed 613 |
| 213 | 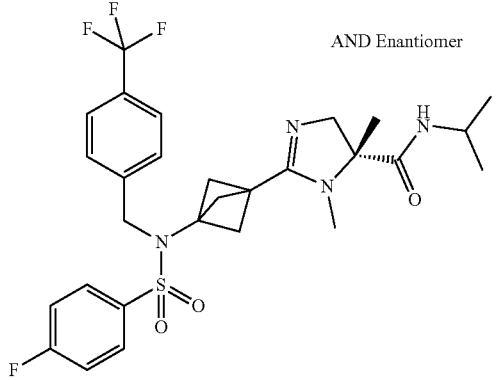 [SMILES: CC(C)NC(=O)[C@@]1(C)CN=C(C23CC(N(Cc4ccc(C(F)(F)F)cc4)S(=O)(=O)c4ccc(F)cc4)(C2)C3)N1C] AND Enantiomer | MS: M/z Observed 581 |
| 214 | 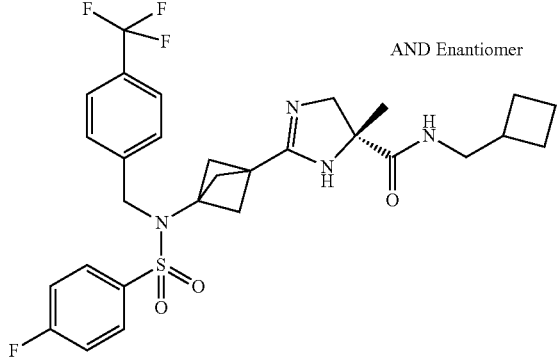 [SMILES: C[C@]1(C(=O)NCC2CCC2)CN=C(C23CC(N(Cc4ccc(C(F)(F)F)cc4)S(=O)(=O)c4ccc(F)cc4)(C2)C3)N1] AND Enantiomer | MS: M/z Observed 593 |

-continued
| Example Number | Structure | | Characterising Data |
|---|---|---|---|
| 215 | 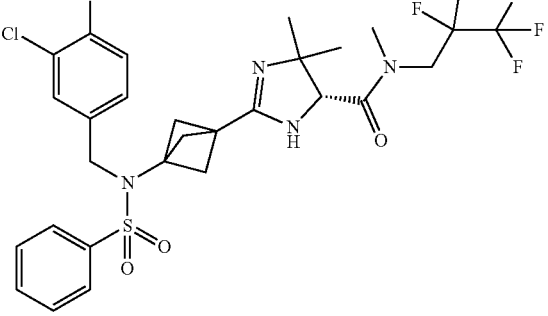 | AND Enantiomer | MS: M/z Observed 668 |
| 216 | 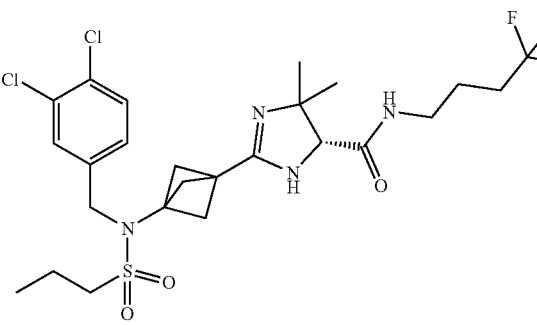 | AND Enantiomer | MS: M/z Observed 598 |
| 217 | 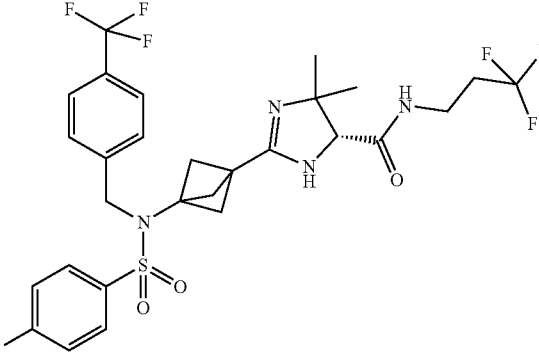 | AND Enantiomer | MS: M/z Observed 635 |
| 218 | 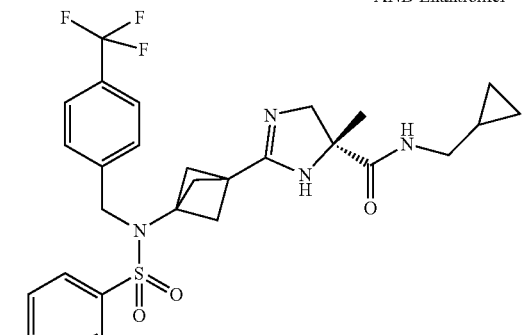 | AND Enantiomer | MS: M/z Observed 579 |

-continued
| Example Number | Structure | | Characterising Data |
|---|---|---|---|
| 219 | 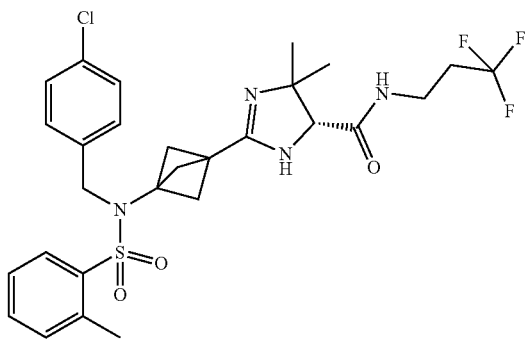 | AND Enantiomer | MS: M/z Observed 598 |
| 220 | 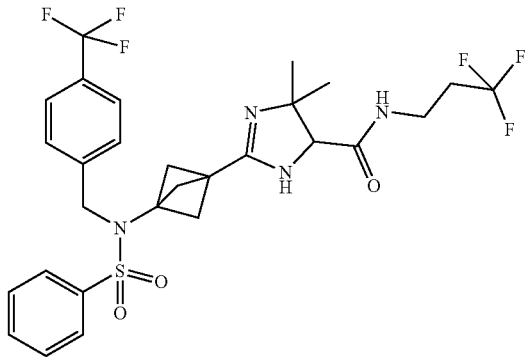 [SMILES: CC1(C)N=C(C23CC(N(Cc4ccc(C(F)(F)F)cc4)S(=O)(=O)c4ccccc4)(C2)C3)NC1C(=O)NCCC(F)(F)F] | | MS: M/z Observed 617 |
| 221 | 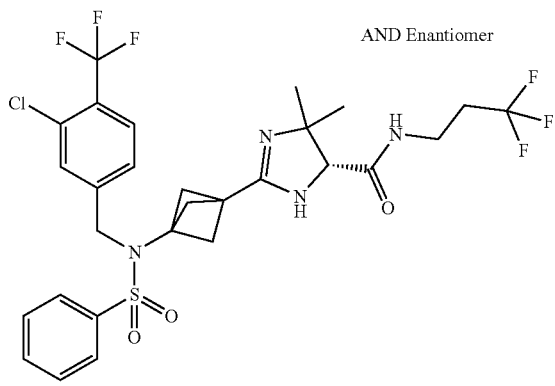 [SMILES: CC1(C)N=C(C23CC(N(Cc4ccc(C(F)(F)F)c(Cl)c4)S(=O)(=O)c4ccccc4)(C2)C3)N[C@H]1C(=O)NCCC(F)(F)F] | AND Enantiomer | MS: M/z Observed 652 |
| 222 | 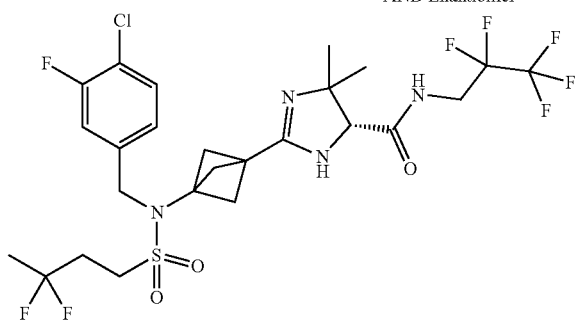 | AND Enantiomer | MS: M/z Observed 654 |

| Example Number | Structure | | Characterising Data |
|---|---|---|---|
| 223 | 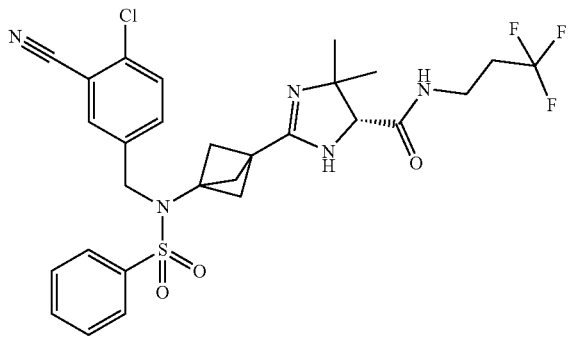 | AND Enantiomer | MS: M/z Observed 609 |
| 224 | 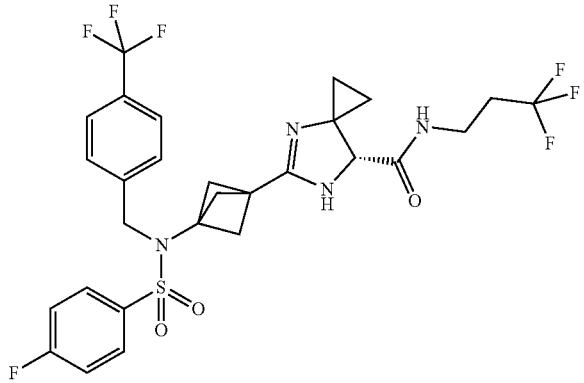 [SMILES: O=C(NCCC(F)(F)F)[C@@H]1NC(C23CC(N(Cc4ccc(C(F)(F)F)cc4)S(=O)(=O)c4ccc(F)cc4)(C2)C3)=NC12CC2] | | MS: M/z Observed 633 |
| 225 | 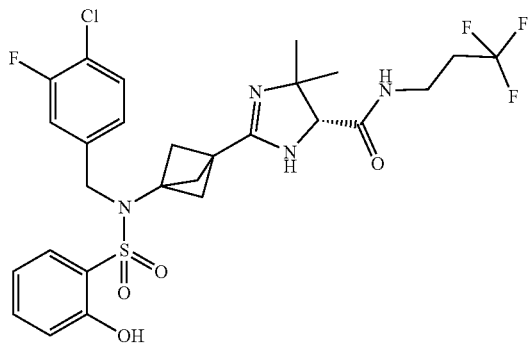 | AND Enantiomer | MS: M/z Observed 618 |
| 226 | 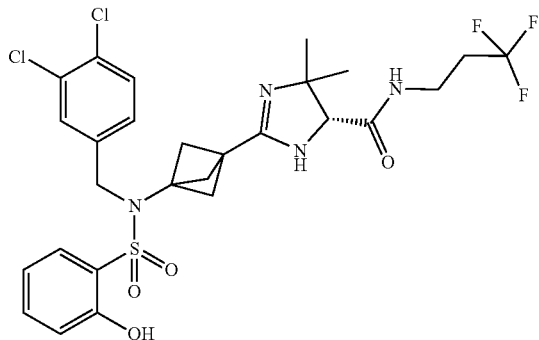 | AND Enantiomer | MS: M/z Observed 634 |

| Example Number | Structure | Characterising Data |
|---|---|---|
| 227 | 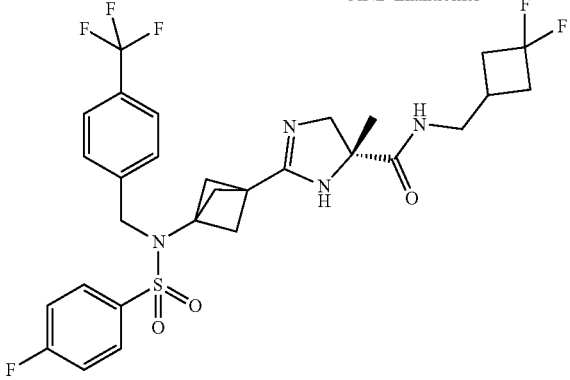 AND Enantiomer | MS: M/z Observed 629 |
| 228 | 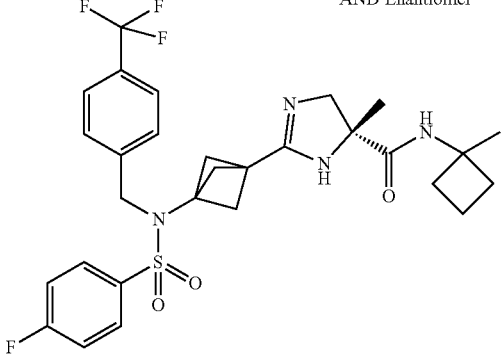 AND Enantiomer | MS: M/z Observed 593 |
| 229 | 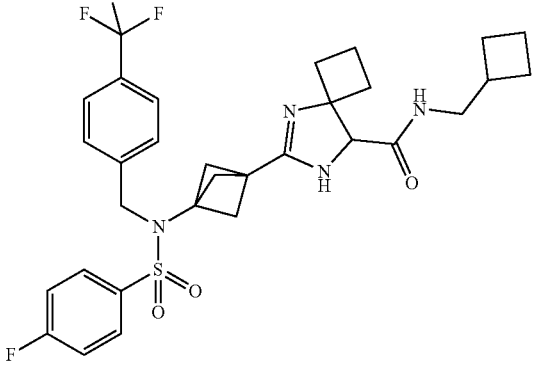 | MS: M/z Observed 619 |
| 230 | 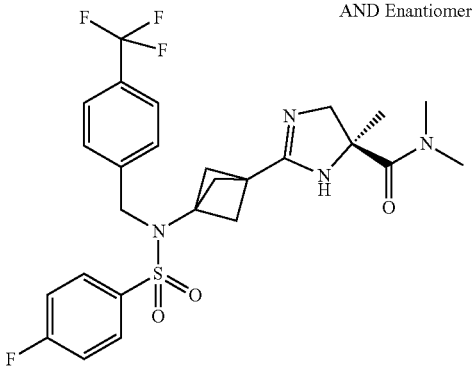 [SMILES: CN(C)C(=O)[C@]1(C)CN=C(C23CC(N(Cc4ccc(C(F)(F)F)cc4)S(=O)(=O)c4ccc(F)cc4)(C2)C3)N1] AND Enantiomer | MS: M/z Observed 553 |

-continued
| Example Number | Structure | Characterising Data |
|---|---|---|
| 231 | 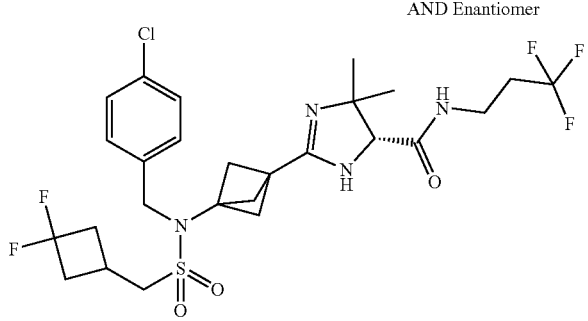 [SMILES: CC1(C)N=C(C23CC(N(Cc4ccc(Cl)cc4)S(=O)(=O)CC4CC(F)(F)C4)(C2)C3)N[C@H]1C(=O)NCCC(F)(F)F] AND Enantiomer | MS: M/z Observed 612 |
| 232 | 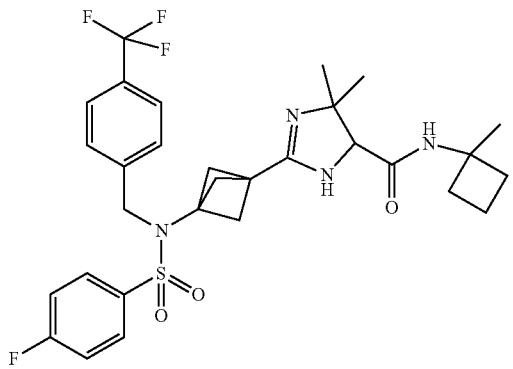 [SMILES: CC1(NC(=O)C2NC(C34CC(N(Cc5ccc(C(F)(F)F)cc5)S(=O)(=O)c5ccc(F)cc5)(C3)C4)=NC2(C)C)CCC1] | MS: M/z Observed 607 |
| 233 | 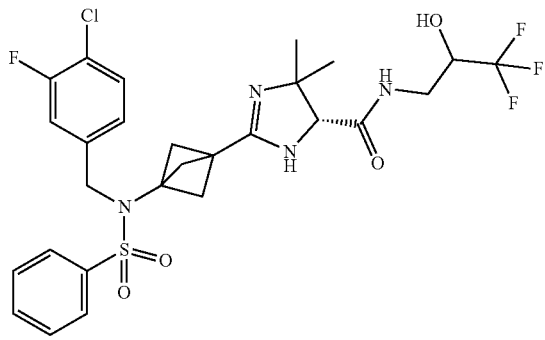 AND Enantiomer | MS: M/z Observed 618 |
| 234 | 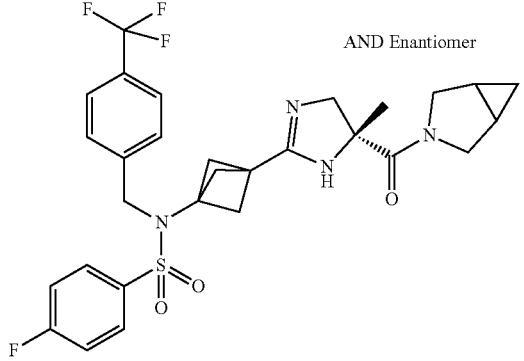 [SMILES: C[C@]1(C(=O)N2CC3CC3C2)CN=C(C23CC(N(Cc4ccc(C(F)(F)F)cc4)S(=O)(=O)c4ccc(F)cc4)(C2)C3)N1] AND Enantiomer | MS: M/z Observed 591 |

| Example Number | Structure | | Characterising Data |
|---|---|---|---|
| 235 | 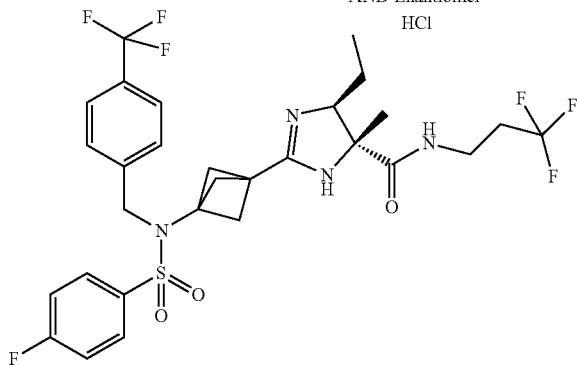 | AND Enantiomer HCl | MS: M/z Observed 686 |
| 236 | 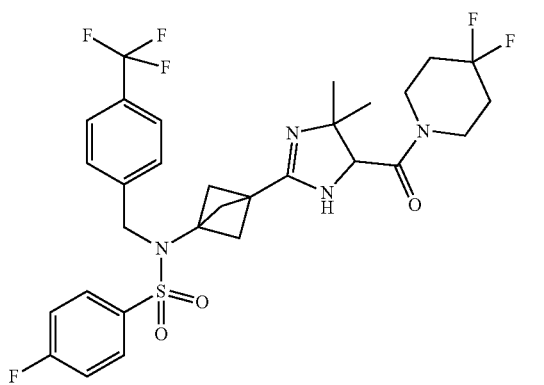 [SMILES: CC1(C)N=C(C23CC(N(Cc4ccc(C(F)(F)F)cc4)S(=O)(=O)c4ccc(F)cc4)(C2)C3)NC1C(=O)N1CCC(F)(F)CC1] | | MS: M/z Observed 643 |
| 237 | 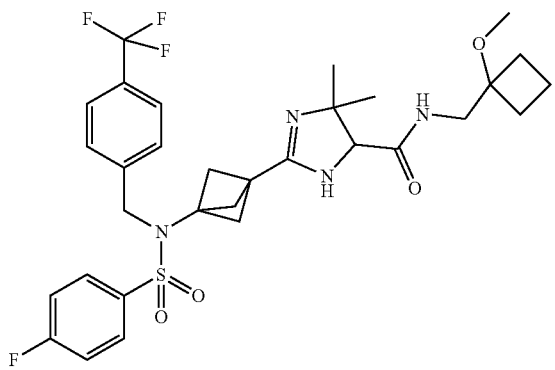 [SMILES: COC1(CNC(=O)C2NC(C34CC(N(Cc5ccc(C(F)(F)F)cc5)S(=O)(=O)c5ccc(F)cc5)(C3)C4)=NC2(C)C)CCC1] | | MS: M/z Observed 637 |
| 238 | 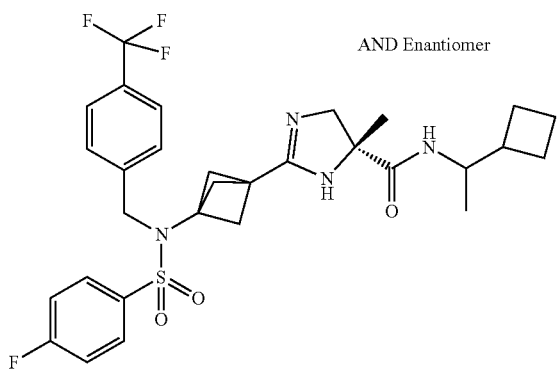 [SMILES: CC(NC(=O)[C@@]1(C)CN=C(C23CC(N(Cc4ccc(C(F)(F)F)cc4)S(=O)(=O)c4ccc(F)cc4)(C2)C3)N1)C1CCC1] | AND Enantiomer | MS: M/z Observed 607 |

| Example Number | Structure | Characterising Data |
|---|---|---|
| 239 | 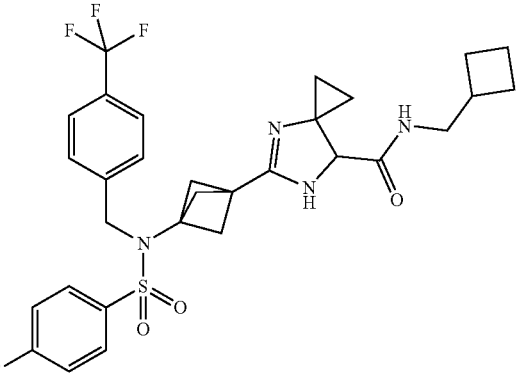 | MS: M/z Observed 605 |
| 240 | 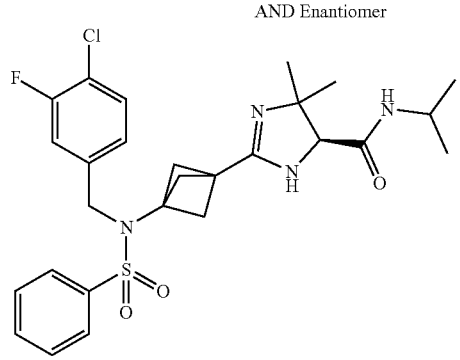 [SMILES: CC(C)NC(=O)[C@H]1NC(C23CC(N(Cc4ccc(Cl)c(F)c4)S(=O)(=O)c4ccccc4)(C2)C3)=NC1(C)C] AND Enantiomer | MS: M/z Observed 548 |
| 241 | 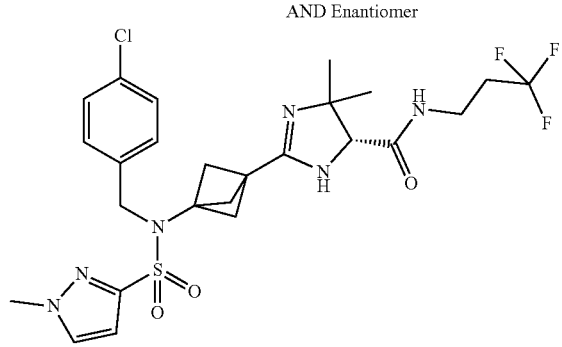 [SMILES: Cn1ccc(S(=O)(=O)N(Cc2ccc(Cl)cc2)C23CC(C4=NC(C)(C)[C@H](C(=O)NCCC(F)(F)F)N4)(C2)C3)n1] AND Enantiomer | MS: M/z Observed 588 |
| 242 | 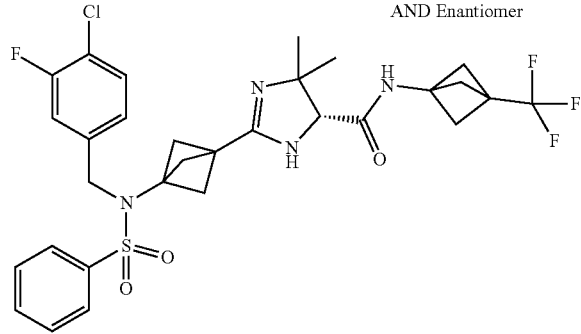 [SMILES: CC1(C)N=C(C23CC(N(Cc4ccc(Cl)c(F)c4)S(=O)(=O)c4ccccc4)(C2)C3)N[C@H]1C(=O)NC12CC(C(F)(F)F)(C1)C2] AND Enantiomer | MS: M/z Observed 640 |

| Example Number | Structure | Characterising Data |
|---|---|---|
| 243 | 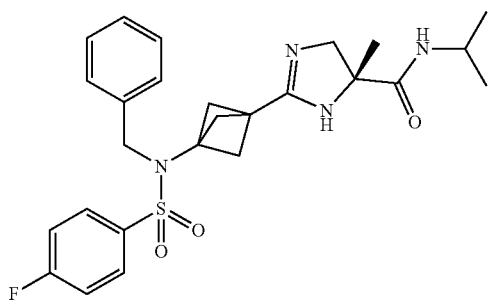 AND Enantiomer | MS: M/z Observed 499 |
| 244 | 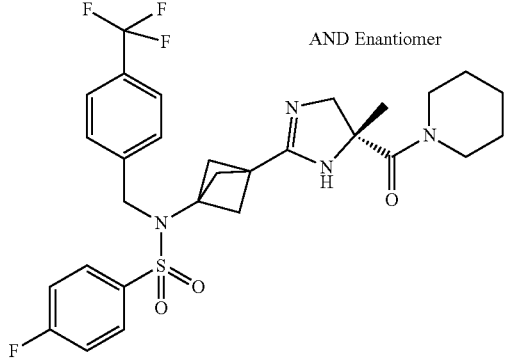 [SMILES: C[C@]1(C(=O)N2CCCCC2)CN=C(C23CC(N(Cc4ccc(C(F)(F)F)cc4)S(=O)(=O)c4ccc(F)cc4)(C2)C3)N1] AND Enantiomer | MS: M/z Observed 593 |
| 245 | 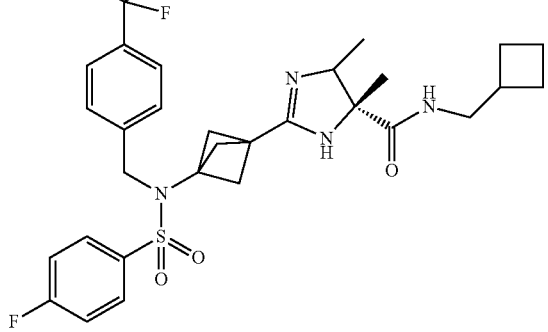 AND Enantiomer | MS: M/z Observed 607 |
| 246 | 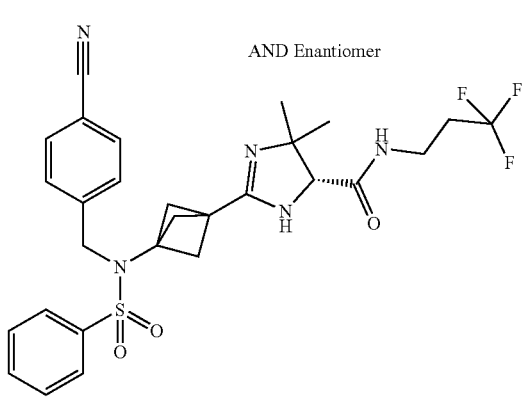 [SMILES: CC1(C)N=C(C23CC(N(Cc4ccc(C#N)cc4)S(=O)(=O)c4ccccc4)(C2)C3)N[C@H]1C(=O)NCCC(F)(F)F] AND Enantiomer | MS: M/z Observed 574 |

| Example Number | Structure | Characterising Data |
|---|---|---|
| 247 | 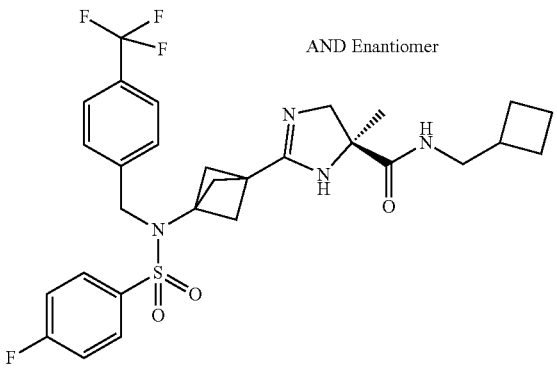 [SMILES: C[C@@]1(C(=O)NCC2CCC2)CN=C(C23CC(N(Cc4ccc(C(F)(F)F)cc4)S(=O)(=O)c4ccc(F)cc4)(C2)C3)N1] AND Enantiomer | MS: M/z Observed 593 |
| 248 | 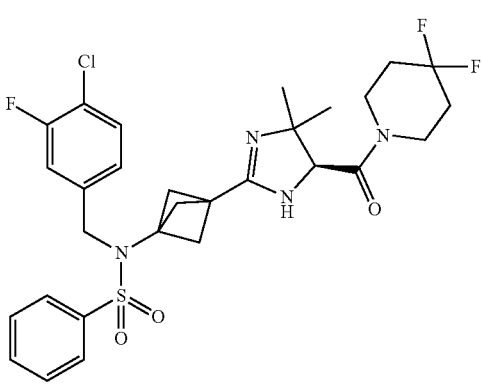 AND Enantiomer | MS: M/z Observed 610 |
| 249 | 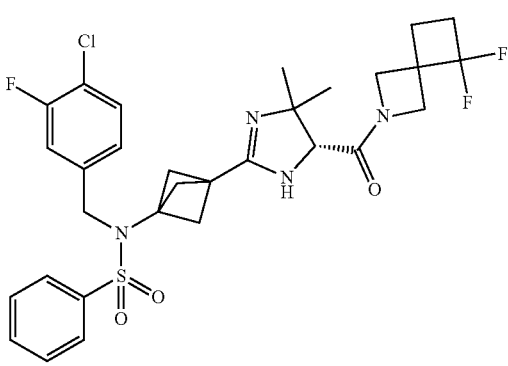 AND Enantiomer | MS: M/z Observed 622 |
| 250 | 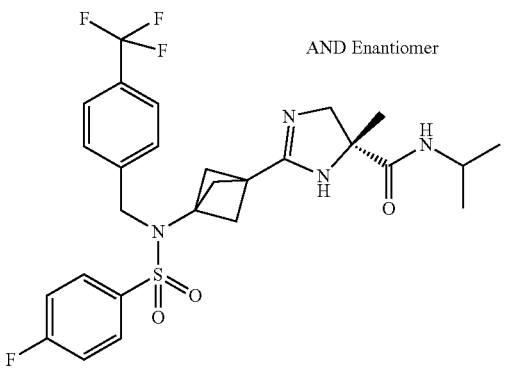 [SMILES: CC(C)NC(=O)[C@@]1(C)CN=C(C23CC(N(Cc4ccc(C(F)(F)F)cc4)S(=O)(=O)c4ccc(F)cc4)(C2)C3)N1] AND Enantiomer | MS: M/z Observed 567 |

| Example Number | Structure | Characterising Data |
|---|---|---|
| 251 | 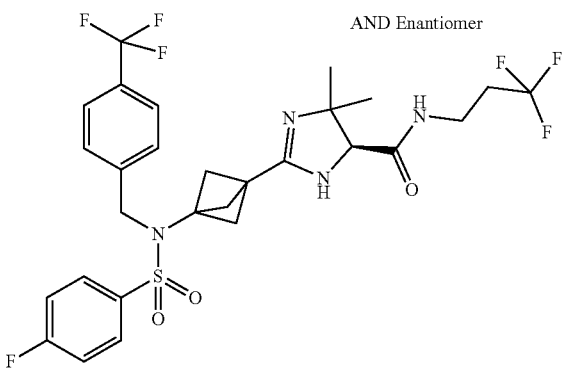 [SMILES: CC1(C)N=C(C23CC(N(Cc4ccc(C(F)(F)F)cc4)S(=O)(=O)c4ccc(F)cc4)(C2)C3)N[C@@H]1C(=O)NCCC(F)(F)F] AND Enantiomer | MS: M/z Observed 635 |
| 252 | 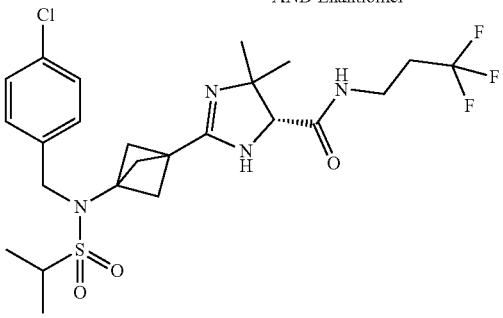 AND Enantiomer | MS: M/z Observed 550 |
| 253 | 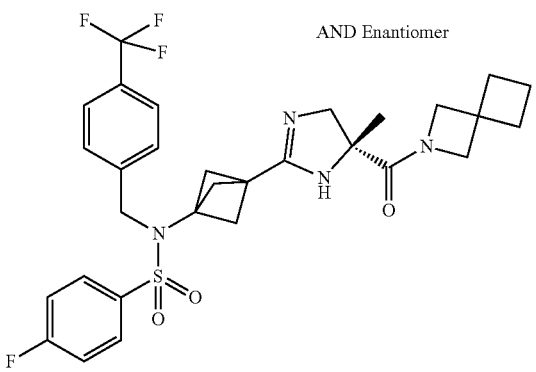 [SMILES: C[C@]1(C(=O)N2CC3(CCC3)C2)CN=C(C23CC(N(Cc4ccc(C(F)(F)F)cc4)S(=O)(=O)c4ccc(F)cc4)(C2)C3)N1] AND Enantiomer | MS: M/z Observed 605 |
| 254 | 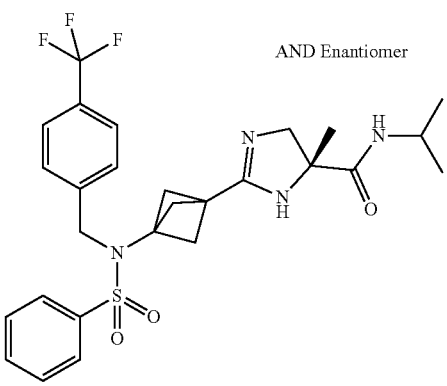 [SMILES: CC(C)NC(=O)[C@@]1(C)CN=C(C23CC(N(Cc4ccc(C(F)(F)F)cc4)S(=O)(=O)c4ccccc4)(C2)C3)N1] AND Enantiomer | MS: M/z Observed 549 |

| Example Number | Structure | Characterising Data |
|---|---|---|
| 255 | 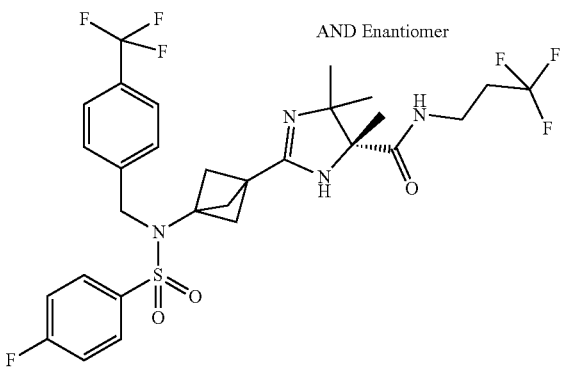 [SMILES: CC1(C)N=C(C23CC(N(Cc4ccc(C(F)(F)F)cc4)S(=O)(=O)c4ccc(F)cc4)(C2)C3)N[C@@]1(C)C(=O)NCCC(F)(F)F] AND Enantiomer | MS: M/z Observed 649 |
| 256 | 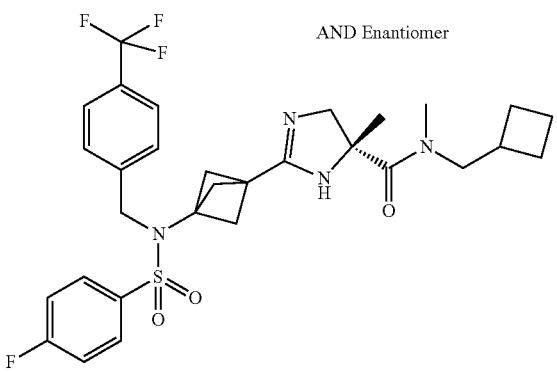 [SMILES: CN(CC1CCC1)C(=O)[C@@]1(C)CN=C(C23CC(N(Cc4ccc(C(F)(F)F)cc4)S(=O)(=O)c4ccc(F)cc4)(C2)C3)N1] AND Enantiomer | MS: M/z Observed 607 |
| 257 | 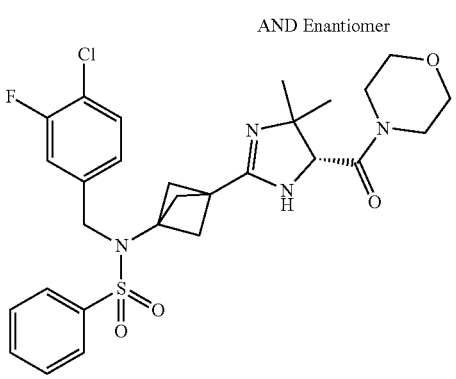 [SMILES: CC1(C)N=C(C23CC(N(Cc4ccc(Cl)c(F)c4)S(=O)(=O)c4ccccc4)(C2)C3)N[C@H]1C(=O)N1CCOCC1] AND Enantiomer | MS: M/z Observed 576 |
| 258 | 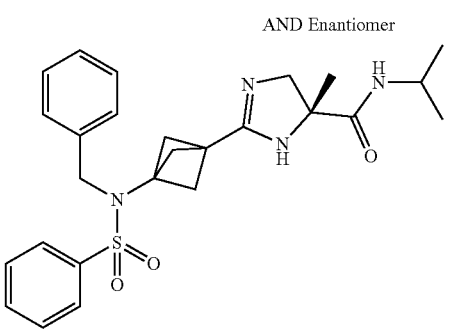 [SMILES: CC(C)NC(=O)[C@@]1(C)CN=C(C23CC(N(Cc4ccccc4)S(=O)(=O)c4ccccc4)(C2)C3)N1] AND Enantiomer | MS: M/z Observed 481 |

| Example Number | Structure | Characterising Data |
|---|---|---|
| 259 | AND Enantiomer HCl 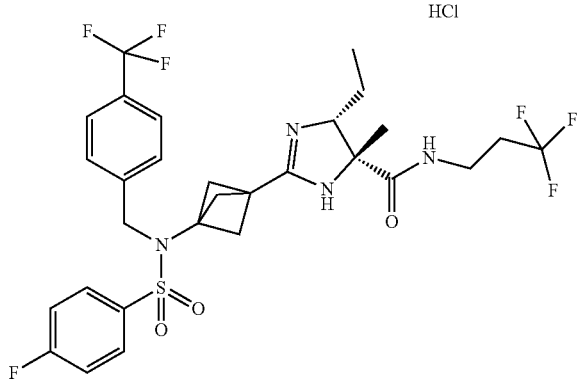 | MS: M/z Observed 686 |
| 260 | AND Enantiomer 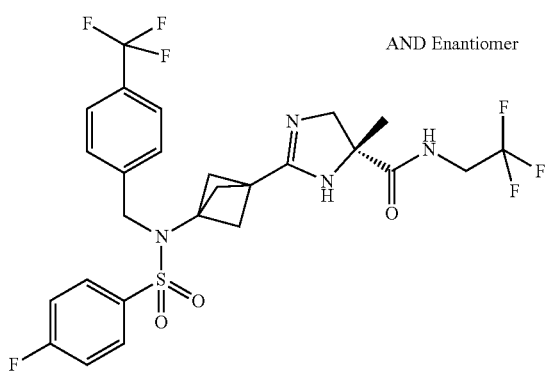 [SMILES: C[C@]1(C(=O)NCC(F)(F)F)CN=C(C23CC(N(Cc4ccc(C(F)(F)F)cc4)S(=O)(=O)c4ccc(F)cc4)(C2)C3)N1] | MS: M/z Observed 607 |
| 261 | AND Enantiomer 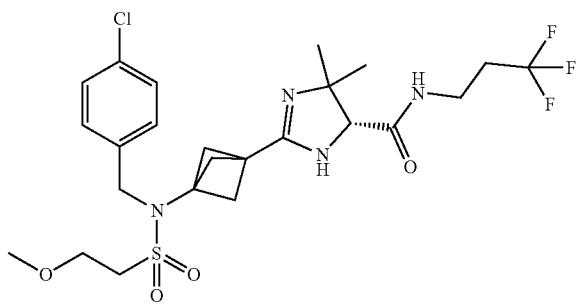 | MS: M/z Observed 566 |
| 262 | AND Enantiomer 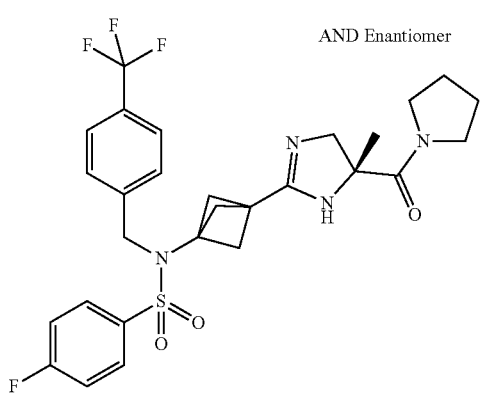 [SMILES: C[C@]1(C(=O)N2CCCC2)CN=C(C23CC(N(Cc4ccc(C(F)(F)F)cc4)S(=O)(=O)c4ccc(F)cc4)(C2)C3)N1] | MS: M/z Observed 579 |

| Example Number | Structure | Characterising Data |
|---|---|---|
| 263 | 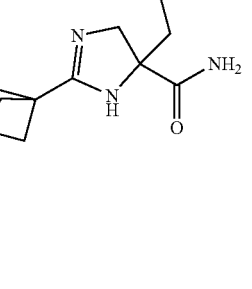 | MS: M/z Observed 601 |
| 264 | 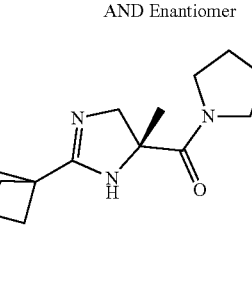 AND Enantiomer | MS: M/z Observed 607 |
| 265 | 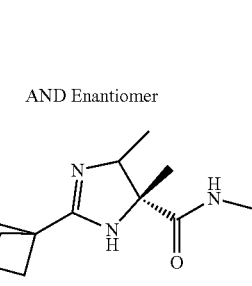 AND Enantiomer | MS: M/z Observed 635 |
| 266 | 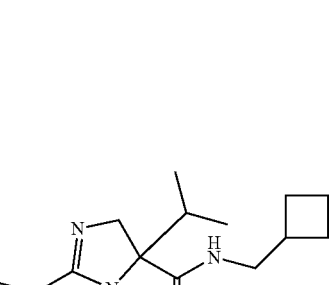 | MS: M/z Observed 621 |

| Example Number | Structure | Characterising Data |
|---|---|---|
| 267 | 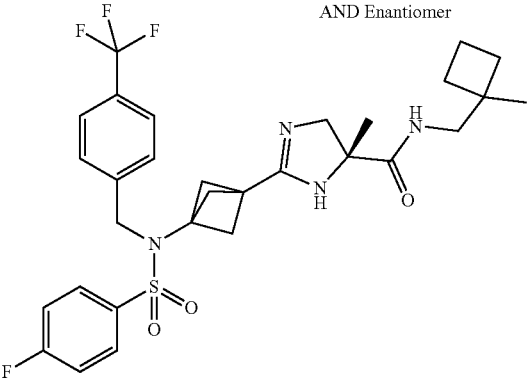 [SMILES: CC1(CNC(=O)[C@@]2(C)CN=C(C34CC(N(Cc5ccc(C(F)(F)F)cc5)S(=O)(=O)c5ccc(F)cc5)(C3)C4)N2)CCC1] AND Enantiomer | MS: M/z Observed 607 |
| 268 | 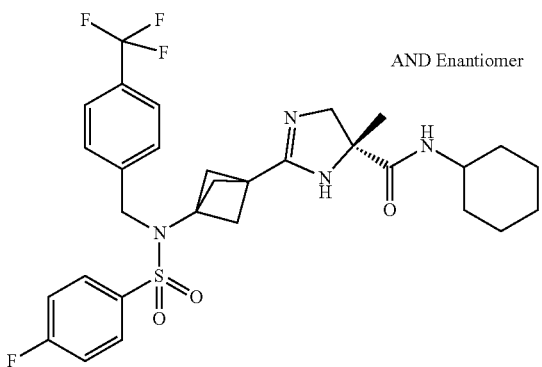 [SMILES: C[C@]1(C(=O)NC2CCCCC2)CN=C(C23CC(N(Cc4ccc(C(F)(F)F)cc4)S(=O)(=O)c4ccc(F)cc4)(C2)C3)N1] AND Enantiomer | MS: M/z Observed 607 |
| 269 | 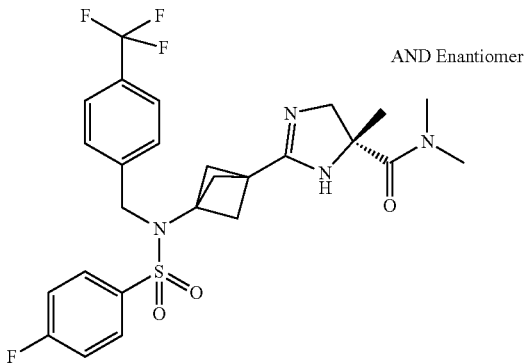 [SMILES: CN(C)C(=O)[C@@]1(C)CN=C(C23CC(N(Cc4ccc(C(F)(F)F)cc4)S(=O)(=O)c4ccc(F)cc4)(C2)C3)N1] AND Enantiomer | MS: M/z Observed 553 |
| 270 | 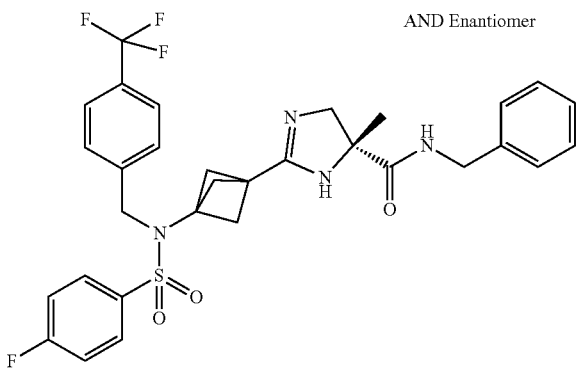 [SMILES: C[C@]1(C(=O)NCc2ccccc2)CN=C(C23CC(N(Cc4ccc(C(F)(F)F)cc4)S(=O)(=O)c4ccc(F)cc4)(C2)C3)N1] AND Enantiomer | MS: M/z Observed 615 |

-continued
| Example Number | Structure | Characterising Data |
|---|---|---|
| 271 | 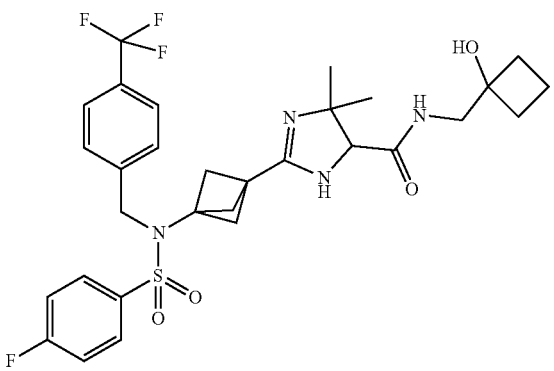 [SMILES: CC1(C)N=C(C23CC(N(Cc4ccc(C(F)(F)F)cc4)S(=O)(=O)c4ccc(F)cc4)(C2)C3)NC1C(=O)NCC1(O)CCC1] | MS: M/z Observed 623 |
| 272 | 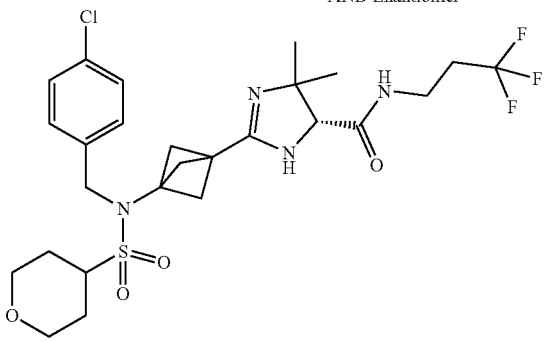 AND Enantiomer | MS: M/z Observed 592 |
| 273 | 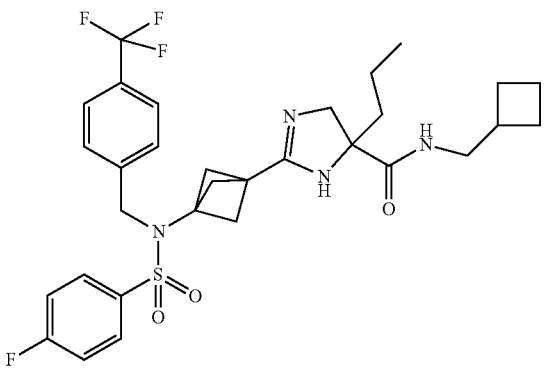 [SMILES: CCCC1(C(=O)NCC2CCC2)CN=C(C23CC(N(Cc4ccc(C(F)(F)F)cc4)S(=O)(=O)c4ccc(F)cc4)(C2)C3)N1] | MS: M/z Observed 621 |
| 274 | 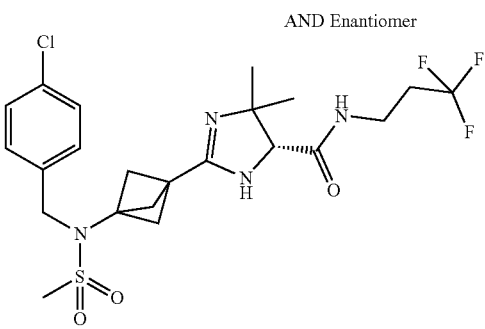 [SMILES: CC1(C)N=C(C23CC(N(Cc4ccc(Cl)cc4)S(C)(=O)=O)(C2)C3)N[C@H]1C(=O)NCCC(F)(F)F] AND Enantiomer | MS: M/z Observed 521 |

-continued
| Example Number | Structure | Characterising Data |
|---|---|---|
| 275 | 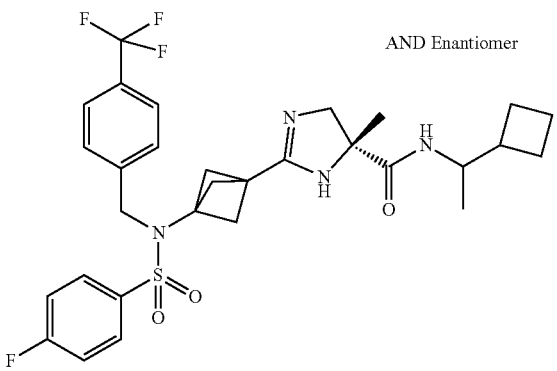 [SMILES: CC(NC(=O)[C@@]1(C)CN=C(C23CC(N(Cc4ccc(C(F)(F)F)cc4)S(=O)(=O)c4ccc(F)cc4)(C2)C3)N1)C1CCC1] AND Enantiomer | MS: M/z Observed 607 |
| 276 | 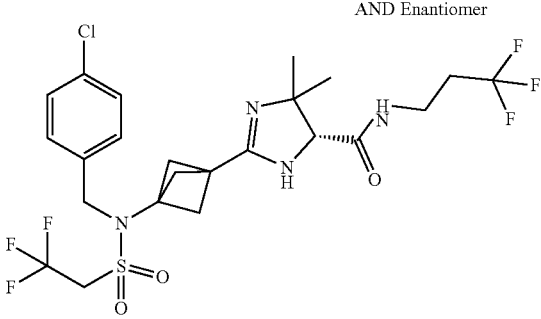 [SMILES: CC1(C)N=C(C23CC(N(Cc4ccc(Cl)cc4)S(=O)(=O)CC(F)(F)F)(C2)C3)N[C@H]1C(=O)NCCC(F)(F)F] AND Enantiomer | MS: M/z Observed 589 |
| 277 | 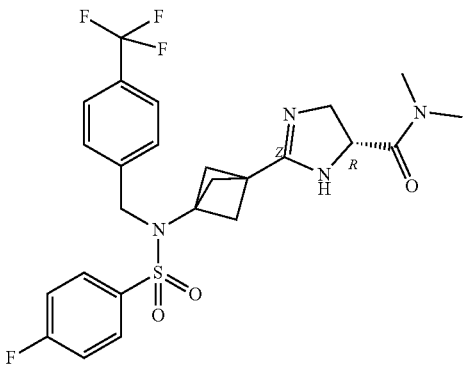 | MS: M/z Observed 539 |
| 278 | 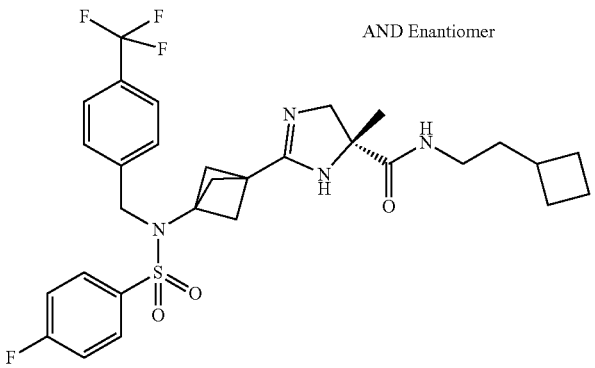 [SMILES: C[C@]1(C(=O)NCCC2CCC2)CN=C(C23CC(N(Cc4ccc(C(F)(F)F)cc4)S(=O)(=O)c4ccc(F)cc4)(C2)C3)N1] AND Enantiomer | MS: M/z Observed 607 |

-continued
| Example Number | Structure | Characterising Data |
|---|---|---|
| 279 | 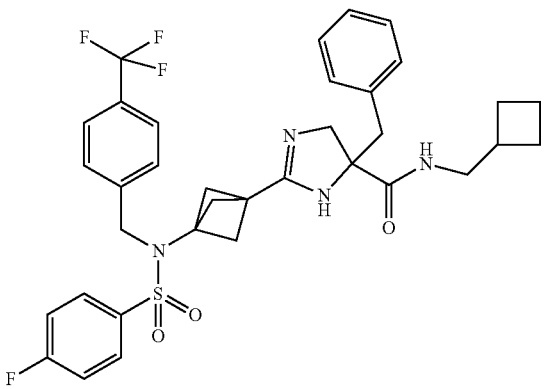 [SMILES: O=C(NCC1CCC1)C1(Cc2ccccc2)CN=C(C23CC(N(Cc4ccc(C(F)(F)F)cc4)S(=O)(=O)c4ccc(F)cc4)(C2)C3)N1] | MS: M/z Observed 669 |
| 280 | 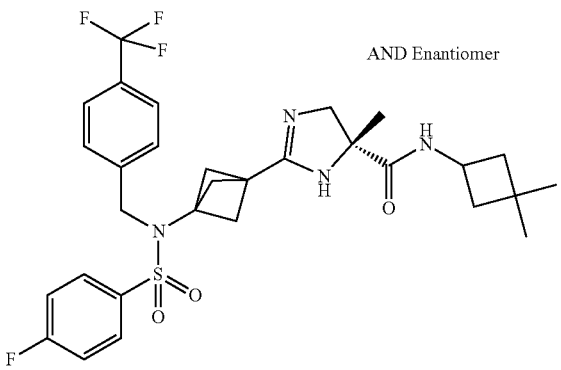 [SMILES: CC1(C)CC(NC(=O)[C@@]2(C)CN=C(C34CC(N(Cc5ccc(C(F)(F)F)cc5)S(=O)(=O)c5ccc(F)cc5)(C3)C4)N2)C1] AND Enantiomer | MS: M/z Observed 607 |
| 281 | 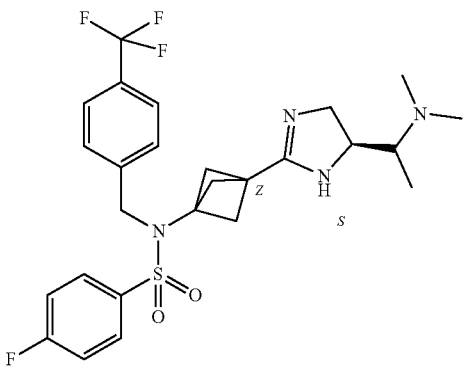 | MS: M/z Observed 539 |
| 282 | 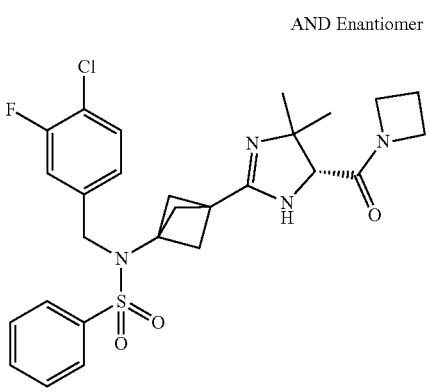 [SMILES: CC1(C)N=C(C23CC(N(Cc4ccc(Cl)c(F)c4)S(=O)(=O)c4ccccc4)(C2)C3)N[C@H]1C(=O)N1CCC1] AND Enantiomer | MS: M/z Observed 546 |

-continued
| Example Number | Structure | Characterising Data |
|---|---|---|
| 283 | 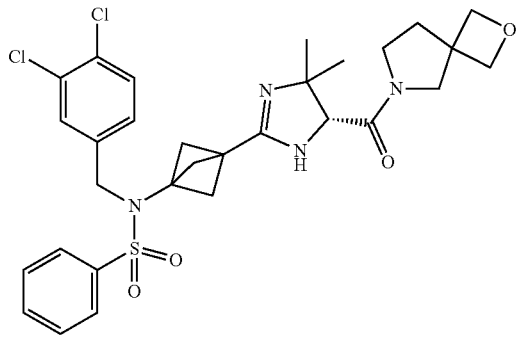 AND Enantiomer | MS: M/z Observed 618 |
| 284 | 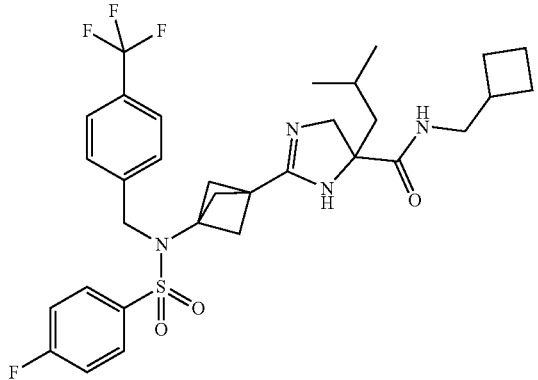 [SMILES: CC(C)CC1(C(=O)NCC2CCC2)CN=C(C23CC(N(Cc4ccc(C(F)(F)F)cc4)S(=O)(=O)c4ccc(F)cc4)(C2)C3)N1] | MS: M/z Observed 635 |
| 285 | 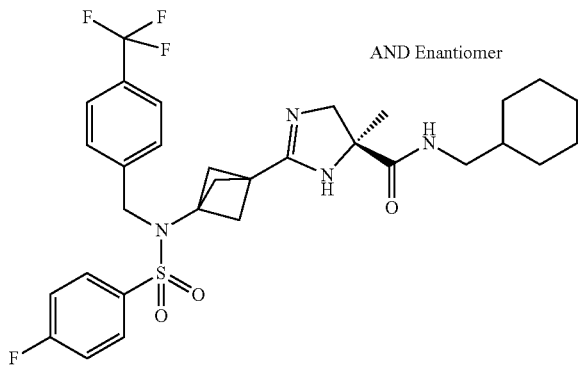 [SMILES: C[C@@]1(C(=O)NCC2CCCCC2)CN=C(C23CC(N(Cc4ccc(C(F)(F)F)cc4)S(=O)(=O)c4ccc(F)cc4)(C2)C3)N1] AND Enantiomer | MS: M/z Observed 621 |
| 286 | 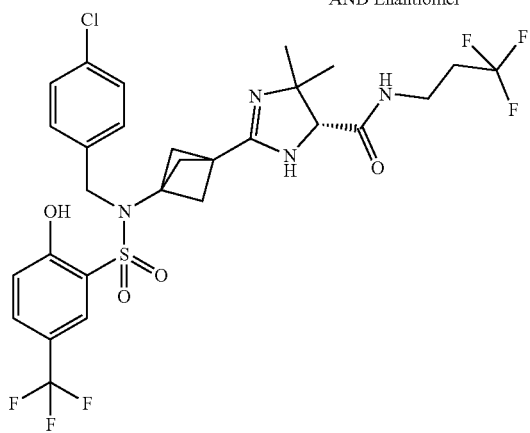 AND Enantiomer | MS: M/z Observed 668 |

-continued
| Example Number | Structure | Characterising Data |
|---|---|---|
| 287 | 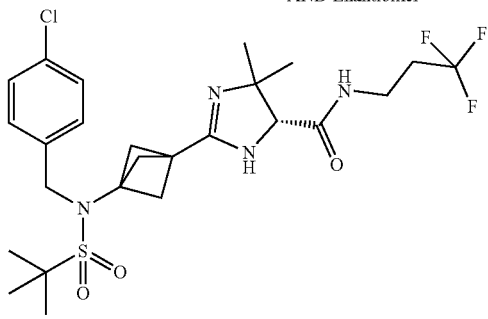 AND Enantiomer | MS: M/z Observed 564 |
| 288 | 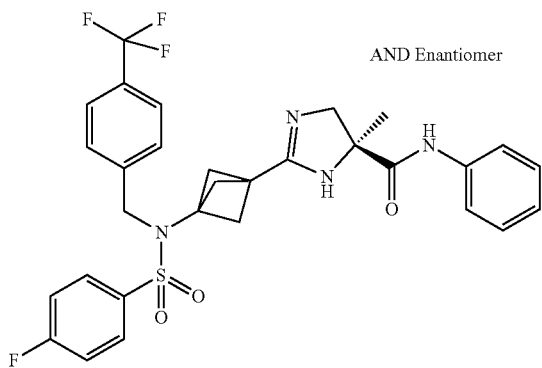 [SMILES: C[C@@]1(C(=O)Nc2ccccc2)CN=C(C23CC(N(Cc4ccc(C(F)(F)F)cc4)S(=O)(=O)c4ccc(F)cc4)(C2)C3)N1] AND Enantiomer | MS: M/z Observed 601 |
| 289 | 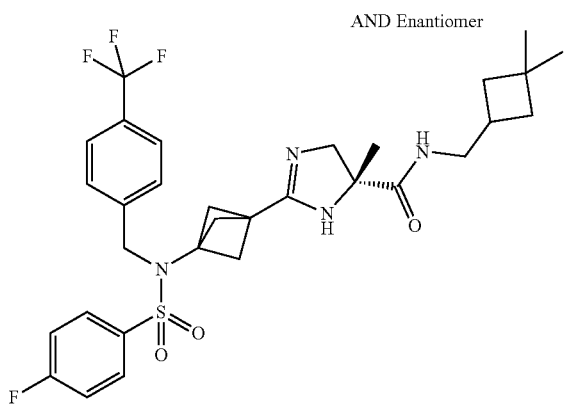 [SMILES: CC1(C)CC(CNC(=O)[C@@]2(C)CN=C(C34CC(N(Cc5ccc(C(F)(F)F)cc5)S(=O)(=O)c5ccc(F)cc5)(C3)C4)N2)C1] AND Enantiomer | MS: M/z Observed 621 |
| 290 | 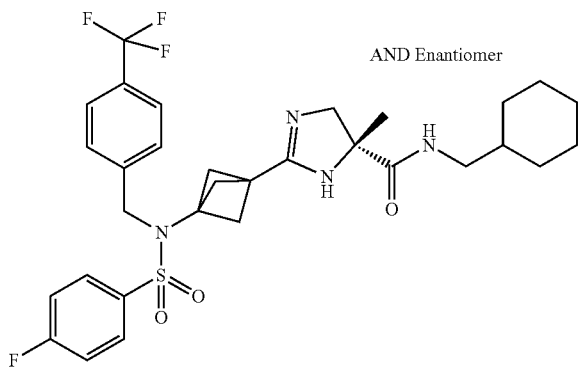 [SMILES: C[C@]1(C(=O)NCC2CCCCC2)CN=C(C23CC(N(Cc4ccc(C(F)(F)F)cc4)S(=O)(=O)c4ccc(F)cc4)(C2)C3)N1] AND Enantiomer | MS: M/z Observed 621 |

| Example Number | Structure | Characterising Data |
|---|---|---|
| 291 | 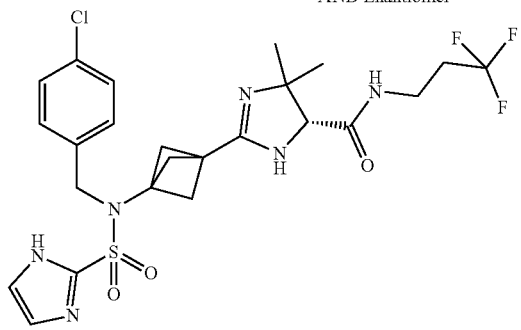 AND Enantiomer | MS: M/z Observed 574 |
| 292 | 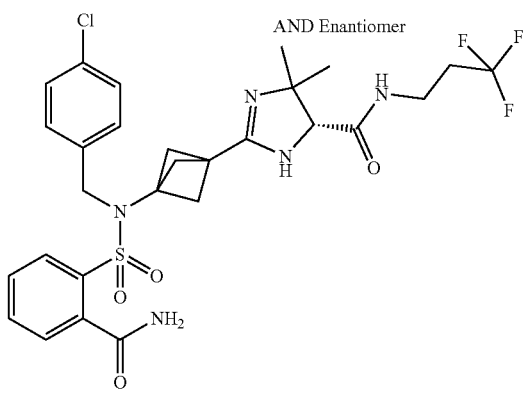 [SMILES: CC1(C)N=C(C23CC(N(Cc4ccc(Cl)cc4)S(=O)(=O)c4ccccc4C(N)=O)(C2)C3)N[C@H]1C(=O)NCCC(F)(F)F] AND Enantiomer | MS: M/z Observed 627 |
| 293 | 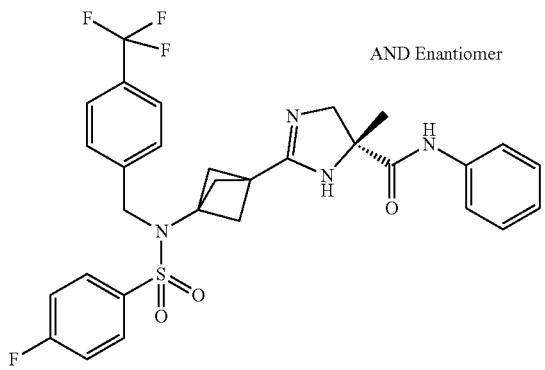 [SMILES: C[C@]1(C(=O)Nc2ccccc2)CN=C(C23CC(N(Cc4ccc(C(F)(F)F)cc4)S(=O)(=O)c4ccc(F)cc4)(C2)C3)N1] AND Enantiomer | MS: M/z Observed 601 |
| 294 | 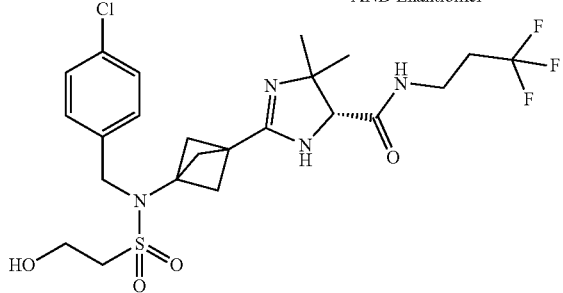 AND Enantiomer | MS: M/z Observed 552 |

| Example Number | Structure | Characterising Data |
|---|---|---|
| 295 | 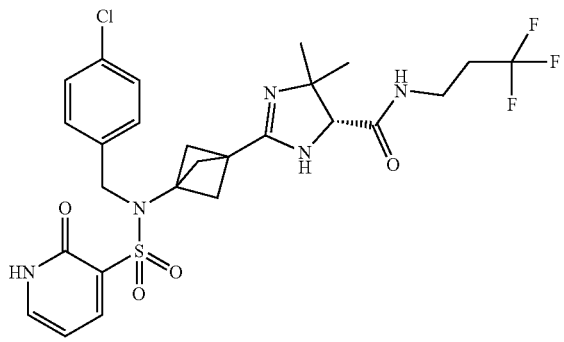 AND Enantiomer | MS: M/z Observed 601 |

Biological Assays
$K_v1.3$ Potency Evaluation
Electrophysiology Recordings

A proprietary Chinese hamster ovary cell line stably expressing exogenous human a-subunits of $K_v1.3$ (CHO-$K_v1.3$) channel, validated biophysically and pharmacologically in house, was used to assess the ability of test compounds to block $K_v1.3$ currents using automated patch clamp electrophysiology. The QPatch HT system (Sophion Bioscience A/S, Denmark) was used with the conventional whole-cell configuration. This system is an automated, chip-based planar patch clamp device allowing for up to 48 parallel independent experiments in one experimental assay run. Cells are added to each well and drawn by suction onto a small aperture to obtain a Gigaohm seal between the cell membrane and treated silicon surface, and whole-cell recordings initiated after access is achieved by suction and/or voltage pulses. The QPatch HT uses static perfusion, whereby a small volume of recording solution or drug is added to a reservoir on the chip and the solution perfuses across the cell through quartz-lined microfluidic channels; this solution is removed by capillary action when the next sample application is made.

CHO-$K_v1.3$ cells were prepared for experiments by dissociation from T175 cell culture flasks using trypsin-EDTA (0.05%), cells were kept in serum free media in the cell hotel on board the QPatch HT. These cells were sampled, washed and re-suspended in extracellular recording solution by the QPatch HT immediately before application to the recording well site on the chip. Experiments were performed using the following solutions; extracellular solution contained (in mM); 150 NaCl, 10 KCl, 1 $MgCl_2$, 3 $CaCl_2$), 10 Glucose and 10 HEPES (pH 7.4, NaOH) and intracellular solution contained (in mM); 20 KCl, 120 KF, 10 HEPES, 10 EGTA, 5 ATP (pH 7.2, KOH).

The potency (Inhibitory Concentration 50%, $IC_{50}$) of synthesized compounds against $K_v1.3$ was determined from concentration-response relationships established by cumulatively applying four escalating concentrations of test compound to an individual cell and a minimum of N≥3 individual cells of data per compound were used to generate the $IC_{50}$ value.

On achieving the whole-cell configuration; two additions of vehicle (0.1-0.3% DMSO v/v) were applied to each cell in two bolus additions with a two minute recording period between each addition (four minutes total recording time).

Following the vehicle period, four concentrations of test sample were applied as two bolus additions per test concentration at two minute intervals, and the effects on current measured during the four minute recording period.

Currents were elicited using a single step voltage protocol. From a holding potential of −80 mV the cell is depolarised to +30 mV (500 ms) resulting in an outward current before finally repolarising the cell by returning to the holding potential. The command voltage was applied at a frequency of 0.067 Hz throughout the duration of the experiment. For each sweep of the voltage protocol membrane current and the passive properties of the individual cells were recorded by QPatch assay software (version 5.2). Cursors were placed to calculate the charge (integral of the current recorded during cursor interval) between 2-490 ms (0.4-99%) of the 500 ms step to +30 mV.

The % inhibition of charge for each test concentration application period was calculated as the reduction in mean charge at the end of each concentration test period relative to the charge value measured at the end of the control (i.e. vehicle) period. Sigmoidal concentration response curves (four parameter logistic curve) were fitted to the % inhibition rom which the $IC_{50}$ was determined. Curve fits were constrained at 0 and 100%.

The compounds of the invention were tested in the above referenced assay and the results are shown in Table 1:

TABLE 1

Kv1.3 Potency Values

| Example Number | $hK_v1.3$ $IC_{50}$ μM |
|---|---|
| 1 | 0.035 |
| 2 | 0.030 |
| 3 | 0.061 |
| 4 | 0.079 |
| 5 | 0.138 |
| 6 | 0.02 |
| 7 | 0.026 |
| 8 | 0.027 |
| 9 | 0.028 |
| 10 | 0.028 |
| 11 | 0.028 |
| 12 | 0.03 |
| 13 | 0.037 |
| 14 | 0.033 |
| 15 | 0.033 |
| 16 | 0.035 |

TABLE 1-continued

Kv1.3 Potency Values

| Example Number | hK$_v$1.3 IC$_{50}$ μM |
|---|---|
| 17 | 0.035 |
| 18 | 0.036 |
| 19 | 0.037 |
| 20 | 0.037 |
| 21 | 0.038 |
| 22 | 0.039 |
| 23 | 0.04 |
| 24 | 0.04 |
| 25 | 0.04 |
| 26 | 0.054 |
| 27 | 0.04 |
| 28 | 0.04 |
| 29 | 0.04 |
| 30 | 0.041 |
| 31 | 0.042 |
| 32 | 0.043 |
| 33 | 0.043 |
| 34 | 0.047 |
| 35 | 0.044 |
| 36 | 0.045 |
| 37 | 0.045 |
| 38 | 0.045 |
| 39 | 0.045 |
| 40 | 0.046 |
| 41 | 0.046 |
| 42 | 0.046 |
| 43 | 0.046 |
| 44 | 0.046 |
| 45 | 0.046 |
| 46 | 0.047 |
| 47 | 0.047 |
| 48 | 0.048 |
| 49 | 0.048 |
| 50 | 0.048 |
| 51 | 0.048 |
| 52 | 0.049 |
| 53 | 0.049 |
| 54 | 0.05 |
| 55 | 0.05 |
| 56 | 0.05 |
| 57 | 0.05 |
| 58 | 0.05 |
| 59 | 0.051 |
| 60 | 0.051 |
| 61 | 0.051 |
| 62 | 0.052 |
| 63 | 0.052 |
| 64 | 0.052 |
| 65 | 0.053 |
| 66 | 0.053 |
| 67 | 0.053 |
| 68 | 0.055 |
| 69 | 0.055 |
| 70 | 0.056 |
| 71 | 0.057 |
| 72 | 0.057 |
| 73 | 0.058 |
| 74 | 0.058 |
| 75 | 0.059 |
| 76 | 0.06 |
| 77 | 0.06 |
| 78 | 0.06 |
| 79 | 0.06 |
| 80 | 0.061 |
| 81 | 0.061 |
| 82 | 0.061 |
| 83 | 0.061 |
| 84 | 0.061 |
| 85 | 0.062 |
| 86 | 0.062 |
| 87 | 0.063 |
| 88 | 0.063 |
| 89 | 0.063 |
| 90 | 0.064 |
| 91 | 0.064 |
| 92 | 0.064 |
| 93 | 0.064 |
| 94 | 0.064 |
| 95 | 0.064 |
| 96 | 0.065 |
| 97 | 0.066 |
| 98 | 0.066 |
| 99 | 0.067 |
| 100 | 0.067 |
| 101 | 0.067 |
| 102 | 0.068 |
| 103 | 0.068 |
| 104 | 0.069 |
| 105 | 0.069 |
| 106 | 0.07 |
| 107 | 0.071 |
| 108 | 0.071 |
| 109 | 0.071 |
| 110 | 0.072 |
| 111 | 0.072 |
| 112 | 0.072 |
| 113 | 0.072 |
| 114 | 0.073 |
| 115 | 0.073 |
| 116 | 0.073 |
| 117 | 0.073 |
| 118 | 0.074 |
| 119 | 0.074 |
| 120 | 0.074 |
| 121 | 0.075 |
| 122 | 0.075 |
| 123 | 0.075 |
| 124 | 0.075 |
| 125 | 0.075 |
| 126 | 0.076 |
| 127 | 0.077 |
| 128 | 0.077 |
| 129 | 0.078 |
| 130 | 0.078 |
| 131 | 0.078 |
| 132 | 0.078 |
| 133 | 0.078 |
| 134 | 0.079 |
| 135 | 0.081 |
| 136 | 0.082 |
| 137 | 0.082 |
| 138 | 0.084 |
| 139 | 0.084 |
| 140 | 0.084 |
| 141 | 0.084 |
| 142 | 0.084 |
| 143 | 0.085 |
| 144 | 0.087 |
| 145 | 0.088 |
| 146 | 0.088 |
| 147 | 0.088 |
| 148 | 0.089 |
| 149 | 0.089 |
| 150 | 0.09 |
| 151 | 0.09 |
| 152 | 0.091 |
| 153 | 0.091 |
| 154 | 0.091 |
| 155 | 0.092 |
| 156 | 0.092 |
| 157 | 0.094 |
| 158 | 0.095 |
| 159 | 0.095 |
| 160 | 0.097 |
| 161 | 0.098 |
| 162 | 0.098 |
| 163 | 0.098 |
| 164 | 0.099 |
| 165 | 0.099 |
| 166 | 0.099 |
| 167 | 0.099 |
| 168 | 0.099 |

TABLE 1-continued
Kv1.3 Potency Values
| Example Number | hK$_v$1.3 IC$_{50}$ μM |
|---|---|
| 169 | 0.1 |
| 170 | 0.101 |
| 171 | 0.102 |
| 172 | 0.103 |
| 173 | 0.103 |
| 174 | 0.103 |
| 175 | 0.104 |
| 176 | 0.104 |
| 177 | 0.104 |
| 178 | 0.105 |
| 179 | 0.105 |
| 180 | 0.106 |
| 181 | 0.106 |
| 182 | 0.108 |
| 183 | 0.108 |
| 184 | 0.109 |
| 185 | 0.109 |
| 186 | 0.11 |
| 187 | 0.11 |
| 188 | 0.112 |
| 189 | 0.112 |
| 190 | 0.113 |
| 191 | 0.114 |
| 192 | 0.115 |
| 193 | 0.115 |
| 194 | 0.121 |
| 195 | 0.124 |
| 196 | 0.125 |
| 197 | 0.126 |
| 198 | 0.126 |
| 199 | 0.129 |
| 200 | 0.129 |
| 201 | 0.131 |
| 202 | 0.134 |
| 203 | 0.134 |
| 204 | 0.135 |
| 205 | 0.136 |
| 206 | 0.137 |
| 207 | 0.137 |
| 208 | 0.143 |
| 209 | 0.144 |
| 210 | 0.144 |
| 211 | 0.148 |
| 212 | 0.149 |
| 213 | 0.152 |
| 214 | 0.159 |
| 215 | 0.159 |
| 216 | 0.163 |
| 217 | 0.167 |
| 218 | 0.168 |
| 219 | 0.168 |
| 220 | 0.169 |
| 221 | 0.169 |
| 222 | 0.17 |
| 223 | 0.177 |
| 224 | 0.178 |
| 225 | 0.182 |
| 226 | 0.185 |
| 227 | 0.186 |
| 228 | 0.19 |
| 229 | 0.199 |
| 230 | 0.201 |
| 231 | 0.205 |
| 232 | 0.208 |
| 233 | 0.209 |
| 234 | 0.211 |
| 235 | 0.212 |
| 236 | 0.213 |
| 237 | 0.217 |
| 238 | 0.221 |
| 239 | 0.23 |
| 240 | 0.235 |
| 241 | 0.243 |
| 242 | 0.248 |
| 243 | 0.251 |
| 244 | 0.252 |
| 245 | 0.253 |
| 246 | 0.258 |
| 247 | 0.262 |
| 248 | 0.275 |
| 249 | 0.28 |
| 250 | 0.286 |
| 251 | 0.307 |
| 252 | 0.317 |
| 253 | 0.323 |
| 254 | 0.333 |
| 255 | 0.341 |
| 256 | 0.342 |
| 257 | 0.348 |
| 258 | 0.362 |
| 259 | 0.365 |
| 260 | 0.37 |
| 261 | 0.386 |
| 262 | 0.395 |
| 263 | 0.4 |
| 264 | 0.404 |
| 265 | 0.408 |
| 266 | 0.415 |
| 267 | 0.424 |
| 268 | 0.441 |
| 269 | 0.481 |
| 270 | 0.485 |
| 271 | 0.494 |
| 272 | 0.524 |
| 273 | 0.552 |
| 274 | 0.559 |
| 275 | 0.571 |
| 276 | 0.575 |
| 277 | 0.593 |
| 278 | 0.595 |
| 279 | 0.608 |
| 280 | 0.615 |
| 281 | 0.632 |
| 282 | 0.706 |
| 283 | 0.749 |
| 284 | 0.787 |
| 285 | 0.802 |
| 286 | 0.859 |
| 287 | 0.976 |
| 288 | 1.02 |
| 289 | 1.058 |
| 290 | 1.064 |
| 291 | 1.119 |
| 292 | 2.946 |
| 293 | 4.082 |
| 294 | 10.508 |
| 295 | 21.426 |
The invention claimed is:
1. A compound of formula (I):
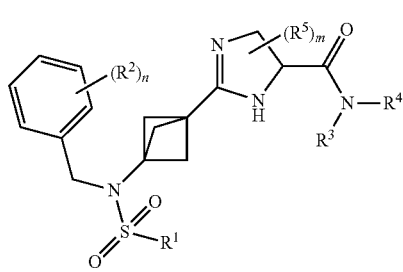
or a pharmaceutically acceptable salt or a solvate thereof, wherein:
R$^1$ represents C$_{1-6}$ alkyl, C$_{1-6}$ alkoxy, C$_{1-6}$ alkanol, —X—C$_{3-8}$ cycloalkyl, haloC$_{1-6}$ alkyl, aryl, heterocyclyl or heteroaryl, wherein said cycloalkyl, aryl, heterocyclyl or heteroaryl groups may be optionally substituted by one or more $R^a$ groups;

$R^a$ represents $C_{1-6}$ alkyl, halogen, halo$C_{1-6}$ alkyl, hydroxy, cyano, nitro, oxo, $CONR^xR^y$ or $C_{3-8}$ cycloalkyl;

$R^x$ and $R^y$ independently represent hydrogen or $C_{1-6}$ alkyl;

X represents a bond, —$CH_2$— or —$(CH_2)_2$—;

$R^2$ represents halogen, halo$C_{1-6}$ alkyl or cyano;

n represents an integer selected from 0 to 4;

$R^3$ represents hydrogen, $C_{1-6}$ alkyl, —X—$C_{3-8}$ cycloalkyl, halo$C_{1-6}$ alkyl or —X-aryl, wherein said alkyl may be optionally substituted by one or more cycloalkyl groups, wherein said cycloalkyl may be optionally substituted by one or more $C_{1-6}$ alkyl, $C_{1-6}$ alkoxy, halo$C_{1-6}$ alkyl, halogen, hydroxy or cyano groups, wherein said haloalkyl may be optionally substituted by one or more hydroxy groups, wherein said aryl may be optionally substituted by one or more halogen groups, wherein $R^3$ and $R^4$ together with the nitrogen atom to which they are attached may join to form a heterocyclyl ring optionally substituted by one or more $C_{1-6}$ alkyl, halo$C_{1-6}$ alkyl, or halogen;

$R^4$ represents hydrogen, $C_{1-6}$ alkyl or $C_{3-8}$ cycloalkyl;

$R^5$ represents $C_{1-6}$ alkyl or —X-aryl; and m represents an integer selected from 0 to 4, such that when m represents 2, said $R^5$ groups may join to form a $C_{3-8}$ cycloalkyl group.

2. A compound of formula (I) as defined in claim 1, or a pharmaceutically acceptable salt or a solvate thereof, wherein $R^1$ represents:

methyl, ethyl, n-propyl, i-propyl, n-butyl, i-butyl, t-butyl, n-pentyl or i-pentyl;

propoxy;

cycloalkyl selected from —($CH_2$)-cyclopropyl, —($CH_2$)$_2$-cyclopropyl, -cyclobutyl, —($CH_2$)-cyclobutyl, -cyclopentyl and -cyclohexyl;

trifluoromethyl, fluoropropyl, difluoropropyl, trifluoropropyl, fluorobutyl, difluorobutyl or trifluorobutyl;

phenyl;

heterocyclyl selected from pyrrolidinyl and tetrahydropyranyl; or heteroaryl selected from furanyl, thiophenyl, pyrazolyl, pyridinyl and imidazolyl;

wherein said cycloalkyl, phenyl, heterocyclyl or heteroaryl groups may be optionally substituted by one or more $R^a$ groups, or $R^1$ represents:

trifluoromethyl, fluoropropyl, difluoropropyl, trifluoropropyl, fluorobutyl, difluorobutyl or trifluorobutyl;

phenyl; or heteroaryl selected from furanyl, thiophenyl, pyrazolyl, pyridinyl and imidazolyl;

wherein said phenyl or heteroaryl groups may be optionally substituted by one or more $R^a$ groups; or $R^1$ represents:

fluoropropyl, phenyl or pyridinyl;

or $R^1$ represents:

unsubstituted phenyl; or unsubstituted pyridyl.

3. A compound of formula (I) as defined in claim 1, or a pharmaceutically acceptable salt or a solvate thereof, wherein $R^a$ represents methyl, fluorine, chlorine, trifluoromethyl, hydroxy, cyano, nitro, oxo, $CONH_2$ or cyclopropyl.

4. A compound of formula (I) as defined in claim 1, or a pharmaceutically acceptable salt or a solvate thereof, wherein $R^2$ represents fluorine, chlorine, difluoromethyl, trifluoromethyl or cyano; or $R^2$ represents halogen; or $R^2$ represents fluorine or chlorine.

5. A compound of formula (I) as defined in claim 1, or a pharmaceutically acceptable salt or a solvate thereof, wherein n represents an integer selected from 0 to 3; or n represents an integer selected from 1 or 2.

6. A compound of formula (I) as defined in claim 5, or a pharmaceutically acceptable salt or a solvate thereof, wherein n represents an integer selected from 0.

7. A compound of formula (I) as defined in claim 5, or a pharmaceutically acceptable salt or a solvate thereof, wherein n represents 1 and $R^2$ represents fluorine, chlorine, difluoromethyl, trifluoromethyl or cyano; or n represents 1 and $R^2$ represents 3-fluorine, 4-fluorine, 3-chlorine, 4-chlorine, 4-difluoromethyl, 4-trifluoromethyl or 4-cyano; or n represents 1 and $R^2$ represents 4-chlorine.

8. A compound of formula (I) as defined in claim 5, or a pharmaceutically acceptable salt or a solvate thereof, wherein n represents 2 and $R^2$ represents fluorine, chlorine, trifluoromethyl or cyano; or n represents 2 and $R^2$ represents: 2-fluoro, 4-chloro; 3-fluoro, 4-chloro; 3-chloro, 4-fluoro; 3-fluoro, 4-trifluoromethyl; 3-chloro, 4-trifluoromethyl; 3-cyano, 4-chloro; 3,4-difluoro; or 3,4-dichloro; or n represents 2 and $R^2$ represents 3-fluoro, 4-chloro.

9. A compound of formula (I) as defined in claim 5, or a pharmaceutically acceptable salt or a solvate thereof, wherein n represents 3 and $R^2$ represents fluorine or chlorine; or n represents 3 and $R^2$ represents 3,5-difluoro, 4-chloro.

10. A compound of formula (I) as defined in claim 1, or a pharmaceutically acceptable salt or a solvate thereof, wherein $R^3$ represents:

hydrogen;

methyl, n-propyl, i-propyl, dimethylpropyl, n-butyl or t-butyl optionally substituted by one or more cyclopropyl groups;

cyclopropyl, —$CH_2$-cyclopropyl, —$(CH_2)_2$-cyclopropyl, -cyclobutyl, —$CH_2$-cyclobutyl, —$(CH_2)_2$-cyclobutyl, —C(H)($CH_3$)-cyclobutyl, cyclohexyl, —$CH_2$-cyclohexyl or bicyclo[1.1.1]pentanyl optionally substituted by one or more methyl, methoxy, difluoromethyl, trifluoromethyl, trifluoroethyl, fluorine, hydroxy or cyano groups;

trifluoroethyl, difluoropropyl, trifluoropropyl, pentafluoropropyl, fluorobutyl, trifluorobutyl or trifluoropentyl optionally substituted by one or more hydroxy groups;

-phenyl or —$CH_2$-phenyl optionally substituted by one or more fluorine groups;

or $R^3$ and $R^4$ together with the nitrogen atom to which they are attached join to form a azetidinyl, pyrrolidinyl, piperidinyl, morpholinyl, azepinyl, 1-azaspiro[3.3]heptyl, 5-azaspiro[2.4]heptyl, 5-azaspiro[3.4]octyl, 8-azabicyclo[3.2.1]octyl, 3-azabicyclo[3.1.0]hexyl, octahydrocyclopenta[c]pyrrolyl, 2-azaspiro[3.3]heptyl, 3-azabicyclo[3.2.1]octyl, 6-azaspiro[3.4]octyl, 5-azaspiro[2.5]octyl or 2-oxa-6-azaspiro[3.4]octyl ring optionally substituted by one or more methyl, difluoromethyl, trifluoromethyl, or fluorine); or $R^3$ represents:

cyclopropyl, —$CH_2$-cyclopropyl, —$(CH_2)_2$-cyclopropyl, -cyclobutyl, —$CH_2$-cyclobutyl, —$(CH_2)_2$-cyclobutyl, —C(H)($CH_3$)-cyclobutyl, cyclohexyl, —$CH_2$-cyclohexyl or bicyclo[1.1.1]pentanyl) optionally substituted by one or more methyl, methoxy, difluoromethyl, trifluoromethyl, trifluoroethyl, fluorine, hydroxy or cyano groups; or trifluoroethyl, difluoropropyl, trifluoropropyl, pentafluoropropyl, fluorobutyl, trifluorobutyl or trifluoropentyl optionally substituted by one or more hydroxy groups; or R³ represents:
bicyclo[1.1.1]pentanyl or trifluoropropyl; or R³ represents:
unsubstituted bicyclo[1.1.1]pentanyl or unsubstituted trifluoropropyl.

11. A compound of formula (I) as defined in claim 1, or a pharmaceutically acceptable salt or a solvate thereof, wherein R⁴ represents hydrogen, methyl, ethyl or cyclopropyl; or R⁴ represents hydrogen.

12. A compound of formula (I) as defined in claim 1, or a pharmaceutically acceptable salt or a solvate thereof, wherein m represents an integer selected from 0 to 3; or m represents an integer which is 2.

13. A compound of formula (I) as defined in claim 12, or a pharmaceutically acceptable salt or a solvate thereof, wherein m represents 0.

14. A compound of formula (I) as defined in claim 1, or a pharmaceutically acceptable salt or a solvate thereof, wherein R⁵ represents methyl, ethyl, n-propyl, i-propyl, i-butyl or —CH₂-phenyl; or m represents 2 and said two R⁵ groups join to form a cyclopropyl or cyclobutyl group; or R⁵ represents methyl, ethyl, n-propyl, i-propyl or i-butyl; or R⁵ represents methyl.

15. A compound of formula (I) as defined in claim 12, or a pharmaceutically acceptable salt or a solvate thereof, wherein m represents 1 and R⁵ represents methyl, n-propyl, i-propyl, i-butyl or —CH₂-phenyl).

16. A compound of formula (I) as defined in claim 12, or a pharmaceutically acceptable salt or a solvate thereof, wherein m represents 2 and R⁵ represents methyl or ethyl or said two R⁵ groups join to form a cyclopropyl or cyclobutyl group; or m represents 2 and R⁵ represents methyl or ethyl; or m represents 2 and R⁵ represents methyl.

17. A compound of formula (I) as defined in claim 12, or a pharmaceutically acceptable salt or a solvate thereof, wherein m represents 3 and R⁵ represents methyl.

18. A compound of formula (I) as defined in claim 1, which is the free base of a compound of Examples 1-295, or a pharmaceutically acceptable salt or solvate thereof.

19. A pharmaceutical composition comprising a compound of formula (I) as defined in claim 1, or a pharmaceutically acceptable salt or a solvate thereof.

20. A pharmaceutical composition comprising a compound of formula (I) as defined in claim 1, or a pharmaceutically acceptable salt or a solvate thereof, in combination with one or more therapeutic agents.

21. A method of treating a disease or condition mediated by overexpression of the potassium channel Kv1.3, wherein said disease or condition is selected from an autoimmune, inflammatory, cardiovascular, neuronal, auditory, renal or metabolic mediated disease, said method comprising administering to a subject a compound as defined in claim 1 or a pharmaceutically acceptable salt or a solvate thereof.

22. A process for preparing a compound of formula (I) as defined in claim 1, or a pharmaceutically acceptable salt or a solvate thereof, which comprises:

(a) reacting a compound of formula (II):

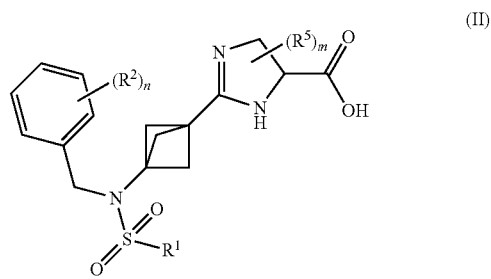

or salt thereof, wherein R¹, R², n, R⁵ and m are as defined in claim 1, with a compound of formula HNR³R⁴.

23. The process according to claim 22 for preparing a compound of formula (I) or a pharmaceutically acceptable salt or a solvate thereof, comprising:

(b) removal of a protecting group on an intermediate compound to prepare a compound of formula (I); and/or (c) interconversion of a compound of formula (I) to prepare an alternative compound of formula (I); and/or (d) formation of a pharmaceutically acceptable salt of a compound of formula (I).

* * * * *